United States Patent
McLoughlin et al.

(10) Patent No.: US 11,666,382 B2
(45) Date of Patent: Jun. 6, 2023

(54) LASER CONTROL USING A SPECTROMETER

(71) Applicant: GYRUS ACMI, INC., Southborough, MA (US)

(72) Inventors: Anne G. McLoughlin, Southborough, MA (US); Sergey A. Bukesov, Acton, MA (US); Kurt G. Shelton, Bedford, MA (US); Brian M. Talbot, Southborough, MA (US); Rachel D. Schnakenberg, Minneapolis, MN (US)

(73) Assignee: Gyrus ACMI, Inc., Westborough, MA (US)

(*) Notice: Subject to any disclaimer, the term of this patent is extended or adjusted under 35 U.S.C. 154(b) by 342 days.

(21) Appl. No.: 16/947,485

(22) Filed: Aug. 4, 2020

(65) Prior Publication Data
US 2021/0038306 A1    Feb. 11, 2021

Related U.S. Application Data

(60) Provisional application No. 63/027,005, filed on May 19, 2020, provisional application No. 62/893,959, (Continued)

(51) Int. Cl.
*A61B 18/22* (2006.01)
*A61B 5/00* (2006.01)
(Continued)

(52) U.S. Cl.
CPC ............ *A61B 18/22* (2013.01); *A61B 5/0022* (2013.01); *A61B 5/0075* (2013.01);
(Continued)

(58) Field of Classification Search
CPC ..... A61B 18/22; A61B 5/0022; A61B 5/0075; A61B 5/0084; A61B 5/4869; A61B 18/26;
(Continued)

(56) References Cited

U.S. PATENT DOCUMENTS

| 5,350,375 A | 9/1994 | Deckelbaum et al. |
| 6,554,824 B2 | 4/2003 | Davenport et al. |

(Continued)

FOREIGN PATENT DOCUMENTS

| CN | 114449946 A | 5/2022 |
| DE | 112020003715 T5 | 4/2022 |

(Continued)

OTHER PUBLICATIONS

"International Application Serial No. PCT/US2020/044896, International Search Report dated Oct. 28, 2020", 5 pgs.
(Continued)

*Primary Examiner* — Jonathan T Kuo
(74) *Attorney, Agent, or Firm* — Schwegman Lundberg & Woessner, P.A.

(57) ABSTRACT

Systems, devices, and methods for identifying a target in a body using a spectroscopic feedback from the target are disclosed. An exemplary surgical feedback control system comprises a feedback analyzer configured to receive a reflected signal from a target in response to electromagnetic radiation directed at a target, and a controller in operative communication with the feedback analyzer. The controller can generate a control signal to a surgical system to perform a predetermined operation based upon the received reflected signal, including determining a composition of the target, or programming a laser setting to direct laser energy to the target.

24 Claims, 36 Drawing Sheets

Related U.S. Application Data filed on Aug. 30, 2019, provisional application No. 62/882,837, filed on Aug. 5, 2019.

(51) Int. Cl.
*A61B 18/00* (2006.01)
*A61B 18/26* (2006.01)

(52) U.S. Cl.
CPC .......... *A61B 5/0084* (2013.01); *A61B 5/4869* (2013.01); *A61B 18/26* (2013.01); *A61B 2018/00482* (2013.01); *A61B 2018/00511* (2013.01); *A61B 2018/00577* (2013.01); *A61B 2018/00589* (2013.01); *A61B 2018/00625* (2013.01); *A61B 2018/00642* (2013.01)

(58) Field of Classification Search
CPC .......... A61B 2018/00511; A61B 2018/00642; A61B 2018/00904; A61B 18/20–18/28; A61N 5/06–2005/073
See application file for complete search history.

(56) References Cited

U.S. PATENT DOCUMENTS

| | | | |
|---|---|---|---|
| 9,017,316 | B2 | 4/2015 | Khatchaturov et al. |
| 9,061,369 | B2* | 6/2015 | Yoo ........................ B23K 26/38 |
| 9,445,871 | B2 | 9/2016 | Kang et al. |
| 9,486,286 | B2 | 11/2016 | Hodel et al. |
| 9,615,878 | B2* | 4/2017 | Nair ...................... A61B 8/0891 |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 2011/0100967 | A1* | 5/2011 | Yoo ........................ G01N 27/00 219/121.73 |
| 2014/0180273 | A1* | 6/2014 | Nair ...................... A61B 8/0891 606/34 |
| 2015/0224249 | A1 | 8/2015 | Ciulla et al. |
| 2015/0230864 | A1 | 8/2015 | Xuan et al. |
| 2015/0272674 | A1 | 10/2015 | Xuan et al. |
| 2016/0081749 | A1 | 3/2016 | Zhang et al. |
| 2016/0166319 | A1 | 6/2016 | Yu et al. |
| 2018/0092693 | A1 | 4/2018 | Falkenstein et al. |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0246908 | A1 | 8/2019 | Pyun et al. |
| 2019/0298449 | A1 | 10/2019 | Khachaturov et al. |
| 2019/0393669 | A1 | 12/2019 | Yu et al. |
| 2020/0253665 | A1* | 8/2020 | Brinkmann .............. A61B 5/06 |

FOREIGN PATENT DOCUMENTS

| | | |
|---|---|---|
| EP | 3510962 | 7/2019 |
| EP | 3512448 | 7/2019 |
| EP | 3522811 | 8/2019 |
| JP | 2022543792 A | 10/2022 |
| WO | 1990014797 | 12/1990 |
| WO | WO-2013154708 A1 | 10/2013 |
| WO | WO-2016201092 A1 | 12/2016 |
| WO | 2020033121 | 2/2020 |
| WO | WO-2021026161 A1 | 2/2021 |

OTHER PUBLICATIONS

"International Application Serial No. PCT/US2020/044896, Written Opinion dated Oct. 28, 2020", 6 pgs.

Bosschaart, Nienke, et al., "A literature review and novel theoretical approach on the optical properties of whole blood", Lasers Med Sci, (2014), 453-479.

Jacques, Steven, "Optical Absorption of Carbonized Tissue", [Online]. Retrieved from the Internet: <URL: https://omlc.org/spectra/carbon/>, (2018), 3 pgs.

Prahl, Scott, "Optical Absorption of Hemoglobin", [Online]. Retrieved from the Internet: <URL: http://omlc.org/spectra/hemoglobin/>, (1999), 4 pgs.

Vinnichenko, Victoriya, et al., "Comparison of a novel high-power blue diode laser ($\lambda$=442 nm) with Ho:YAG ($\lambda$=2100 nm), Tm fiber $\lambda$?=1940 nm), and KTP ($\lambda$=532 nm) lasers for soft tissue ablation", Proc. SPIE 10468, Therapeutics and Diagnostics in Urology, [Online]. Retrieved from the Internet: <URL: https://www.researchgate.net/publication/323002187>, (Feb. 2018), 8 pgs.

Vitruk, Peter, "Laser Surgery Basics—American Laser Study Club", [Online]. Retrieved from the Internet: <URL: http://www.americanlaserstudyclub.org/laser-surgery-education/>, (2020), 25 pgs.

"Chinese Application Serial No. 202080068398.6, Voluntary Amendment filed Aug. 26, 2022", with machine translation, 9 pgs.

"Indian Application Serial No. 202247004679, First Examination Report dated Aug. 4, 2022", 5 pgs.

"International Application Serial No. PCT/US2020/044896, International Preliminary Report on Patentability dated Feb. 17, 2022", 8 pgs.

* cited by examiner

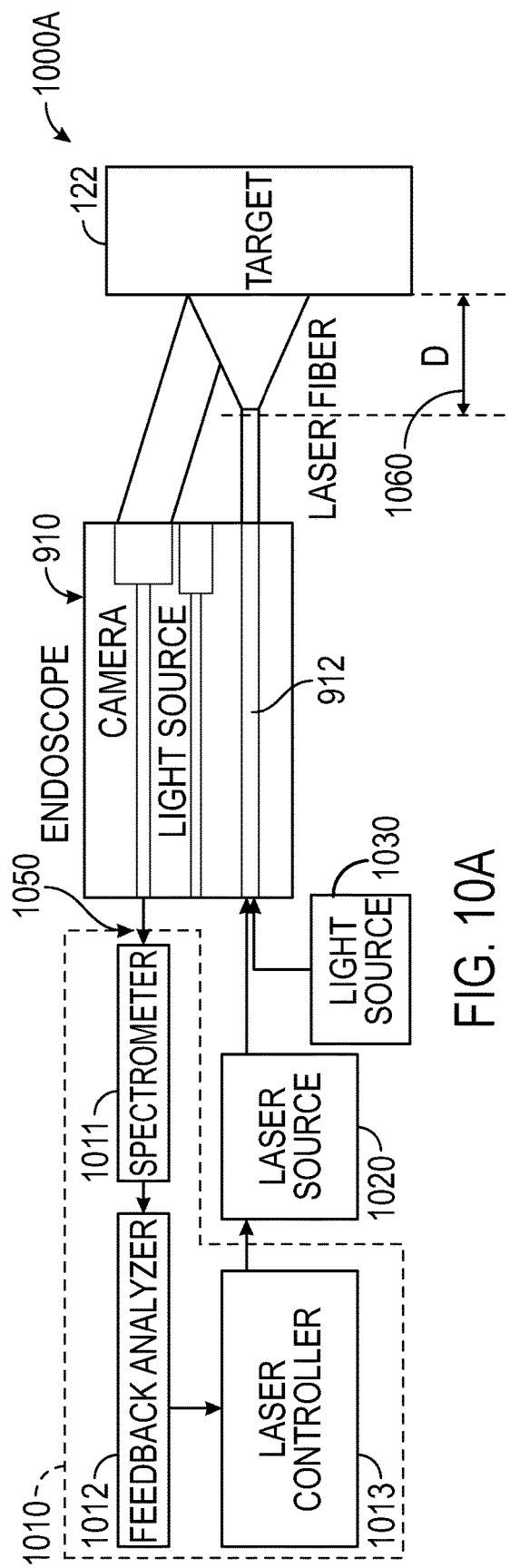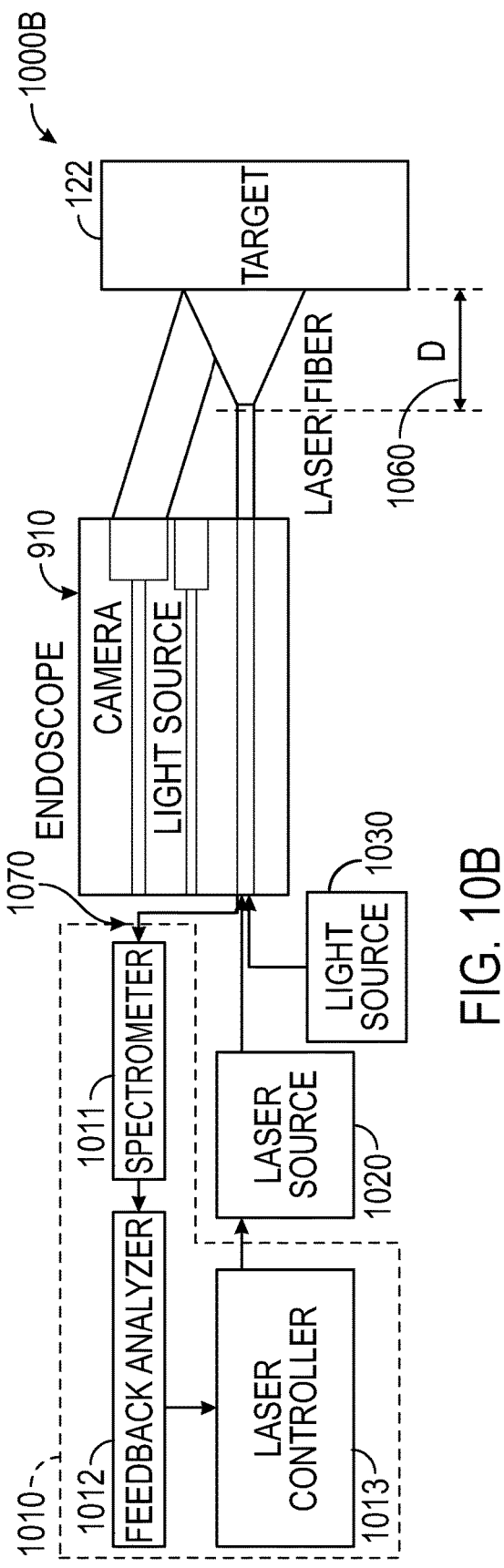

LASER CONTROL USING A SPECTROMETER

CLAIM OF PRIORITY

This application claims the benefit of priority under 35 U.S.C. § 119(e) of U.S. Provisional Patent Application Ser. No. 62/882,837, filed on Aug. 5, 2019, U.S. Provisional Patent Application Ser. No. 62/893,959, filed on Aug. 30, 2019, and U.S. Provisional Patent Application Ser. No. 63/027,005, filed on May 19, 2020, which are herein incorporated by reference in their entireties.

TECHNICAL FIELD

This document relates generally to surgical laser systems, and more specifically relates to systems and methods for identifying a target in a body using a spectroscopic feedback.

BACKGROUND

Endoscopes are typically used to provide access to an internal location of a subject such that a physician is provided with visual access. An endoscope is normally inserted into a patient's body, delivers light to a target (e.g., a target anatomy or object) being examined, and collects light reflected from the object. The reflected light carries information about the object being examined Some endoscopes include a working channel through which the operator can perform suction or pass instruments such as brushes, biopsy needles or forceps, or perform minimally invasive surgery to remove unwanted tissue or foreign objects from the body of the patient.

Laser or plasma systems have been used for delivering surgical laser energy to various target treatment areas such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments.

SUMMARY

The present document describes systems, devices, and methods for identifying a target in a body using a spectroscopic feedback from the target. An exemplary surgical feedback control system comprises a feedback analyzer configured to receive a reflected signal from a target in response to electromagnetic radiation directed at a target, and a controller in operative communication with the feedback analyzer. The controller can generate a control signal to a surgical system to perform a predetermined operation based upon the received reflected signal, including determining a composition of the target, or programming a laser setting to direct laser energy to the target.

Example 1 is a surgical feedback control system that comprises: a feedback analyzer configured to receive a reflected signal from a target in response to electromagnetic radiation directed at a target; a controller in operative communication with the feedback analyzer, the controller configured to generate a control signal to a surgical system to perform a predetermined operation based upon the received reflected signal.

In Example 2, the subject matter of Example 1 optionally includes, wherein: the feedback analyzer includes, or is coupled to, a spectrometer configured to collect spectroscopic data based on the received reflected signal; and the controller is configured to generate the control signal to the surgical system to perform the predetermined operation based on the spectroscopic data.

In Example 3, the subject matter of any one or more of Examples 1-2 optionally include an optical fiber coupled to a radiation source, the optical fiber configured to transmit the electromagnetic radiation generated by the radiation source.

In Example 4, the subject matter of any one or more of Examples 1-3 optionally include an optical fiber coupled to the feedback analyzer, the optical fiber configured to transmit the reflected signal to the feedback analyzer.

In Example 5, the subject matter of any one or more of Examples 1-4 optionally include a camera configured to generate an image of the reflected signal for the feedback analyzer.

In Example 6, the subject matter of any one or more of Examples 1-5 optionally includes, wherein the controller is configured to determine a composition of the target based upon the received reflected signal.

In Example 7, the subject matter of Example 6 optionally includes, wherein the target includes a calculi target, and wherein the controller is configured to, based upon the received reflected signal: determine a first composition of a first portion of the calculi target; and determine a second composition of a different second portion of the calculi target, the second composition being different from the first composition.

In Example 8, the subject matter of Example 7 optionally includes, wherein the surgical system is a surgical laser system, and the controller is configured to generate a control signal to the surgical laser system to: program a first laser setting or suggest a user to program the first laser setting to target the first portion of the calculi target; and program a second laser setting or suggest the user to program the second laser setting to target the second portion of the calculi target, the second laser setting being different from the first laser setting.

In Example 9, the subject matter of any one or more of Examples 6-8 optionally includes, wherein the controller is further configured to: communicate with a cloud computing device to access a cloud service therein including a machine learning based target recognition engine; and determine the composition of the target using the cloud service.

In Example 10, the subject matter of any one or more of Examples 1-9 optionally includes, wherein the surgical system is a surgical laser system, and wherein the controller is configured to generate a control signal to the surgical laser system to adjust a laser setting or suggest a user to adjust a laser setting based upon the received reflected signal.

In Example 11, the subject matter of any one or more of Examples 1-10 optionally includes, wherein the electromagnetic radiation includes one or more wavelengths between 10 nm to 400 nm.

In Example 12, the subject matter of any one or more of Examples 1-10 optionally includes the electromagnetic radiation that can include one or more wavelengths between 200 nm 1100 nm.

Example 13 is a method of feedback control of a surgical system, the method comprising: directing electromagnetic radiation at a target; receiving a reflected signal from the target in response to the electromagnetic radiation at the target; and generating a control signal to the surgical system to perform a predetermined operation based upon the received reflected signal.

In Example 14, the subject matter of Example 13 optionally includes: collecting spectroscopic data using a spectrometer based upon the received reflected signal; and generating the control signal to the surgical system to perform the predetermined operation based upon the spectroscopic data.

In Example 15, the subject matter of any one or more of Examples 13-14 optionally includes, wherein the predetermined operation comprises determining a composition of the target.

In Example 16, the subject matter of Example 15 optionally includes, wherein the target includes a calculi target, and wherein determining the composition of the target comprises: determining a first composition of a first portion of a calculi target; and determining a second composition of a different second portion of the calculi target, the second composition being different from the first composition.

In Example 17, the subject matter of Example 16 optionally includes the predetermined operation further comprising: programming a first laser setting or suggesting a user to program the first laser setting to target the first portion of the calculi target; and programming a second laser setting or suggesting the user to program the second laser setting to target the second portion of the calculi target, the second laser setting being different from the first laser setting.

In Example 18, the subject matter of any one or more of Examples 13-17 optionally includes: establishing a communication with a cloud computing device and accessing a cloud service therein including a machine learning based target recognition engine; and determining a composition of the target using the cloud service.

In Example 19, the subject matter of any one or more of Examples 13-18 optionally includes, wherein the predetermined operation comprises adjusting a laser setting or suggesting a user to adjust a laser setting based upon the received reflected signal.

Example 20 is a non-transitory program storage device readable by a machine, tangibly embodying a program of instructions executable by the machine for performing operations, the operations comprising: directing electromagnetic radiation at a target; receiving a reflected signal from the target in response to the electromagnetic radiation at the target; and generating a control signal to a surgical system to perform a predetermined operation based upon the received reflected signal.

In Example 21, the subject matter of Example 20, wherein the operations comprise: collecting spectroscopic data using a spectrometer based upon the received reflected signal; and generating the control signal to the surgical system to perform the predetermined operation based upon the spectroscopic data.

In Example 22, the subject matter of any one or more of Examples 20-21, wherein the control signal causes the surgical system to perform the predetermined operation including determining a composition of the target.

In Example 23, the subject matter of Example 22 optionally includes, wherein the control signal causes the surgical system to perform the predetermined operation including: determining a first composition of a first portion of a calculi target; and determining a second composition of a different second portion of the calculi target, the second composition being different from the first composition.

In Example 24, the subject matter of Example 23 optionally includes, wherein the control signal causes the surgical system to perform the predetermined operation including: programming a first laser setting or suggesting a user to program the first laser setting to target the first portion of the calculi target; and programming a second laser setting or suggesting the user to program the second laser setting to target the second portion of the calculi target, the second laser setting being different from the first laser setting.

In Example 25, the subject matter of any one or more of Examples 20-24 optionally includes the operations further comprising: establishing a communication with a cloud computing device and accessing a cloud service therein including a machine learning based target recognition engine; and determining a composition of the target using the cloud service.

In Example 26, the subject matter of any one or more of Examples 20-25 optionally includes, wherein the control signal causes the surgical system to perform the predetermined operation including adjusting a laser setting or suggesting a user to adjust a laser setting based upon the received reflected signal.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 10A-10B illustrate examples of feedback-controlled laser treatment systems.

DETAILED DESCRIPTION

Figure 1:
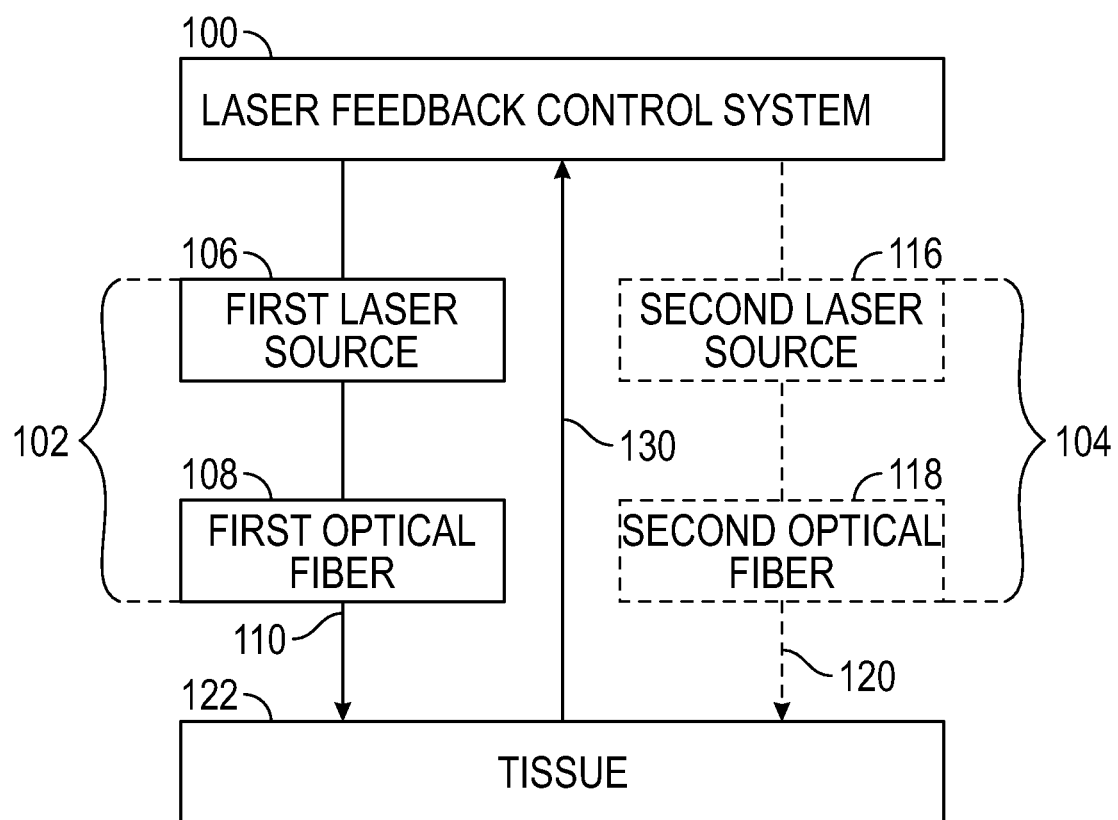
FIG. 1 illustrates a schematic of an exemplary laser treatment system including a laser feedback control system.

Described herein are systems, devices, and methods for systems, devices, and methods for identifying a target in a body using a spectroscopic feedback from the target. An exemplary surgical feedback control system comprises a feedback analyzer configured to receive a reflected signal from a target in response to electromagnetic radiation directed at a target, and a controller in operative communication with the feedback analyzer. The controller can generate a control signal to a surgical system to perform a predetermined operation based upon the received reflected signal, including determining a composition of the target, or programming a laser setting to direct laser energy to the target.

In endoscopic laser therapy, it is desirable to recognize different tissue, apply laser energy only to target treatment structures (e.g., cancerous tissue, or a particular calculus type), and avoid or reduce exposing non-treatment tissue (e.g., normal tissue) to laser irradiation. Conventionally, the recognition of a target treatment structure of interest is performed manually by an operator, such as by visualizing the target surgical site and its surrounding environment through an endoscope. Such a manual approach can lack accuracy at least in some cases, such as due to a tight access to an operation site that offers a limited surgical view, and may not determine composition of the target. Biopsy techniques have been used to extract the target structure (e.g., tissue) out of the body to analyze its composition in vitro. However, in many clinical applications, it is desirable to determine tissue composition in vivo to reduce surgery time and complexity and improve therapy efficacy. For example, in laser lithotripsy that applies laser to break apart or dust calculi, automatic and in vivo recognition of calculi of a particular type (e.g., chemical composition of a kidney or pancreobiliary or gallbladder stone) and distinguishing it from surrounding tissue would allow a physician to adjust a laser setting (e.g., power, exposure time, or firing angle) to more effectively ablate the target stone, while at the same time avoiding irradiating non-treatment tissue neighboring the target stone.

Conventional endoscopic laser therapy also has a limitation that tissue type (e.g., composition) cannot be continuously monitored in a procedure. There are many moving parts during an endoscopic procedure, and the tissue viewed at from the endoscope may change throughout the procedure. Because the conventional biopsy techniques require the removal of a tissue sample to identify the composition, they cannot monitor the composition of the tissue throughout the procedure. Continuous monitoring and recognition of structure type (e.g., soft or hard tissue type, normal tissue versus cancerous tissue, or composition of calculi structures) at the tip of the endoscope may give physicians more information to better adapt the treatment during the procedure. For example, if a physician is dusting a renal calculi that has a hard surface, but a soft core, continuous tissue composition information through the endoscope can allow the physician to adjust the laser setting based on the continuously detected stone surface composition, such as from a first setting that perform better on the hard surface of the stone to a second different setting that perform better on the soft core of the stone.

Some features as described herein may provide methods and apparatus that can identify the composition of various targets, for instance, in medical applications (e.g., soft or hard tissue) in vivo through an endoscope. This may allow the user to continuously monitor the composition of the target viewed through the endoscope throughout the procedure. This also has the ability to be used in combination with a laser system where the method may send feedback to the laser system to adjust the settings based on the composition of the target. This feature may allow for the instant adjustment of laser settings within a set range of the original laser setting selected by the user.

Some features as described herein may be used to provide a system and method that measures differences, such as the chemical composition of a target, in vivo and suggests laser settings or automatically adjusts laser settings to better achieve a desired effect. Examples of targets and applications include laser lithotripsy of renal calculi and laser incision or vaporization of soft tissue. In one example, three major components are provided: the laser, the spectroscopy system, and the feedback analyzer. In an example, a controller of the laser system may automatically program laser therapy with appropriate laser parameter settings based on target composition. In an example, the laser may be controlled based on a machine learning algorithm trained with spectroscope data. Additionally or alternatively, a user (e.g., a physician) may receive an indication of target type continuously during the procedure, and be prompted to adjust the laser setting. By adjusting laser settings and adapting the laser therapy to composition portions of a single calculus target, stone ablation or dusting procedure can be performed faster and in a more energy-efficient manner.

Some features as described herein may provide systems and methods for providing data inputs to the feedback analyzer to include internet connectivity, and connectivity to other surgical devices with a measuring function. Additionally, the laser system may provide input data to another system such as an image processor whereby the procedure monitor may display information to the user relevant to the medical procedure. One example of this is to more clearly identify different soft tissues in the field of view during a procedure, vasculature, capsular tissue, and different chemical compositions in the same target, such as a stone for example.

Some features as described herein may provide systems and methods for identifying different target types, such as different tissue types, or different calculi types. In some cases, a single calculus structure (e.g., a kidney, bladder, pancreobiliary, or gallbladder stone) may have two or more different compositions throughout its volume, such as brushite, calcium phosphate (CaP), dihydrate calcium oxalate (COD), monohydrate calcium oxalate (COM), magnesium ammonium phosphate (MAP), or a cholesterol-based or a uric acid-based calculus structure. For example, a target calculus structure may include a first portion of COD and a second portion of COM. According to one aspect, the present document describes a system and a method for continuously identifying different compositions contained in a single target (e.g., a single stone) based on continuously collection and analysis of spectroscopic data in vivo. The treatment (e.g., laser therapy) may be adapted in accordance with the identified target composition. For example, in response to an identification of a first composition (e.g., COD) in a target stone, the laser system may be programmed with a first laser parameter setting (e.g., power, exposure time, or firing angle, etc.) and deliver laser beams accordingly to ablate or dust the first portion. Spectroscopic data may be continuously collected and analyzed during the laser therapy. In response to an identification of a second composition (e.g., COM) different than the first composition in the same target stone being treated, the laser therapy may be adjusted such as by programing the laser system with a second laser parameter setting different from the laser parameter setting (e.g., difference power, or exposure time, or firing angle, etc.), and delivering laser beams accordingly to ablate or dust the second portion of the same target stone. In some examples, multiple different laser sources may be included in the laser system. Stone portions of different compositions may be treated by different laser sources. The appropriate laser to use may be determined by the identification of stone type.

Some features as described herein may be used in relation to a laser system for various applications where it may be advantageous to incorporate different types of laser sources. For instance, the features described herein may be suitable in industrial or medical settings, such as medical diagnostic, therapeutic and surgical procedures. Features as described herein may be used in regard to an endoscope, laser surgery, laser lithotripsy, laser settings, and/or spectroscopy.

FIG. 1 illustrates a schematic of an exemplary laser treatment system including a laser feedback control system 100 according to illustrative examples of the present disclosure. Example applications of the laser feedback control system 100 include integration into laser systems for many applications, such as industrial and/or medical applications for treatment of soft (e.g., non-calcified) or hard (e.g., calcified) tissue, or calculi structures such as kidney or pancreobiliary or gallbladder stones. For instance, systems and methods disclosed herein may be useful for delivering precisely controlled therapeutic treatment, such as ablation, coagulation, vaporization, and the like, or ablating, fragmenting, or dusting calculi structures.

Referring to FIG. 1, the laser feedback control system 100 may be in operative communication with one or more laser systems. While FIG. 1 shows the laser feedback system connected to a first laser system 102 and optionally (shown in dotted lines) to a second laser system 104, additional laser systems are contemplated within the scope of the present disclosure.

The first laser system 102 may include a first laser source 106, and associated components such as power supply, display, cooling systems and the like. The first laser system 102 may also include a first optical fiber 108 operatively coupled with the first laser source 106. The first optical fiber 108 may be configured for transmission of laser outputs from the first laser source 106 to the target tissue 122.

Figure 2A:
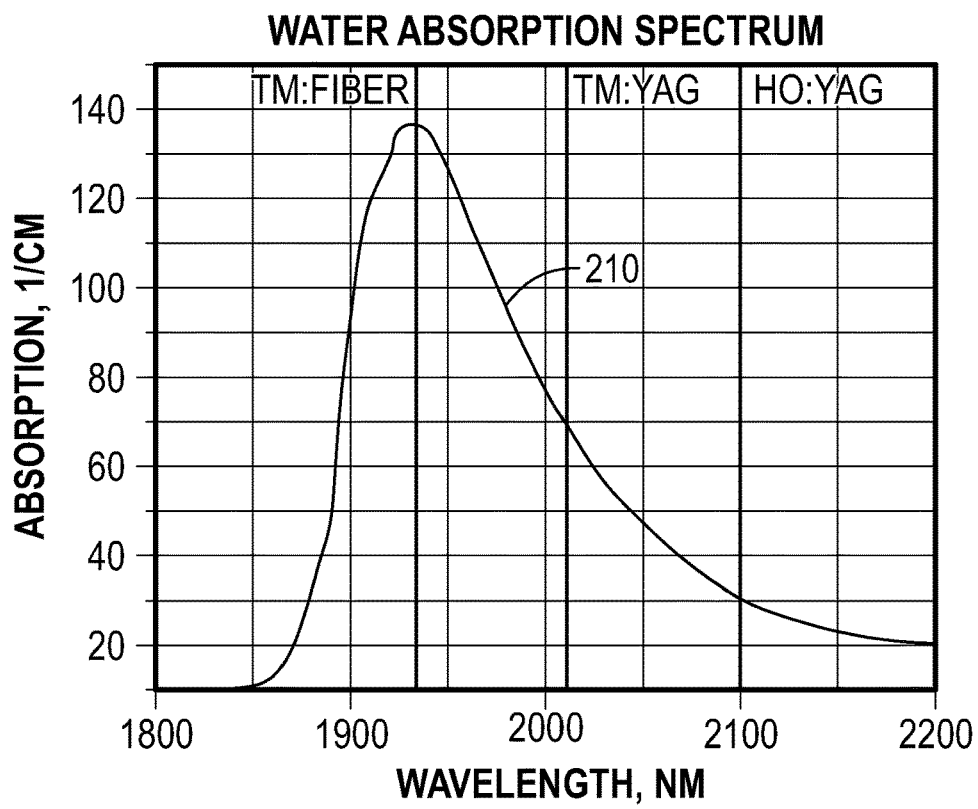
FIGS. 2A-2B illustrate examples of absorption spectra of different types of tissue including hemoglobin (Hb) and oxyhemoglobin ($HbO_2$).
Figure 2B:
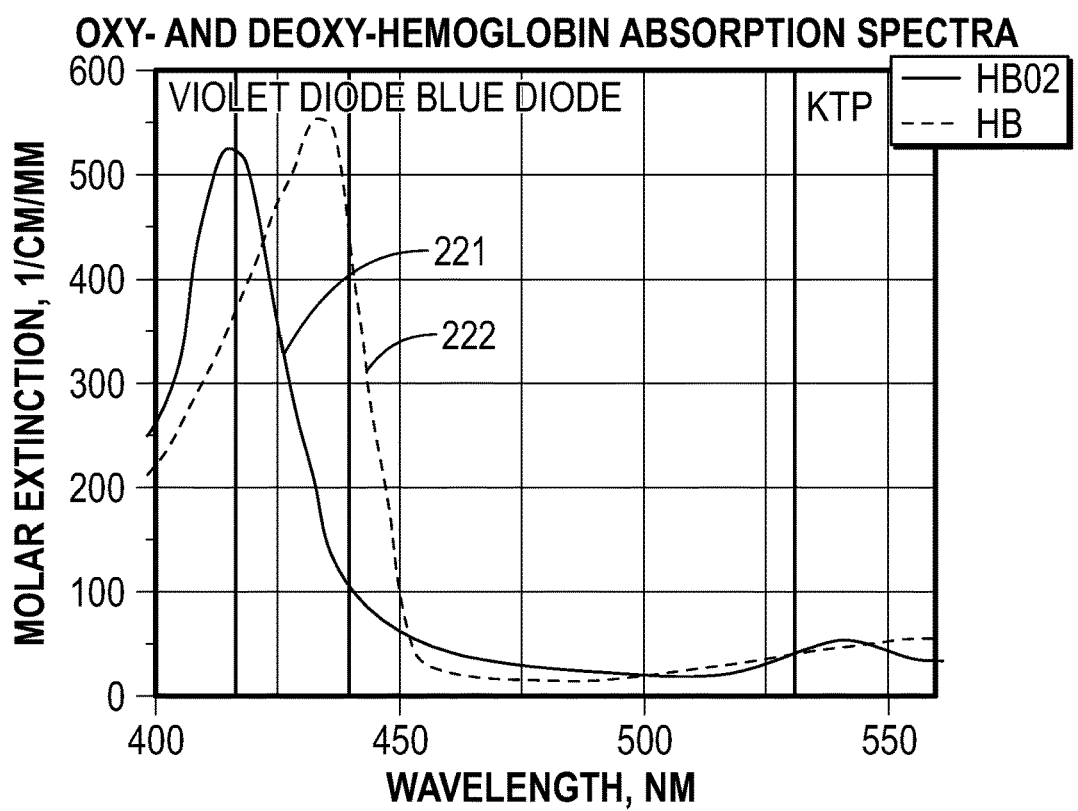

In one example, the first laser source 106 may be configured to provide a first output 110. The first output 110 may extend over a first wavelength range. According to some aspects of the present disclosure, the first wavelength range may correspond to a portion of the absorption spectrum of the target tissue 122. The absorption spectrum represents absorption coefficients at a range of laser wavelengths. FIG. 2A illustrates by way of example an absorption spectrum of water 210. FIG. 2B illustrates by way of example an absorption spectrum of oxyhemoglobin 221 and an absorption spectrum of hemoglobin 222. In such examples, the first output 110 may advantageously provide effective ablation and/or carbonation of the target tissue 122 since the first output 110 is over a wavelength range that corresponds to the absorption spectrum of the tissue.

For instance, the first laser source 106 may be configured such that the first output 110 emitted at the first wavelength range corresponds to high absorption (e.g., exceeding about 250 $cm^{-1}$) of the incident first output 110 by the tissue. In example aspects, the first laser source 106 may emit first output 110 between about 1900 nanometers and about 3000 nanometers (e.g., corresponding to high absorption by water) and/or between about 400 nanometers and about 520 nanometers (e.g., corresponding to high absorption by oxyhemoglobin and/or deoxy-hemoglobin). Appreciably, there are two main mechanisms of light interaction with a tissue: absorption and scattering. When the absorption of a tissue is high (absorption coefficient exceeding 250 $cm^{-1}$) the first absorption mechanism dominates, and when the absorption is low (absorption coefficient less than 250 $cm^{-1}$), for example lasers at 800-1100 nm wavelength range, the scattering mechanism dominates.

Various commercially available medical-grade laser systems may be suitable for the first laser source 106. For instance, semiconductor lasers such as InXGa1–XN semiconductor lasers providing the first output 110 in the first wavelength range of about 515 nanometers and about 520 nanometers, or between about 370 nanometers and about 493 nanometers may be used. Alternatively, infrared (IR) lasers such as those summarized in Table 1 below may be used.

TABLE 1

Example List of suitable IR lasers for the first laser source 106

| Laser | Wavelength λ (nm) | Absoprtion Coefficient $\mu_2$ (cm$^{-1}$) | Optical Penetration Depth δ (μm) |
|---|---|---|---|
| Thulium fiber laser: | 1908 | 88/150 | 114/67 |
| Thulium fiber laser: | 1940 | 120/135 | 83/75 |
| Thulium:YAG: | 2010 | 62/60 | 161/167 |
| Holmium:YAG: | 2120 | 24/24 | 417/417 |
| Erbium:YAG: | 2940 | 12,000/1,000 | 1/10 |

Referring to FIG. 1, the laser treatment system of the present disclosure may optionally include a second laser system 104. The second laser system 104, as mentioned previously, includes a second laser source 116 for providing a second output 120, and associated components, such as power supply, display, cooling systems and the like. The second laser system 104 may either be operatively separated from or, in the alternative, operatively coupled to the first laser source 106. In some examples, the second laser system 104 may include a second optical fiber 118 (separate from the first optical fiber 108) operatively coupled to the second laser source 116 for transmitting the second output 120. Alternatively, the first optical fiber 108 may be configured to transmit both the first output 110 and the second output 120.

In certain aspects, the second output 120 may extend over a second wavelength range, distinct from the first wavelength range. Accordingly, there may not be any overlap between the first wavelength range and the second wavelength range. Alternatively, the first wavelength range and the second wavelength range may have at least a partial overlap with each other. According to some aspects of the present disclosure, the second wavelength range may not correspond to portions of the absorption spectrum of the target tissue 122 where incident radiation is strongly absorbed (e.g., as illustrated in FIG. 2) by tissue that has not been previously ablated or carbonized. In some such aspects, the second output 120 may advantageously not ablate uncarbonized tissue. Further, in another example, the second output 120 may ablate carbonized tissue that has been previously ablated. In additional examples, the second output 120 may provide additional therapeutic effects. For instance, the second output 120 may be more suitable for coagulating tissue or blood vessels.

Figure 3A:
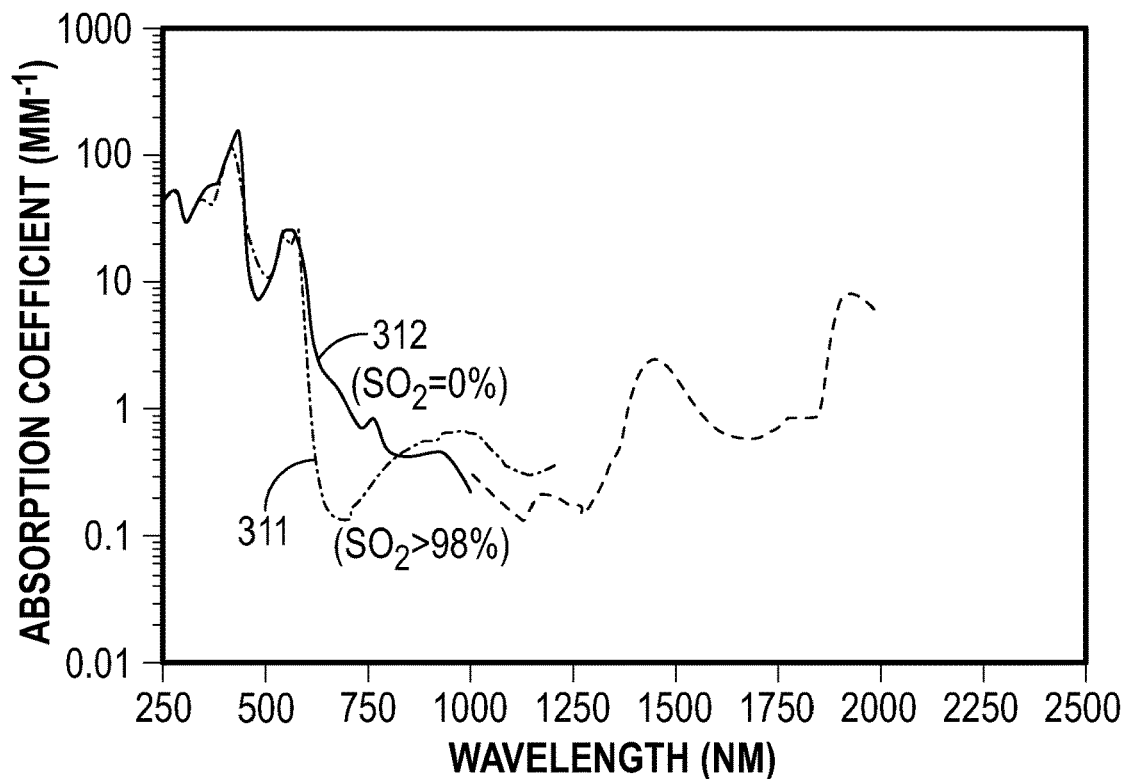
FIGS. 3A-3C illustrates examples of absorption spectra of different types of tissue including normal tissue and carbonized tissue, Hb, $HbO_2$, and melanin.
Figure 3B:
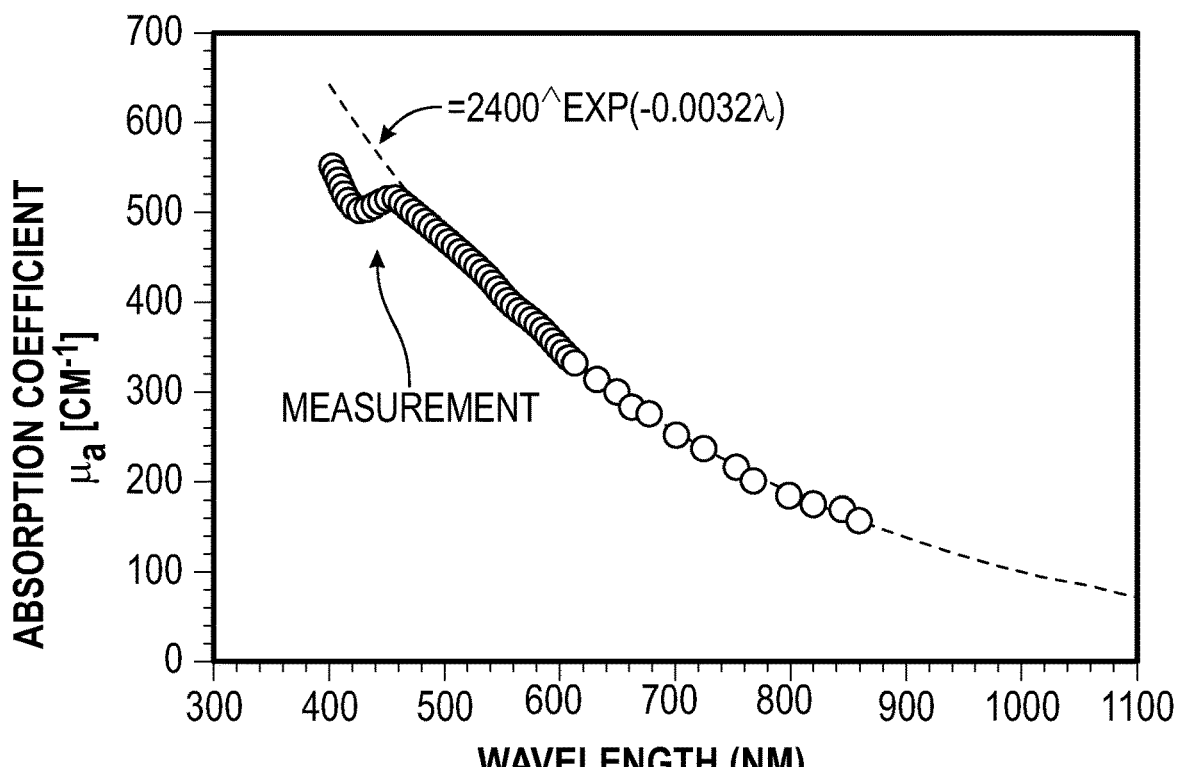
Figure 3C:
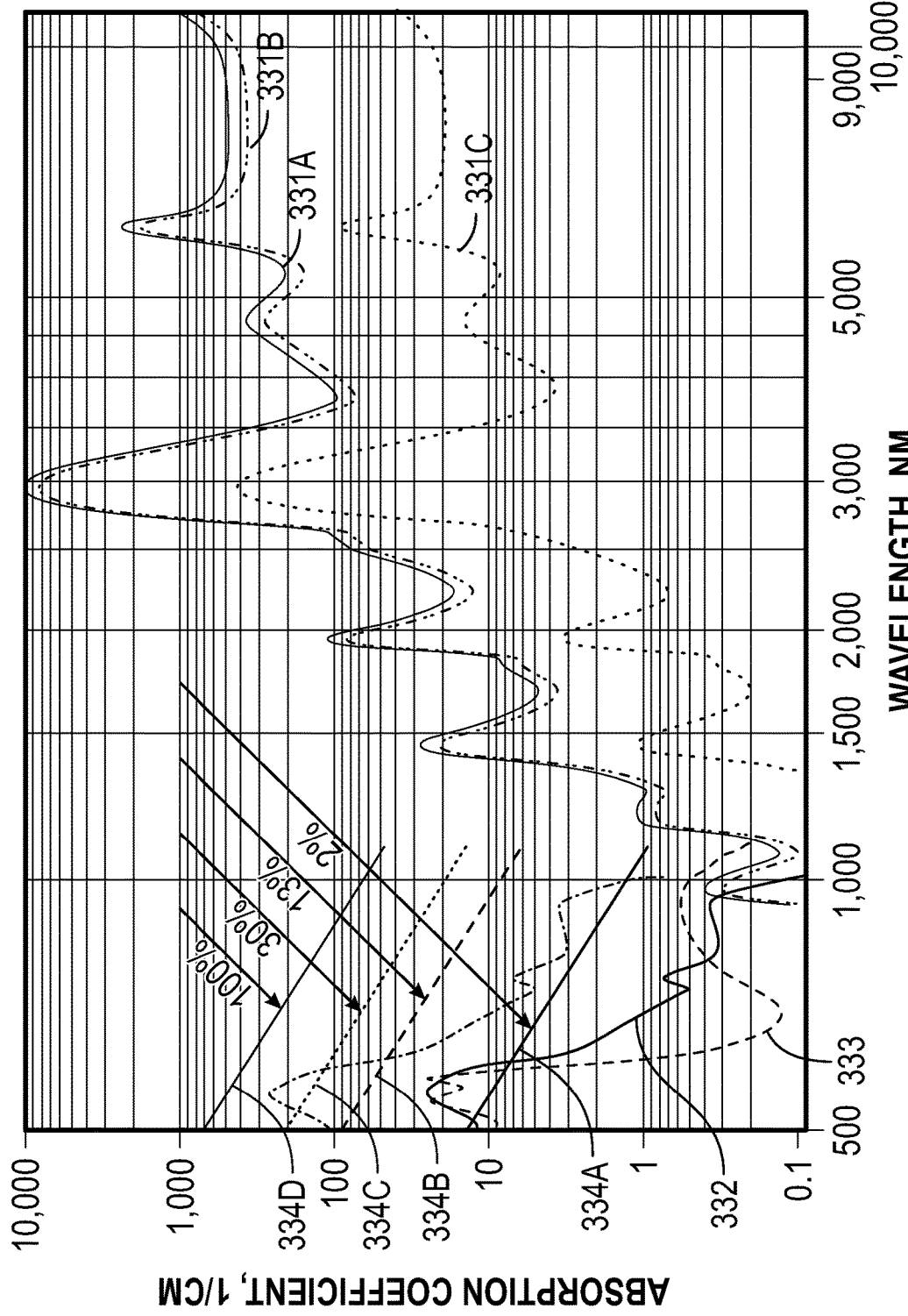

A laser emission may be highly absorbed by soft or hard tissue, stone, etc. By way of example, FIGS. 3A-3C illustrate absorption spectra of different tissue types. FIG. 3A illustrates absorption spectrum of normal tissue (prior to ablation) 311 and that of carbonized tissue (after ablation) 312, respectively. FIG. 3B illustrates that within a certain wavelength range (e.g., 450-850 nm), the absorption spectrum follows an exponential decay with the laser wavelength. (Source of data shown in FIGS. 3A and 3B: omlc.org/spectra/hemoglobin/). FIG. 3C illustrates optical absorption spectra measured in different media, including spectra for water 331A-331C (at 75%, 100%, and 4% concentration, respectively), spectra for hemoglobin (Hb) 332, spectra for oxyhemoglobin (HbO$_2$) 333, and spectra for melanin 334A-334D (for volume fractions of melanosomes in 2%, 13%, 30%, and 100%, respectively). (Source of data shown in FIG. 3C, www.americanlaserstudyclub.org/laser-surgery-education/). The wavelengths for water absorption are in the range of 1900 nm to 3000 nm. The wavelengths for oxyhemoglobin and/or oxyhemoglobin are in the range of 400 nm to 520 nm. Though many surgical lasers are highly absorbed in water or hemoglobin, inside a scope, there is limited media to absorb the water, which may be a reason for the inside of an endoscope may become damaged by laser energy.

Figure 4:
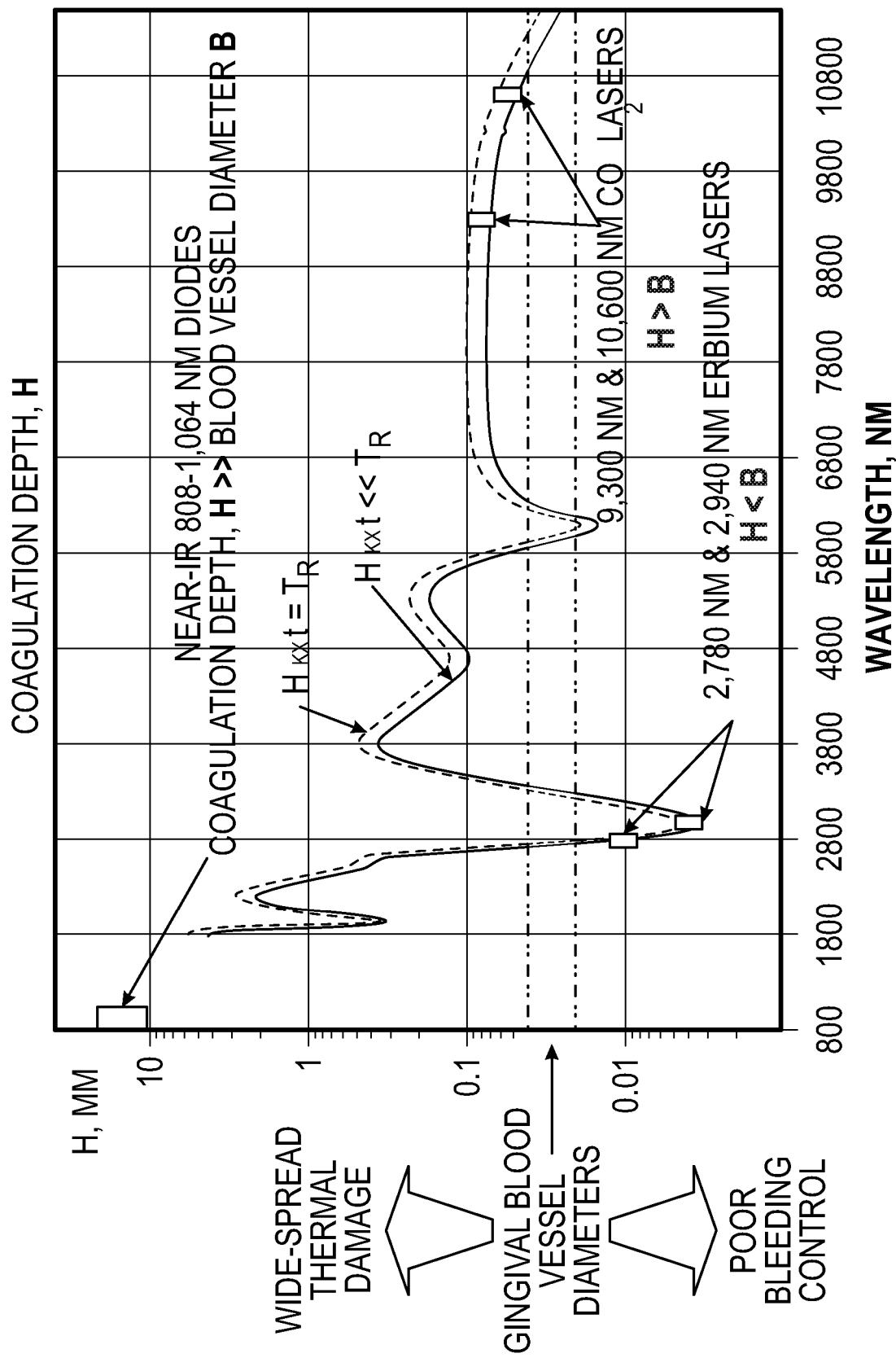
FIG. 4 is a diagram illustrating penetration depths of a laser output.

FIG. 4 illustrates the penetration depth of a laser output such as the second output 120. (Source of data shown in FIG. 4: www.americanlaserstudyclub.org/laser-surgery-education/). As seen therein, the second output 120 may be suitable for effective coagulation due to a penetration depth comparable to characteristic dimensions of a small capillary (e.g., between about 5 and about 10 μm). Furthermore, in certain examples, referring to FIGS. 3A and 3B, the second wavelength range may correspond to low absorption of the second output 120 by tissue that has not been carbonized, but high absorption by tissue that has been carbonized (e.g., by ablation of the first output 110). Appreciably, the spectral characteristics of the second output 120 correspond to high (e.g., greater than about 250 cm$^{-1}$) absorption of the incident second output 120 by carbonized tissue. Examples of suitable second laser sources include $Ga_xAl_{1-x}As$ with second output 120 in the second wavelength range of between about 750 nanometer and about 850 nanometer, or $In_xGa_{1-x}As$ with the second output 120 in the second wavelength range of between about 904 nanometer and about 1065 nanometer.

While two laser systems with partially overlapping spectra suitable for absorption by tissue (normal and/or carbonized) are described above, in alternative examples, instead of the second laser system 104, the first laser system 102 may provide the second output 120. In an example, the first laser system 102 may provide a first output 110 over the first wavelength range suitable for high absorption by "normal" tissue that has not been previously ablated (e.g., as illustrated in FIG. 2), and the second output 120 over the second wavelength range corresponding to low absorption by tissue prior to being carbonized, and/or more suitable for coagulation (e.g., as shown in FIGS. 3A and 3B). The first laser system 102 may provide additional outputs over additional wavelength ranges.

Figure 5:
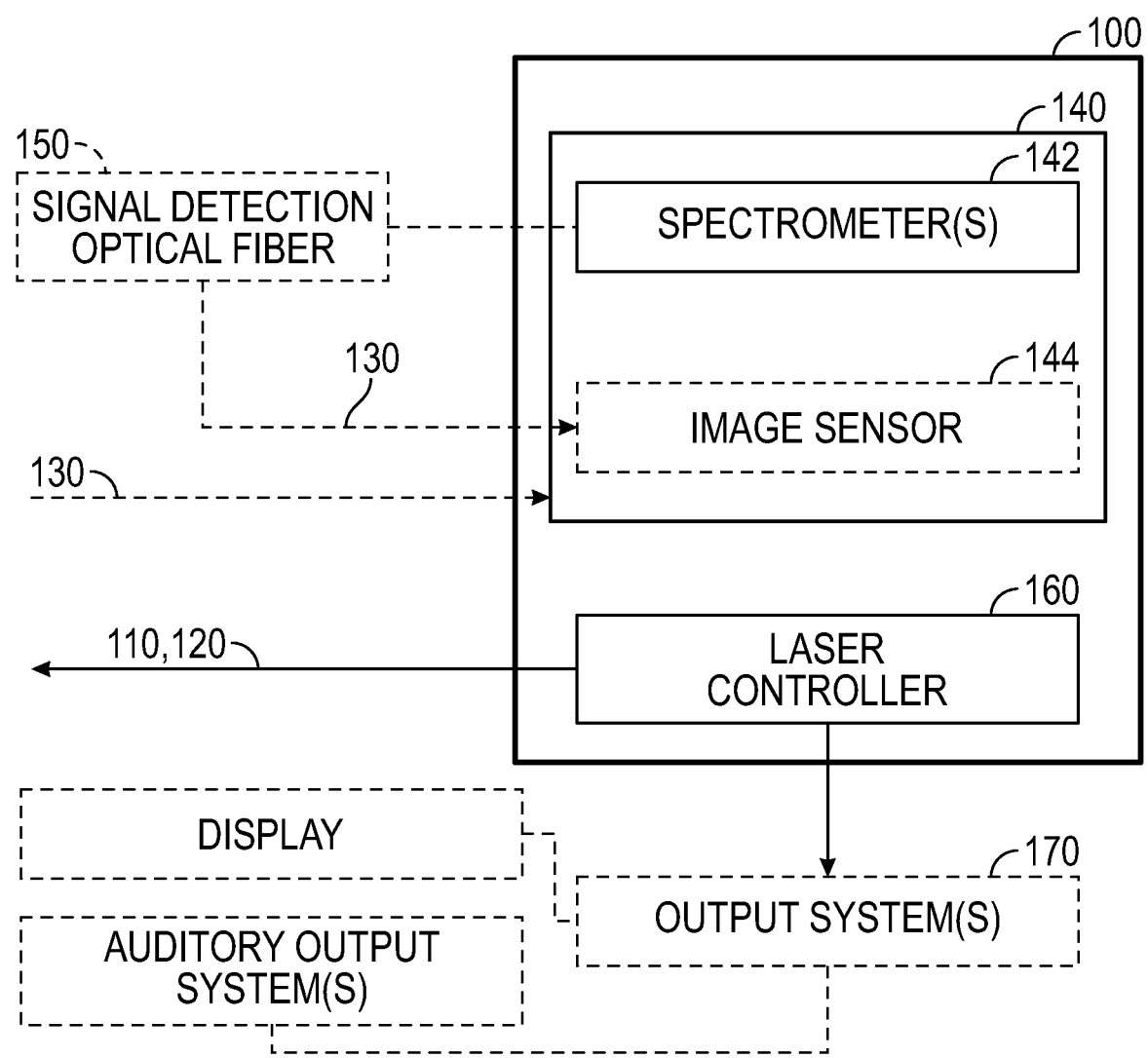
FIG. 5 is a block diagram illustrating a laser feedback control system for providing laser output.

Reference is again made to FIG. 1. According to example examples, the laser treatment system includes a laser feedback control system 100. Referring now to FIG. 5, as described previously, the laser feedback control system 100 may analyze feedback signals 130 from a target tissue 122 and control the first laser system 102 and/or the second laser system 104 to generate suitable laser outputs for providing a desired therapeutic effect. For instance, the laser feedback control system 100 may monitor properties of the target tissue 122 during a therapeutic procedure (e.g., ablation) to determine if the tissue was suitably ablated prior to another therapeutic procedure (e.g., coagulation of blood vessels). Accordingly, the laser feedback control system 100 may include a feedback analyzer 140.

With continued reference to FIG. 5, the feedback analyzer 140 may, according to one example, monitor spectroscopic properties of the tissue. Spectroscopic properties may include characteristics such as reflectivity, absorption index, and the like. Accordingly, the feedback analyzer 140 may include a spectroscopic sensor 142. The spectroscopic sensor 142 may include a Fourier Transform Infrared spectrometer (FTIR), a Raman spectrometer, a UV-VIS reflection spectrometer, a fluorescent spectrometer, and the like. The FTIR is a method used for routine, easy and rapid materials analysis. This technique has relatively good spatial resolution and gives information about the chemical composition of the material. The Raman spectroscopy has good accuracy in identifying hard and soft tissue components. As a high spatial resolution technique, it is also useful for determining distribution of components within a target. The UV-VIS reflection spectroscopy is a method that gathers information from the light reflected off an object similar to the information yielded from the eye or a color image made by a high resolution camera, but more quantitatively and objectively. The reflection spectroscopy offers information about the material since light reflection and absorption depends on its chemical composition and surface properties. It is also possible to get unique information about both surface and bulk properties of the sample using this technique. The reflection spectroscopy can be a valuable technique to recognize composition of hard or soft tissue. The fluorescent spectroscopy a type of electromagnetic spectroscopy that analyzes fluorescence from a sample. It involves using a beam of light, usually ultraviolet, that excites a material compound and causes the material compound to emit light, typically in visible or IR area. The method is applicable for analysis of some organic components such as hard and soft tissue.

The feedback analyzer 140 may include optionally, an imaging sensor 144 (e.g., CCD or CMOS camera sensitive in ultraviolet (UV), visible (VIS) or infrared (IR) wavelengths) in an example. In some examples, the spectroscopic sensor 142 may include more than a single type of spectrometer or imaging camera listed herein to enhance sensing and detection of various features (e.g., carbonized and non-carbonized tissue, vasculature, and the like).

In some examples, the spectroscopic sensor 142 (also known as spectrometer) may include any of the spectrometers listed herein, and may additionally rely on imaging capabilities of an endoscope used during a therapeutic procedure. For instance, an endoscope may be used for visualizing an anatomical feature during a therapeutic procedure (e.g., laser ablation of a tumor). In such cases, the imaging capabilities of the endoscope may be augmented by the spectroscopic sensor 142. For example, conventional endoscopes may provide narrow band imaging suitable for enhanced visualization of anatomical features (e.g., lesions, tumors, vasculature, and the like). By combining the spectroscopic sensor 142 with endoscopic imaging (white light and/or narrow band imaging), may increase detection of tissue properties, such as level of carbonization, to precisely control the delivery of therapeutic treatment.

Referring again to FIG. 5, the spectroscopic sensor 142 may be operatively coupled to a signal detection optical fiber 150. In such examples, the signal detection optical fiber 150 may have optical properties suitable for transmission of spectroscopic signals from the tissue to the spectroscopic sensor 142. Alternatively, the spectroscopic sensor 142 may be operatively coupled to the first optical fiber 108 of the first laser system 102 and/or the second optical fiber 118 of the second laser system 104 and thereby detect spectroscopic signals via the first optical fiber 108 and/or the second optical fiber 118.

With continued reference to FIGS. 1 and 5, the laser feedback control system 100 includes a laser controller 160 in operative communication with each of the spectroscopic sensor 142, the first laser system 102, and optionally the second laser system 104. The laser controller 160 may control one or more laser systems (e.g., the first laser system 102, the second laser system 104, and/or any additional laser systems) operatively connected thereto according to one or more control algorithms described herein to control the laser outputs from the one or more laser systems to produce a desired therapeutic effect in the target tissue 122.

The laser controller 160 may include processors, such as microprocessors, digital signal processors (DSPs), application specific integrated circuits (ASICs), field programmable gate arrays (FPGAs), or any other equivalent integrated or discrete logic circuitry, as well as any combinations of such components for performing one or more of the functions attributed to the laser controller 160. Optionally, the laser controller 160 may be coupled by wired or wireless connections to the spectroscopic sensor 142 and one or more laser systems (e.g., the first laser system 102, the second laser system 104, and optional laser systems not illustrated herein).

The laser controller 160 may communicate with the feedback analyzer 140 (e.g., over wired or wireless connections) to receive one or more feedback signals from the feedback analyzer 140. The laser controller 160 may determine one or more properties of the target tissue 122 based on the feedback signal(s), as will be described further herein. For instance, the laser controller 160 may compare the amplitude of the feedback signals to present minimum and maximum amplitudes, and determine a property (e.g., carbonized, coagulated, etc.) of the tissue.

In some examples, the feedback analyzer 140 may continuously monitor the target tissue 122 and continuously communicate with the laser controller 160 to provide feedback signals. Accordingly, the laser controller 160 may continue maintaining the laser systems in one or more states until a change in amplitude of the feedback signal is detected. When a change in amplitude of the spectroscopic signal is detected, the laser controller 160 may communicate with the one or more laser systems and change their state(s) to deliver a desired therapeutic effect. Alternatively, or in addition, the laser controller 160 may communicate with an operator (e.g., healthcare professional), and display one or more output(s) via one or more output system(s) indicative of the feedback signal, and may, optionally, instruct the operator to perform one or more treatment procedures with the first laser system and/or the second laser system to deliver a desired therapeutic effect.

In illustrative examples described herein, the laser controller 160 may control the one or more laser systems by changing the state of the laser systems. According to an aspect, the laser controller 160 may independently control each laser system. For instance, the laser controller 160 may send a distinct control signal to each laser system to control each laser system independently of the other laser systems. Alternatively, the laser controller 160 may send a common signal to control one or more laser systems.

In some examples, each of the laser systems may be associated with two distinct states: a first state wherein the laser system generates a laser output, and a second state where a laser system does not generate a laser output. For instance, the first laser system 102 may have a first state where a first output 110 (e.g., over the first wavelength range) is generated, and a second state where the first output 110 is not generated. Similarly, the second laser system 104 may have a first state where a second output 120 (e.g., over the second wavelength range) is generated, and a second state where the second output 120 is not generated. In such examples, the laser controller 160 may control the one or more laser system by sending control signals that change the state of the laser system from the first state to the second state, or from the second state to the first state. Further, optionally, each laser system may have additional states, for instance, a third state where a laser output over different wavelength range is generated. Accordingly, additional control signals may be sent by the laser controller 160 to the laser system(s) to change their states from their current state to one or more additional states (e.g., first state to third state, second state to third state, third state to first state, and third state to second state) to generate laser outputs that provide a desired therapeutic effect.

Example Laser System Control Algorithms

Figure 6:
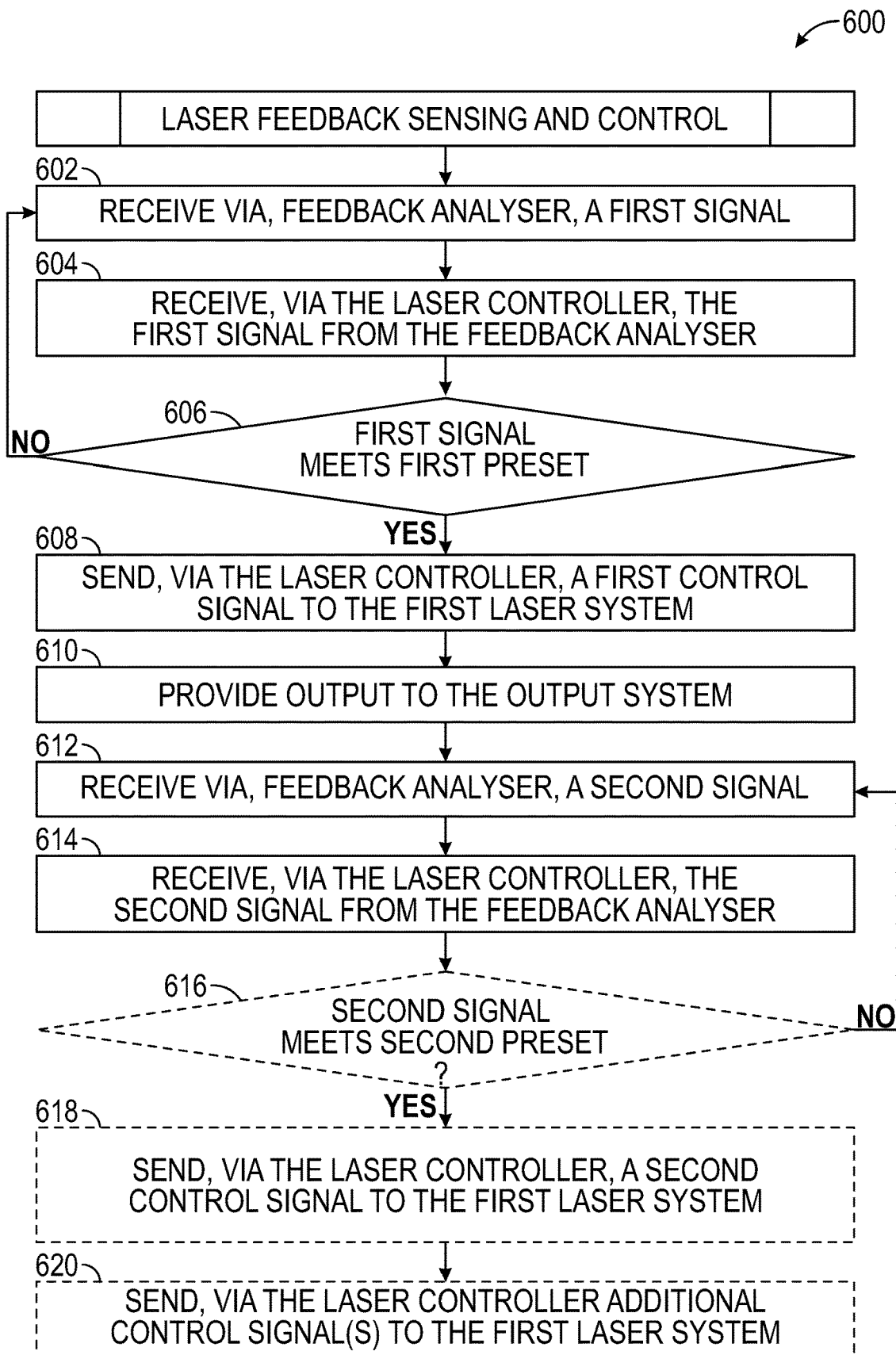
FIGS. 6-7 are flow diagrams illustrating examples of algorithms for controlling one or more laser systems based on the feedback generated by a laser feedback control system.
Figure 7:
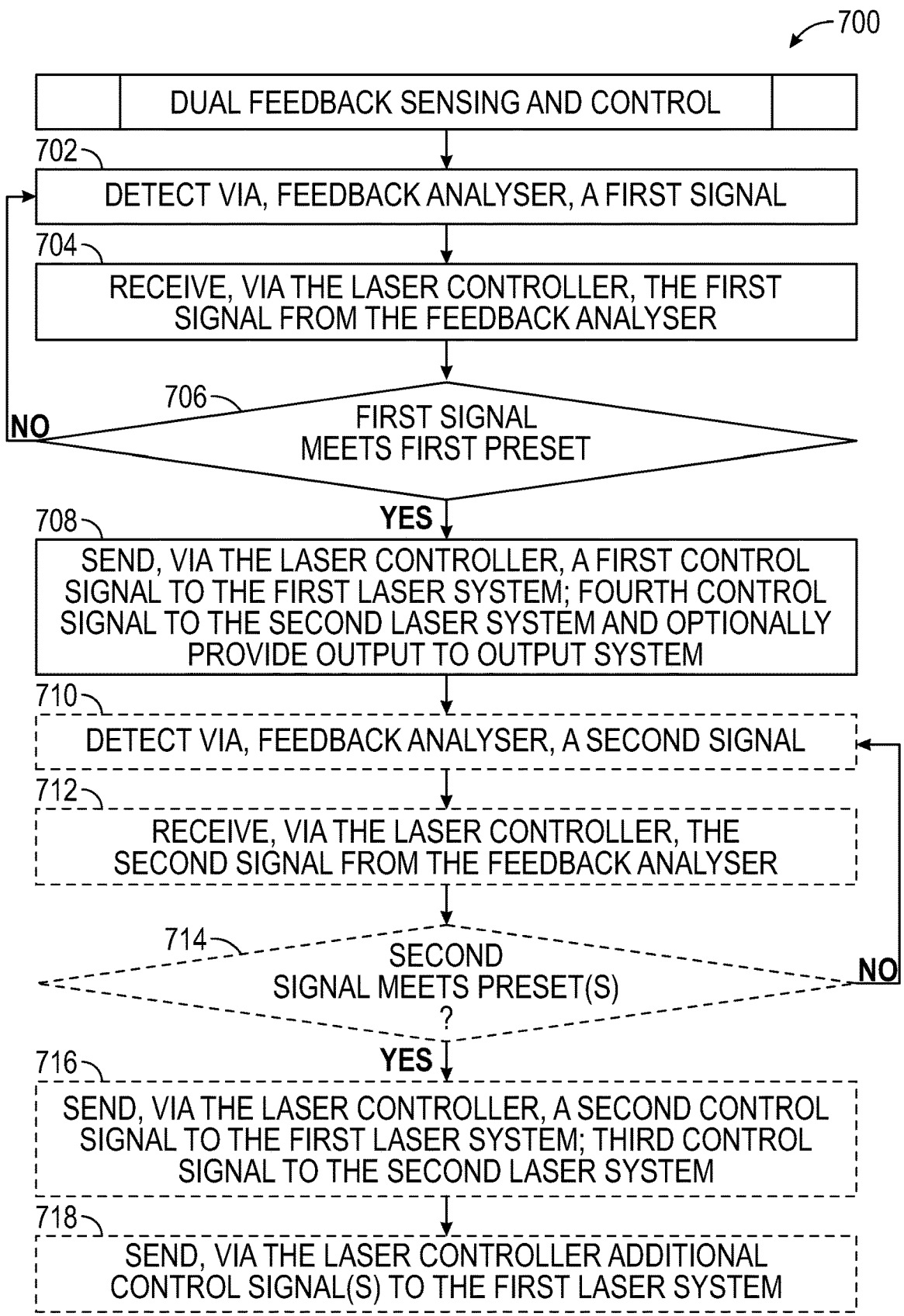

FIGS. 6 and 7 are flow diagrams illustrating examples of algorithms for controlling one or more laser systems using the laser feedback control system 100 according to some examples as described in this disclosure. In accordance with control algorithm 600 as shown in FIG. 6, at step 602, a first signal (e.g., spectroscopic signal) may be detected by the feedback analyzer 140 (e.g., spectroscopic sensor 142 or imaging sensor 144). At step 604, the laser controller 160 may receive the first signal from the feedback analyzer 140. The first signal may correspond to a first property. At step 606 the laser controller 160 may determine whether the first signal generally equals a first preset value. For example, the laser controller 160 may compare the amplitude of the first signal to a target value or preset extrema (e.g., maximum or minimum amplitudes) and determine the first property of the target tissue 122. The first property may be indicative of tissue's characteristics after receiving a therapeutic treatment (e.g., ablated or carbonized tissue). The laser controller 160 may determine based on the first property (comparison between the first signal and the first preset value) that the first desired therapeutic effect has been obtained, and may, at step 608 send a first control signal to the first laser system 102 to change from a first state of the first laser system 102 to a second state the first laser system 102. According to an example, this may result in the first laser system 102 no longer generating the first output 110, as a result of satisfactory delivery of therapeutic effect (e.g., ablation). Alternatively, if at step 606, it is determined that the first signal does not generally equal the first preset (not sufficient ablation), the laser controller may not send any control signals, and the feedback analyzer may continue monitoring the first signal.

Optionally, at step 612, the feedback analyzer 140 may receive a second signal, distinct from the first signal. The second signal may be indicative of the first property of the target tissue having a second preset value. For instance, the amplitude of reflected light from the tissue may be different in the second signal than in the first signal. At optional step 614, the second signal may be received by the laser controller 160. At optional step 616, the laser controller 160 may determine whether the second signal generally equals the second preset. For instance, the second signal (e.g., a spectroscopic signal or image) may be indicative of the target tissue 122 not being carbonized by absorption of the first output 110 (e.g., measured signal amplitude being less than a preset maximum amplitude of a spectroscopic signal or image of ablated tissue). In some instances, such a condition may be indicative of inadequate ablation or other unsatisfactory therapeutic effect, and it may be desirable to continue delivering laser output so that the tissue can be ablated. Accordingly, at optional step 618, the laser controller 160 may communicate with the first laser system 102 to send a second control signal. The second control system may, in an maintain the first laser system 102 in the first state (e.g., to continue delivering the first output 110). Alternatively, if the first laser system is in the second state (e.g., off), at optional step 620, the second control signal may change the state of the first laser system to the first state (e.g., on), for instance, to continue delivering additional ablation to the target tissue.

At optional step 620, after the laser controller 160 determines satisfactory delivery of the therapeutic condition, the laser controller 160 may perform additional control operation to deliver additional laser outputs (e.g., at a different wavelength) to deliver an additional therapeutic effect(s).

FIG. 7 illustrates a control algorithm for control of a dual laser system. Algorithm 700 may be suitable in instances where the laser controller 160 is in operative communication with two or more laser systems. In some such examples, the first laser system 102 may be configured for delivering a first output 110 (e.g., in a first wavelength range), and the second laser system 104 may be configured for delivering a second output 120 (e.g., in a second wavelength range different from the first wavelength range) as described previously. Control algorithm 700 may control the first laser system 102, the second laser system 104 and optionally, additional laser systems.

In accordance with control algorithm 700, at step 702, a first signal (e.g., spectroscopic signal or image) may be detected by the feedback analyzer 140. At step 704, the laser controller 160 may receive the first signal from the feedback analyzer 140. At step 706 the laser controller 160 may determine whether the first signal is generally equal to a first preset value (such as within a specified tolerance margin of the first preset). For example, the laser controller 160 may compare the amplitude of the first signal to a target value or preset extrema (e.g., maximum or minimum amplitudes) and determine the first property of the target tissue 122. The first property may be indicative of tissue's characteristics after receiving a therapeutic treatment (e.g., ablated or carbonized tissue). The laser controller 160 may determine based on the first property meeting the target value or preset criteria that the desired therapeutic effect has been obtained, and may, at step 708 send a first control signal to the first laser system 102 to change from a first state of the first laser system 102 to a second state the first laser system 102. For example, the laser controller 160 may determine that ablation has been satisfactory based on reflected light from the ablated tissue, and send a first control signal to the first laser system to turn the first laser system to an OFF state. Alternatively, in illustrative examples, the laser controller 160 may provide an output to an operator (e.g., healthcare professional) to indicate that the desired therapeutic effect has been reached, and/or indicate to the operator to change the state of the first laser system to "OFF" state.

Figure 8:
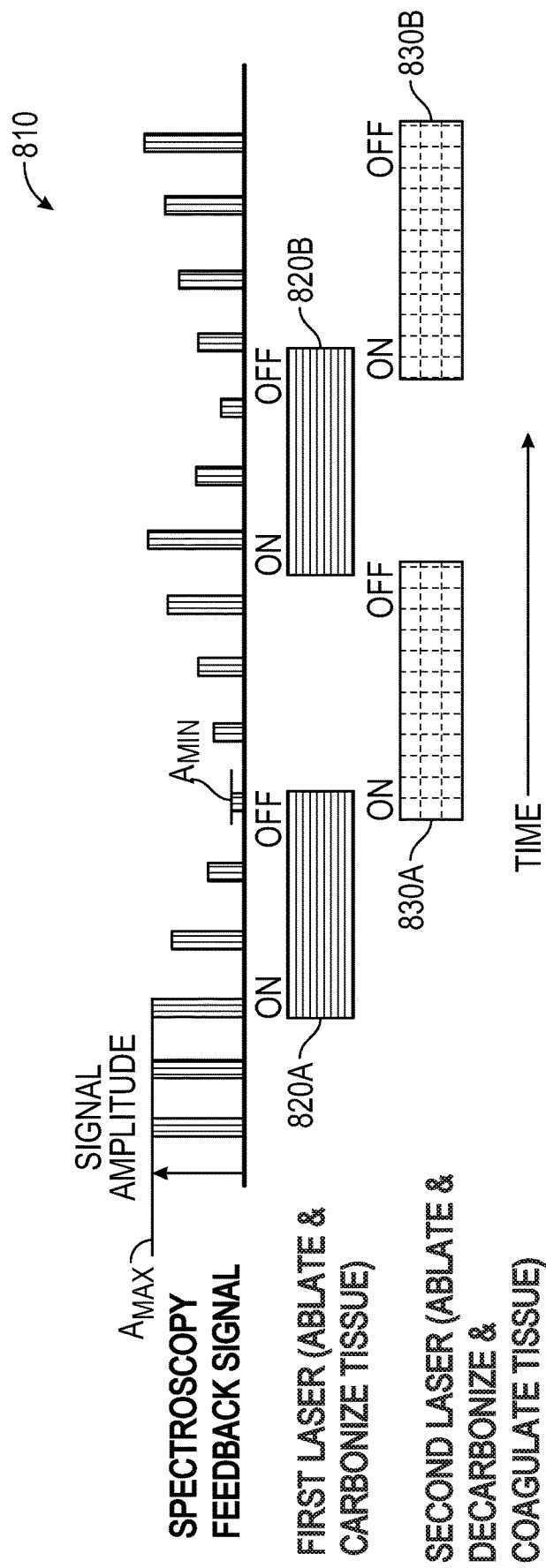
FIG. 8 illustrates a timing diagram of an exemplary dual laser system providing tissue ablation and coagulation using two optical wavelengths.

At step 708, the laser controller 160 may also send a fourth signal to a second laser system 104 to change from a second state of the second laser system 104 to a first state of the second laser system 104. For instance, the second laser system 104 may be more suitable for ablating carbonized tissue. Accordingly, upon detecting that the tissue has been adequately carbonized (e.g., at step 708), the laser controller 160 may, in some instances, send the first control signal to switch off the first laser system 102, and send the fourth control signal to switch on the second laser system 104. An example timing diagram of the states of the first laser system and the second laser system is shown in FIG. 8.

In some examples, the first control signal and the fourth control signal may be sent simultaneously. Alternatively, the first control signal and the fourth control signal may be sent in succession.

Returning to FIG. 7, at optional step 710, the feedback analyzer 140 may detect a second signal (e.g., spectroscopic signal or image), distinct from the first signal. For instance, the second signal may be indicative of the target tissue 122 not being carbonized by absorption of the first output 110 (e.g., measured signal amplitude being greater than a preset maximum amplitude of a spectroscopic signal of ablated tissue). In some instances, such a condition may be indicative of inadequate ablation or other unsatisfactory therapeutic effect, and it may be desirable to continue delivering laser output so that the tissue can be ablated. At optional step 712, the laser controller may receive the second signal, and at optional step 714, compare the second signal to a second preset value. If the second signal is generally equal to the second preset value (such as within a specified tolerance margin of the second preset), at optional step 716, the laser controller 160 may send the second control signal to the first laser system and the third control signal to the second laser system. An example timing diagram of the states of the first laser system and the second laser system is shown in FIG. 8.

The second control signal may, in some examples, change the first laser system from the second state (e.g., OFF) to the first state (e.g., ON). Alternatively, if the first laser system is in the first state (e.g., ON), the second control signal may maintain the first laser system 102 in the first state (e.g., to continue delivering the first output 110). Optionally, at step 716, the laser controller 160 may send a third control signal to the second laser system 104, thereby changing the second laser system 104 from the first state (e.g., ON) of the second laser system 104 to the second state (e.g., OFF) of the second laser system 104, if the second laser system 104 is in its first state. Alternatively, the third control signal may maintain the second laser system 104 in the second state (e.g., OFF) if the second laser system is in the second state.

According to some examples, the first state of each of the first laser system 102 and the second laser system 104 may correspond to generation of a first output 110 by the first laser source 106 and a second output 120 by a second laser source 116 respectively. Accordingly, the first state of each of the first laser system 102 and the second laser system 104 may represent an "on" state. In some such examples, the second state of each of the first laser system 102 and the second laser system 104 may correspond to an "off" state.

Referring to FIG. 5, the laser feedback control system 100 may include one or more output systems 170. The one or more output systems 170 may communicate with and/or deliver signals to users and/or to other systems such as an irrigation suction/pumping system used for a therapeutic treatment, or an optical display controller, or other systems. The output system 170 may include a display 172 in some examples. The display 172 may be a screen (e.g., a touchscreen), or in the alternative, may simply be a visual indicator (e.g., LED lights of one or more colors). In additional examples, the output system 170 may include auditory output systems 174 capable of providing auditory signals (e.g., speakers, an alarm system and the like). The output system(s) 170 may provide one or more outputs (e.g., LED lights of a first color, a first message on the screen, an alarm sound of a first tone) to indicate that a desired therapeutic effect has been achieved. The output(s) may be provided, for instance, at step 610, and optionally, at step 620. In further optional examples, the output system(s) 170 may provide one or more different outputs when desired therapeutic effects have not been achieved. For instance, output system(s) 170 may provide one or more outputs (e.g., LED lights of a second color, a second message on the screen, an alarm sound of a second tone) to indicate that a desired therapeutic effect has not been achieved. Such outputs may prompt the operator (a health care professional) to take one or more steps (e.g., perform additional treatment steps using the one or more laser systems to provide additional laser outputs).

FIG. 8 illustrates a timing diagram of a dual laser system with a laser feedback control system 100 according to an example of delivering tissue ablation and coagulation by utilizing two optical wavelengths. However, as described previously, the laser feedback control system 100 may be utilized with a single or multiple optical wavelength systems to optimize the delivery of laser therapy or other types of therapeutic effects to target tissues 122. The therapeutic effects may be delivered in any sequence, including simultaneously. Alternatively, the therapeutic effects may be delivered at different times.

According to an example, laser energy from a first laser system 102 and the second laser system 104 may be delivered to a target (e.g., tissue surface), such as continuously in an example. The first and the second laser systems may deliver respective laser energy via the same optical fiber. Alternatively, the first and the second laser systems may deliver respective laser energy via respective distinct optical fibers. Optical feedback signals 810 with amplitude $A_{max}$ are reflected from the tissue surface and may be detected and analyzed by the feedback analyzer 140. The first and second laser systems may alternate their respective operating states (e.g., an ON state or an OFF state). As illustrated in FIG. 8, the first laser system 102 may be switched to its first state, or maintained at its first state (e.g., ON) 820A, while the second laser system 104 may be switched to or maintained at a second state (e.g., OFF). The first laser may be used to ablate and carbonize tissue. During operation of the first laser system 102, the first signal may be received by the laser controller 160, and may indicate high absorption by tissue until its amplitude reduces to a threshold level, $A_{min}$. The wavelength of the output from the first laser system 102 can be in a first wavelength range in an absorption spectrum of the target, such as a wavelength suitable for effective carbonization of the target tissue. The tissue has high absorption of laser energy. In an example, the first laser output is in a UV-VIS or deep infrared wavelength range.

The laser controller 160 may then change the state of the laser systems, such that the first laser system 102 is in the second state (e.g., an OFF), and the second laser system 104 is in the first state (e.g., ON) 830A. The output from the second laser system 104 may be highly absorbed by the carbonized tissue so that the carbonized tissue is ablated, effectively removing the carbonization. The wavelength of the output from the second laser system 104 can be in a second wavelength range in an absorption spectrum of the target. The second wavelength range can be different from the first wavelength range of the output from the first laser system 102. The wavelength of the output from the second laser system 104 may also be suitable for effective coagulation. In an example, the second laser output is in an infrared wavelength range (e.g., 100-300 μm). Due to decarbonization process the amplitude of the signal (e.g., second signal) returns close to the initial level, $A_{max}$. The laser controller 160 may accordingly change the state of the lasers, such that the first laser system 102 is in the first state (e.g., ON), and the second laser system 104 is in the second state (e.g., OFF). The process may be repeated, such that the first laser system 102 and the second laser system 104 are repeatedly switched to their ON states 820B and 830B respectively in an alternate fashion as illustrated in FIG. 8, until the desired tissue ablation and/or coagulation is achieved. In some examples, the optical feedback signals 810 as discussed herein may be provided to an electrosurgical system that can controllably adjust and optimize electrosurgical energy different than laser energy.

Example Endoscopic System with Target Identification

FIGS. 9-11 demonstrate how the target composition analysis may be performed entirely within an endoscope. The target composition analysis may be performed via spectroscopy through the laser fiber and potentially a camera on the distal tip of a digital endoscope.

Figure 9A:
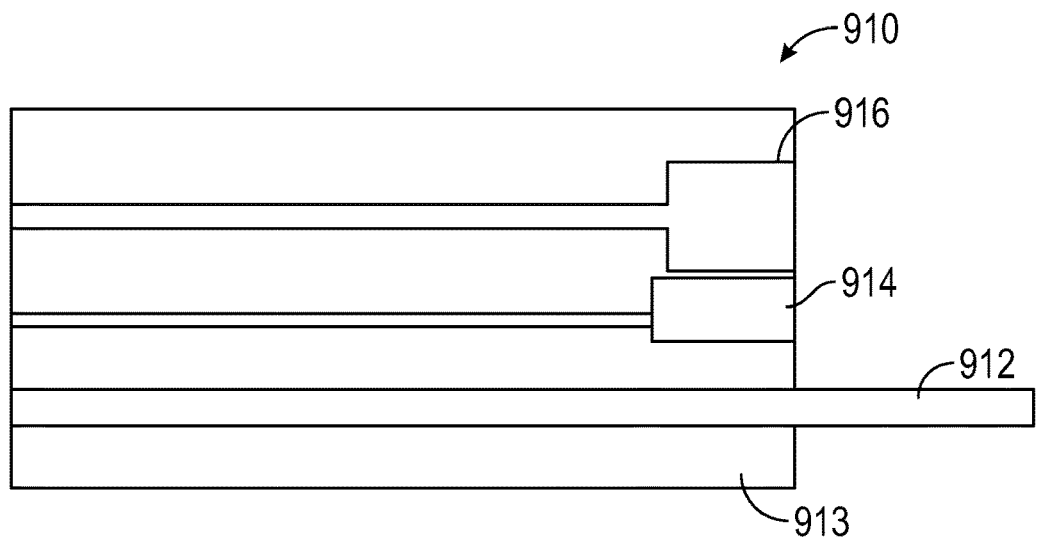
FIGS. 9A-9B illustrate an example of an endoscope with a laser fiber inserted.
Figure 9B:
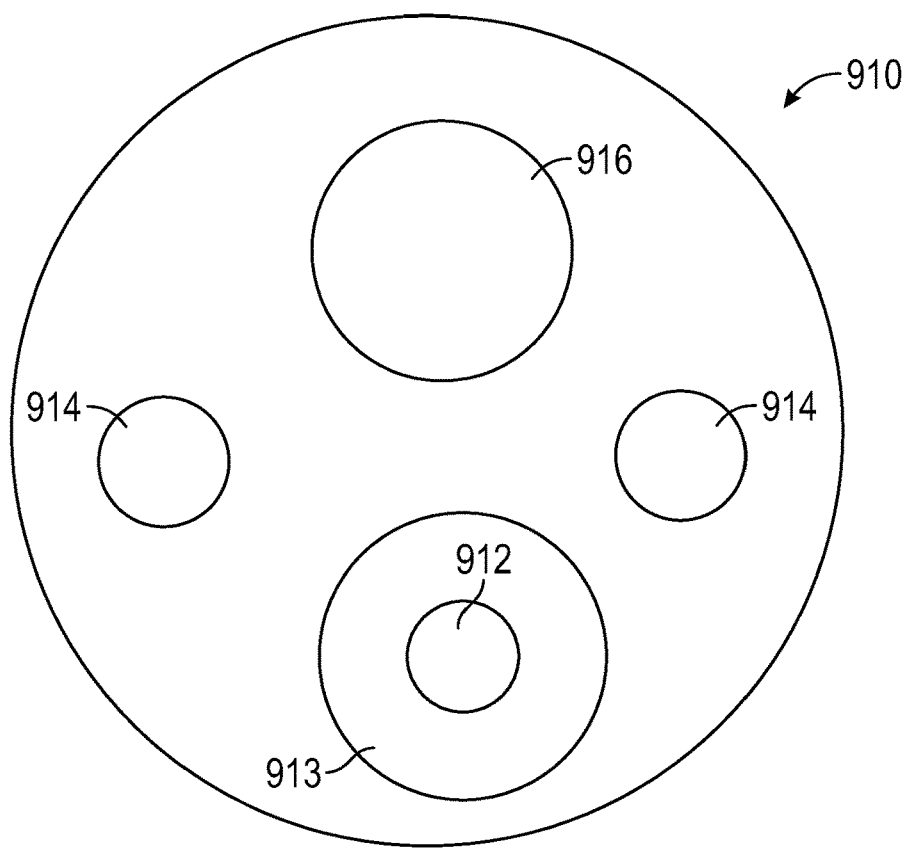

FIGS. 9A-9B illustrates an example of an endoscope with a laser fiber inserted. An elongate body portion of an exemplary endoscope 910 encompasses various components, including a laser fiber 912, an illumination source 914, and a camera 916. The laser fiber 912 is an example of the optical pathway 108 of the laser system 102 or the laser system 202. The laser fiber 912 may extend along a working channel 913 within the elongate body of the endoscope 910. In some examples, the laser fiber 912 may be separate from the endoscope. For example, the laser fiber 912 may be fed along a working channel of the endoscope prior to use, and retrieved from a working channel of the endoscope after use.

The illumination source 914 may be a part of a visualization system that allows an operator to visualize the target structure (e.g., tissue or calculi structures). Examples of the illumination source can include one or more LEDs configured to emit light distally away from the distal end of the elongate body of the endoscope to illuminate the field of the target structure. In an example, the illumination source 914 may emit white light to illuminate the target structure. White light can allow the practitioner to observe discolorations or other color-based effects on the calculi or on the tissue proximate the distal end of the body of the endoscope. In an example, the illumination source 914 may emit blue light to illuminate the target structure. Blue light can be well-suited to show thermal tissue spread and thereby detect damage in the tissue. Other colors and/or color bands, such as red, amber, yellow, green, or others, can also be used.

The camera 916 is a part of the visualization system. The camera 916 is an example of the imaging sensor 244. The camera 916 can capture a video image or one or more static images of the illuminated target structure and the surrounding environment. The video image can be in real-time, or nearly real-time with a relatively short latency for processing, so that the practitioner can observe the target structure as the practitioner manipulates the endoscope. The camera 916 can include a lens and a multi-pixel sensor located at a focal plane of the lens. The sensor can be a color sensor, such as a sensor that provides intensity values for red light, green light, and blue light for each pixel in the video image. The circuit board can produce a digital video signal representing the captured video image of the illuminated calculi. The digital video signal can have a video refresh rate of 10 Hz, 20 Hz, 24 Hz, 25 Hz, 30 Hz, 40 Hz, 50 Hz, 60 Hz, or another suitable video refresh rate.

FIGS. 10A-10B illustrate examples of feedback-controlled laser treatment systems. In FIG. 10A, a laser treatment system 1000A including an endoscope 910 integrated with a feedback-controlled laser treatment system 1010 that receives camera feedback. The laser treatment system 1000A, which is an example of the laser treatment system 100, comprises the endoscope 910, the feedback-controlled laser treatment system 1010, a laser source 1020, and a light source 1030. In various examples, a portion or the entirety of the feedback-controlled laser treatment system 1010 may be embedded into the endoscope 910.

The feedback-controlled laser treatment system 1010, which is an example of the laser feedback control system 200, includes a spectrometer 1011 (an example of the spectroscopic sensor 242), a feedback analyzer 1012 (an example of at least a portion of the feedback analyzer 240), and a laser controller 1013 (an example of the laser controller 260). The laser source 1020 is an example of the laser system 202, and can be coupled to the laser fiber 912. Fiber integrated laser systems may be used for endoscopic procedures due to their ability to pass laser energy through a flexible endoscope and to effectively treat hard and soft tissue. These laser systems produce a laser output beam in a wide wavelength range from UV to IR area (200 nm to 10000 nm). Some fiber integrated lasers produce an output in a wavelength range that is highly absorbed by soft or hard tissue, for example 1900-3000 nm for water absorption or 400-520 nm for oxy-hemoglobin and/or deoxy-hemoglobin absorption. Table 1 above is a summary of IR lasers that emit in the high water absorption range 1900-3000 nm.

Some fiber integrated lasers produce an output in a wavelength range that is minimally absorbed by the target soft or hard tissue. These types of lasers provide effective tissue coagulation due to a penetration depth that similar to the diameter of a small capillary 5-10 μm. Examples of laser source 1020 may include UV-VIS emitting $In_xGa_{1-x}N$ semiconductor lasers such as GaN laser with emission at 515-520 nm, $In_xGa_{1-x}N$ laser with emission at 370-493 nm, $Ga_xAl_{1-x}As$ laser with emission at 750-850 nm, or $In_xGa_{1-x}As$ laser with emission at 904-1065 nm, among others.

The light source 1030 may produce an electromagnetic radiation signal that may be transmitted to the target structure 122 via a first optical pathway extending along the elongate body of the endoscope. The first optical pathway may be located within the working channel 913. In an example, the first optical pathway may be an optical fiber separate from the laser fiber 912. In another example, as illustrated in FIG. 10A, the electromagnetic radiation signal may be transmitted through the same laser fiber 912 used for transmitting laser beams. The electromagnetic radiation exits the distal end of the first optical pathway and projects to the target structure and surrounding environment. As illustrated in FIG. 10A, the target structure is within the view of the endoscopic camera 916, such that in response to the electromagnetic radiation projecting to the target structure and surrounding environment, the endoscopic camera 916, such as a CCD or CMOS camera, may collect the signal reflected from target structure 122, produce an imaging signal 1050 of the target structure, and deliver the imaging signal to the feedback-controlled laser treatment system 1010. In some examples, imaging system other than the CCD or CMOS camera, such as laser scanning, can be used for collecting spectroscopic response.

In addition to or in lieu of the feedback signal (e.g., imaging signal) generated and transmitted through the camera system 916, in some examples, the signal reflected from the target structure may additionally or alternatively be collected and transmitted to the feedback-controlled laser treatment system 1010 through a separate fiber channel or a laser fiber such as associated with the endoscope 910. FIG. 10B illustrates an example of a laser treatment system 1000B including the endoscope 910 integrated with the feedback-controlled laser treatment system 1010 configured to receive spectroscopic sensor feedback. A reflected spectroscopic signal 1070 (which is an example of the feedback signals 130 of FIGS. 1 and 2) may travel back to the feedback-controlled laser treatment system 1010 through the same optical pathway, such as the laser fiber 912, that is used for transmitting the electromagnetic radiation from the light source 1030 to the target structure. In another example, the reflected spectroscopic signal 1070 may travel to the feedback-controlled laser treatment system 1010 through a second optical pathway, such as a separate optical fiber channel from the first optical pathway transmitting the electromagnetic radiation from the light source 1030 to the target structure.

The feedback-controlled laser treatment system 1010 may analyze one or more feedback signals (e.g., the imaging signal 1050 of the target structure or the reflected spectroscopic signal 1070) to determine an operating state for the laser source 1020. The spectrometer 1011 may generate one or more spectroscopic properties from the one or more feedback signals, such as by using one or more of a FTIR spectrometer, a Raman spectrometer, a UV-VIS spectrometer, a UV-VIS-IR spectrometer, or a fluorescent spectrometer, as discussed above with reference to spectroscopic sensor 242. The feedback analyzer 1012 may be configured to identify or classify the target structure as one of a plurality of structure categories or structure types, such as by using one or more of the target detector 246 or the target classifier 248. The laser controller 1013 may be configured to determine an operating mode of the laser system 1020, as similarly discussed above with reference to FIG. 2.

The light source 1030 may produce electromagnetic radiation within an optical range from UV to IR. Table 2 below presents examples of light source 1030 for the spectroscopic system as applicable to the examples discussed herein.

TABLE 2

Light sources for spectroscopic system

| Application | Wavelength Range | Type |
|---|---|---|
| Color/VIS/NIR | 360-2500 nm | Tungsten Halogen |
| DUV | 190-400 nm | Deuterium |
| UV | 215-400 nm | Deuterium |
| UV/VIS/NIR reflection/absorption | 215-2500 nm | Deuterium/Halogen |
| UV/VIS/NIR absorption | 200-2500 nm | Deuterium/Halogen |
| UV/VIS | 200-1000 nm | Xenon |
| FTIR | 2000-25000 nm | Silicon Carbide |
| UV/VIS/IR Fluorescence | Multiple narrow emitting | LED, Laser Diode |

In some examples, the feedback analyzer 1012 may determine a distance 1060 (as shown in FIG. 10A) between the distal end of the laser fiber 912 and the target structure 122, or between the distal end of the optical pathway for receiving and transmitting the reflected signal back to the spectrometer 1011 and the target structure 122. The distance 1060 may be calculated using a spectroscopic property, such as a reflectance spectrum, produced by the spectrometer 1011. The laser controller 1013 may control the laser source 1020 to deliver laser energy to the target structure 122 if the distance 1060 satisfies a condition, such as falling below a threshold ($d_{th}$) or within a specified laser firing range. In an example, if the target structure 122 is identified as an intended treatment structure type (e.g., a specified soft tissue type or a specified calculus type) but the target structure 122 is not within the range of the laser (e.g. $d > d_{th}$), the laser controller 1013 may produce a control signal to "lock" the laser source 1020 (i.e., preventing the laser source 1020 from firing). Information about the distance 1060 and an indication of the target structure being out of the range of laser ($d > d_{th}$) may be presented to the practitioner, who may then adjust the endoscope 910 such as repositioning the distal end of the laser fiber 912 to move to closer to the target. The distance 1060, as well as the target structure type, may be monitored and determined continuously and presented to the practitioner. When the target is recognized as the intended treatment structure type, and is within the range of laser ($d <= d_{th}$), the laser controller 1013 may produce a control signal to "unlock" the laser source 1020, and the laser source 1020 may aim and fire at the target structure 122 in accordance with the laser operating mode (e.g., power setting). Examples of methods for calculating the distance 1060 from spectroscopic data are discussed below, such as with reference to FIGS. 24A-24D.

In some examples, the spectrometer 1011 may be configured to generate the spectroscopic properties (e.g., reflectance spectra) further using information about geometry and positioning of the optical pathway configured to transmit the electromagnetic radiation from the light source to the target. For example, an outer diameter of the laser fiber 912 or an outer diameter of a separate optical pathway for transmitting the spectroscopic signal reflected from the target to the spectrometer 1011, or an angle of protrusion of said fiber or pathway from the endoscope 910, may affect the intensity of reflected signal. The outer diameter and/or the protrusion angle may be measured and provided to the spectrometer 1011 to obtain the reflectance spectra data. The distance 1060 between the target structure and the distal end of the fiber, as discussed above, may be calculated using the spectra data, the measured outer diameter of the fiber or optical pathway and its angle of protrusion, and/or input signals from the endoscopic image processor.

Figure 11A:
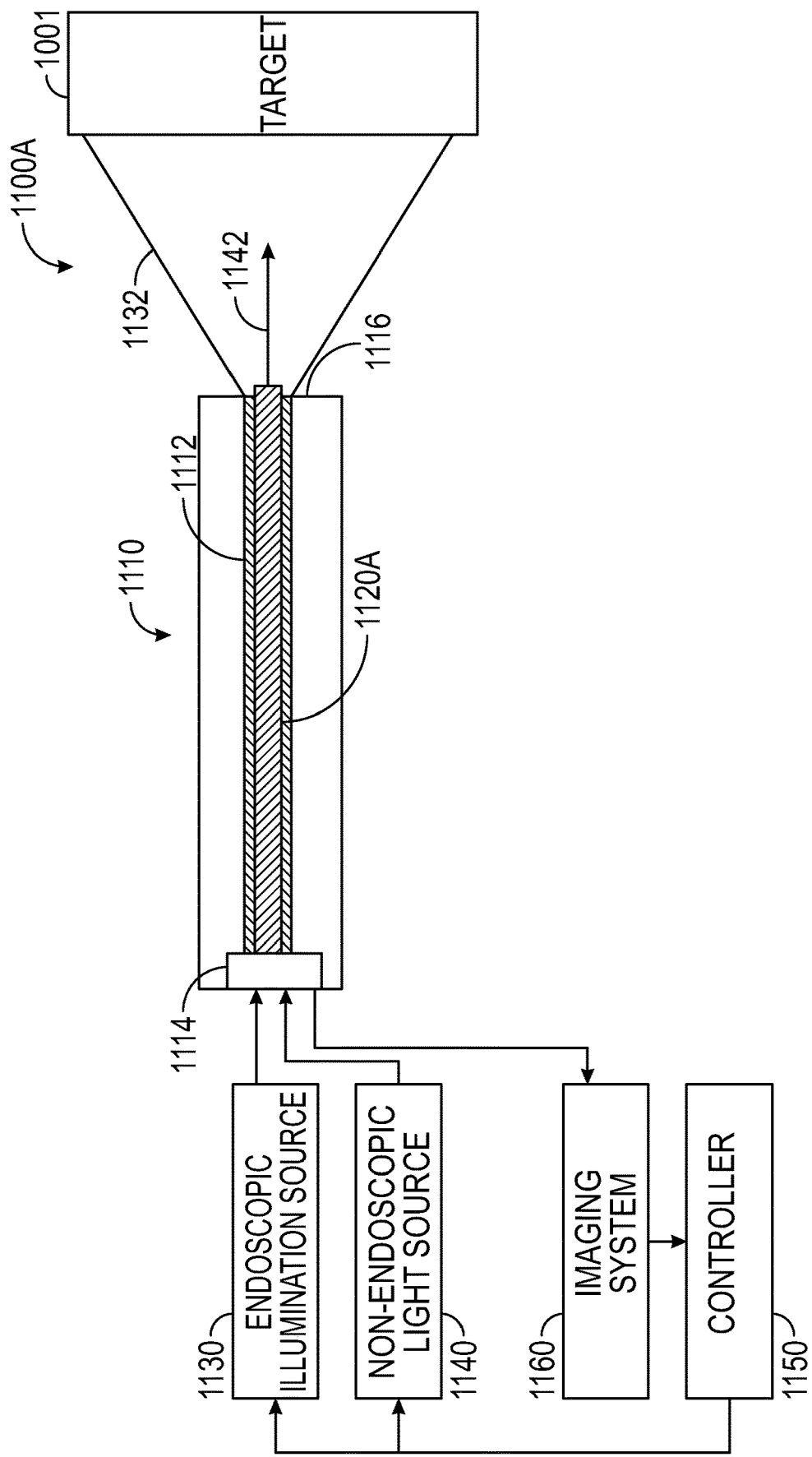
FIGS. 11A-11B are diagrams illustrating examples of an endoscopic system for identifying a target using a diagnostic beam such as a laser beam.
Figure 11B:
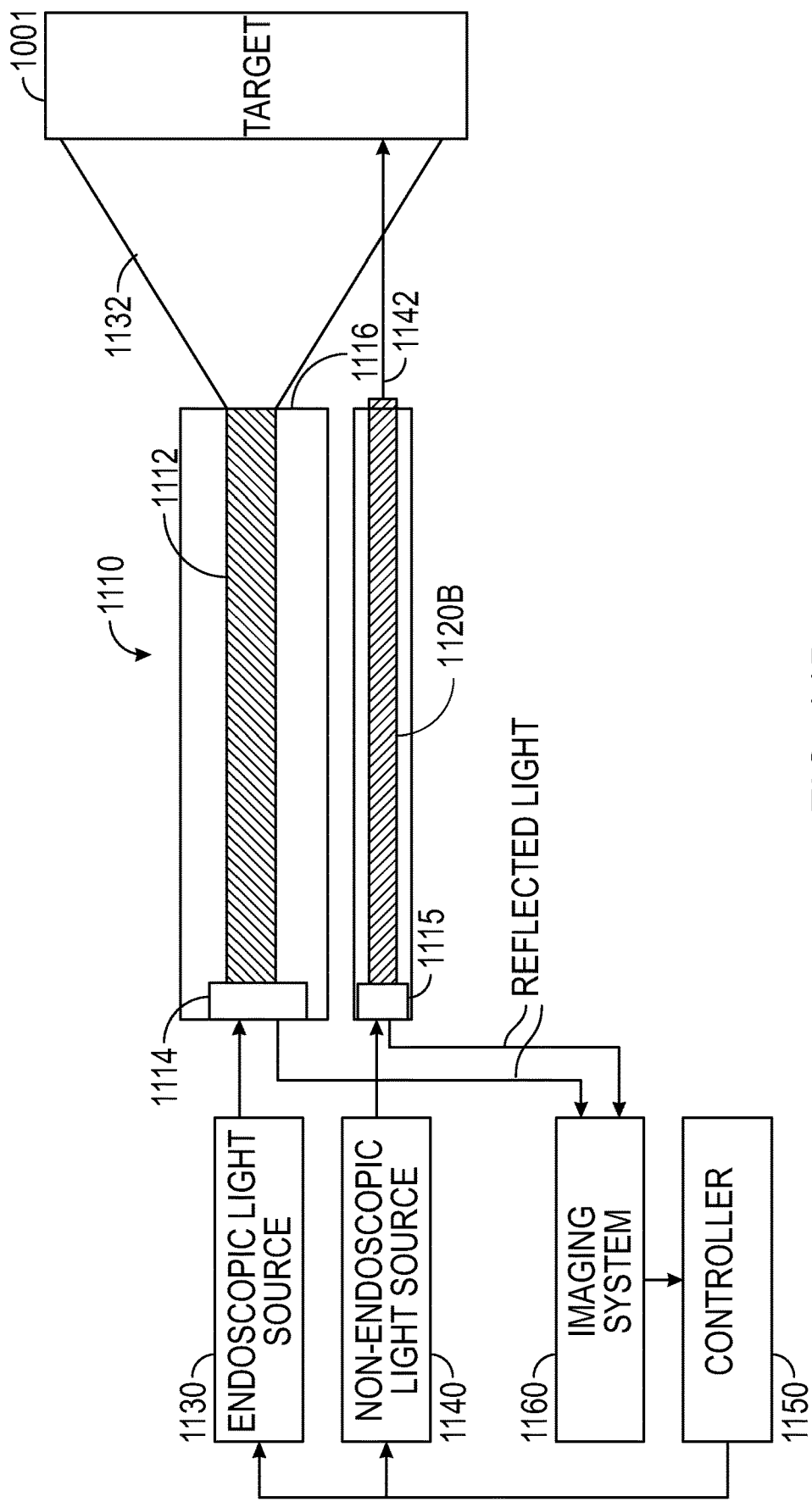

FIGS. 11A-11B are diagrams illustrating examples of an endoscopic system for identifying a target using a diagnostic beam. As illustrated in FIG. 11A, an endoscopic system 1100A can include an endoscope 1110, and an optical fiber 1120A that can be insertable through a working channel 1112 of the endoscope 1110. The endoscope 1110 can include, or otherwise be coupled to via an endoscope port 1114, at least one endoscopic illumination source 1130. The at least one endoscopic illumination source 1130 may be controllably provide different amounts of illumination. The optical fiber 1120A, when inserted through the working channel 1112, can be coupled to a non-endoscopic illumination source 1140 such as via the endoscope port 1114. The non-endoscopic illumination source 1140 can be different from the at least one endoscopic illumination source 1130. The non-endoscopic illumination source 1140 can emit a diagnostic beam 1142 through the optical fiber 1120A and proximate a distal end 1116 of the endoscope 1110. The optical fiber 1120A can direct the diagnostic beam 1142 at a target 1001. In an example, the non-endoscopic illumination source 1140 can be a laser source configured to emanating the diagnostic beam including a laser beam. In various examples, white light lamps, led light source, or fluoroscopy light sources may be inserted through the working channel of the endoscope or inserted through another port such as a laparoscopic port.

The endoscopic system 1100A may include a controller 1150. The controller 1150 may controllably operate the at least one endoscopic illumination source 1130 in different operating modes, including for example, a first mode having a first amount of illumination and the second mode having a second amount of illumination lower than the first amount. In an example, the controller 1150 may generate such a control signal to change the illumination mode (e.g., from the first mode to the second mode) in response to a trigger signal. In an example, the endoscope includes an imaging system 1160 that can take an image of the target 1001, and the controller 1150 can generate a control signal to the endoscope to change the illumination mode (e.g., from the first mode to the second mode) in response to a change in brightness or intensity of an image of the target. The first mode is hereinafter referred to as high-illumination mode, and the second mode is hereinafter referred to as low-illumination mode. In an example, the high-illumination mode and the low-illumination mode may be provided by respective different endoscopic illumination sources, such as a first endoscopic illumination source configured to emit illumination light under the high-illumination mode, and a different second endoscopic illumination source configured to emit illumination light under the low-illumination mode. The illumination light can be emitted proximate the distal end 1116 of the endoscope 1110. In an example, the illumination light can travel through an optical pathway, different than the optical fiber 1120A, within the working channel 1112. The optical pathway can direct the illumination light 1132 at the same target 1001 onto which the diagnostic beam is projected.

The controller 1150 may generate a control signal to the non-endoscopic illumination source 1140 to emit a diagnostic beam 1142 (e.g., a laser beam with a lower than therapeutic level of energy) when the at least one endoscopic illumination source 1130 changes from the high-illumination mode to the low-illumination mode. In an example, the low-illumination mode includes switching off illumination of the endoscope. By dimming the illumination at the target site under the low-illumination mode, reflection from the target of the diagnostic beam incident on the target can be enhanced, which can help improve target identification.

In some examples, the controller 1150 may generate a control signal to a display to display an image of the target while the illumination mode is in the second mode, wherein the image is either a prior image or a modified image of a current image of the target. The controller 1150 may determine a composition of a target based on the diagnostic beam incident on the target and light from the diagnostic beam being reflected from the target. In an example, the controller 1150 may determine a first composition of a first portion of a calculus target, and to determine a different second composition of a second portion of the calculus target. Based on the identified composition of different portions of the target, the controller 1150 may program a first laser setting, or generate a recommendation of programming the first laser setting, to target the first portion of the calculus target. The controller 1150 may further program a second laser setting different from the first laser setting, or generate a recommendation of programming the second laser setting, to target the second portion of the calculus target.

In an example, after the non-endoscopic illumination source 1140 has stopped emanating the diagnostic beam 1142, the controller 1150 may generate a control signal to the endoscope to change the illumination mode from the low-illumination mode back to the high-illumination mode.

FIG. 11B illustrates an example of the endoscopic system 1100B, which is a variant of the endoscopic system 1100A. In this example, the diagnostic beam 1142 can be transmitted through an optical fiber 1120B. Unlike the optical fiber 1120A that is inserted into the working channel 1112 of the endoscope 1110, the optical fiber 1120B can be disposed in a separate from the working channel 1112. In some examples as illustrated in FIG. 11B, the diagnostic beam 1142 may be delivered through a secondary port 1115, such as a laparoscopic port in an example, separate from the endoscopic port 1114 used for delivering endoscopic illumination light. The optical fiber 1120B can be positioned such that the distal end 116 of the endoscope 1110 and the distal end of the optical fiber 1120B both aim at the target 1001.

Figure 12:
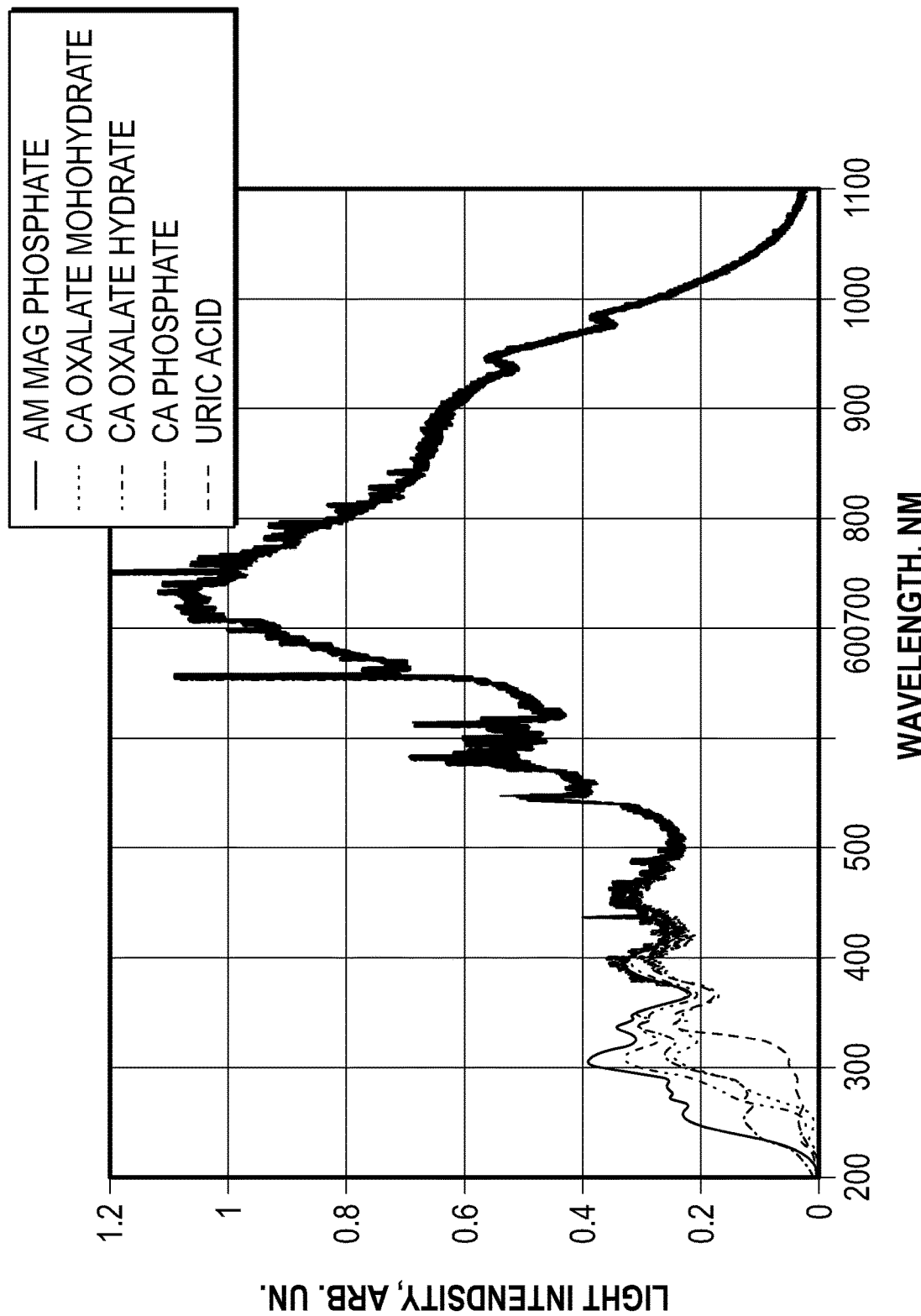
FIGS. 12 and 13A-13B are diagrams illustrating reflectance spectra for identifying target types, such as for identifying compositions of different types of kidney stones.
Figure 13A:
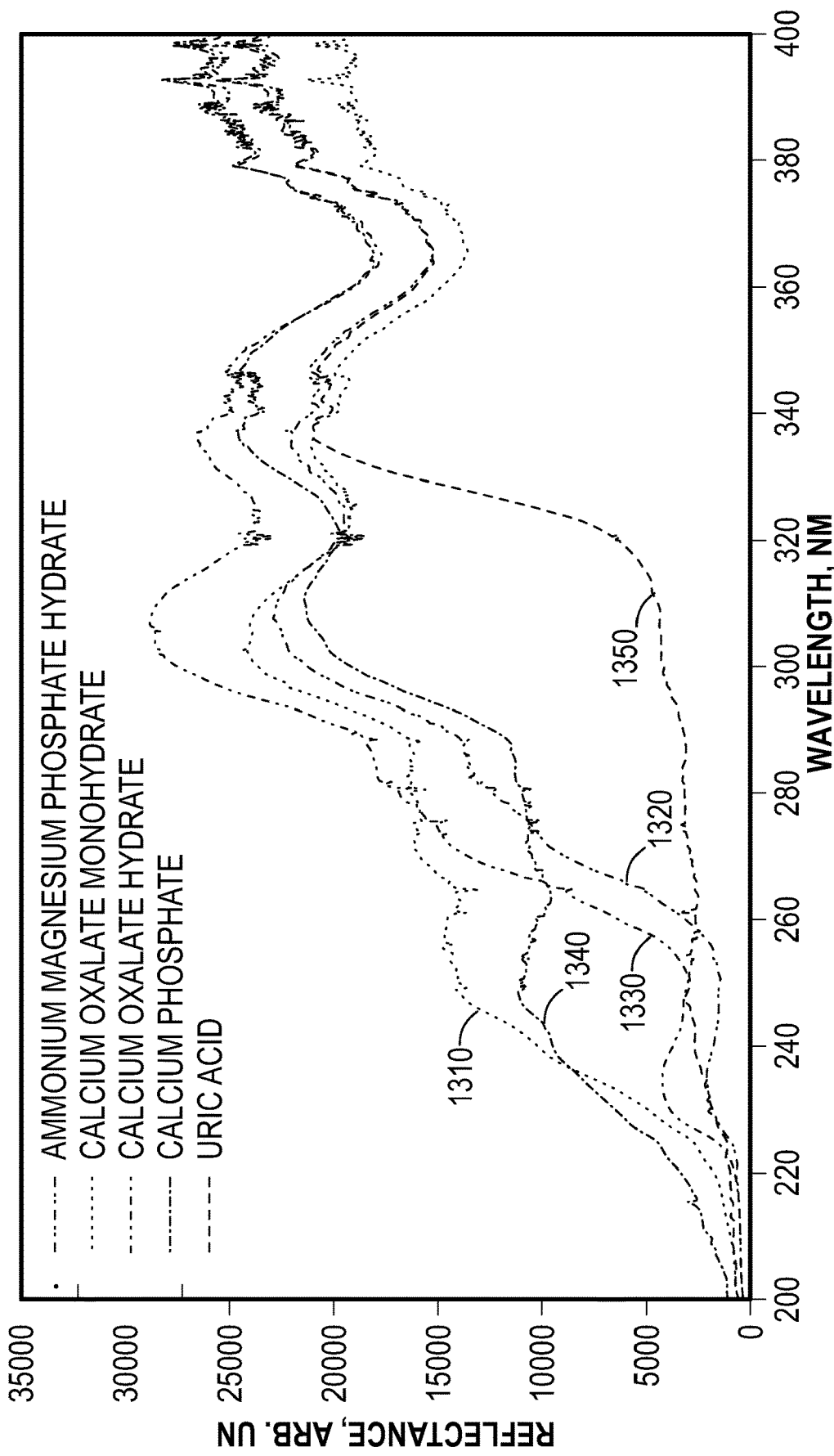
Figure 13B:
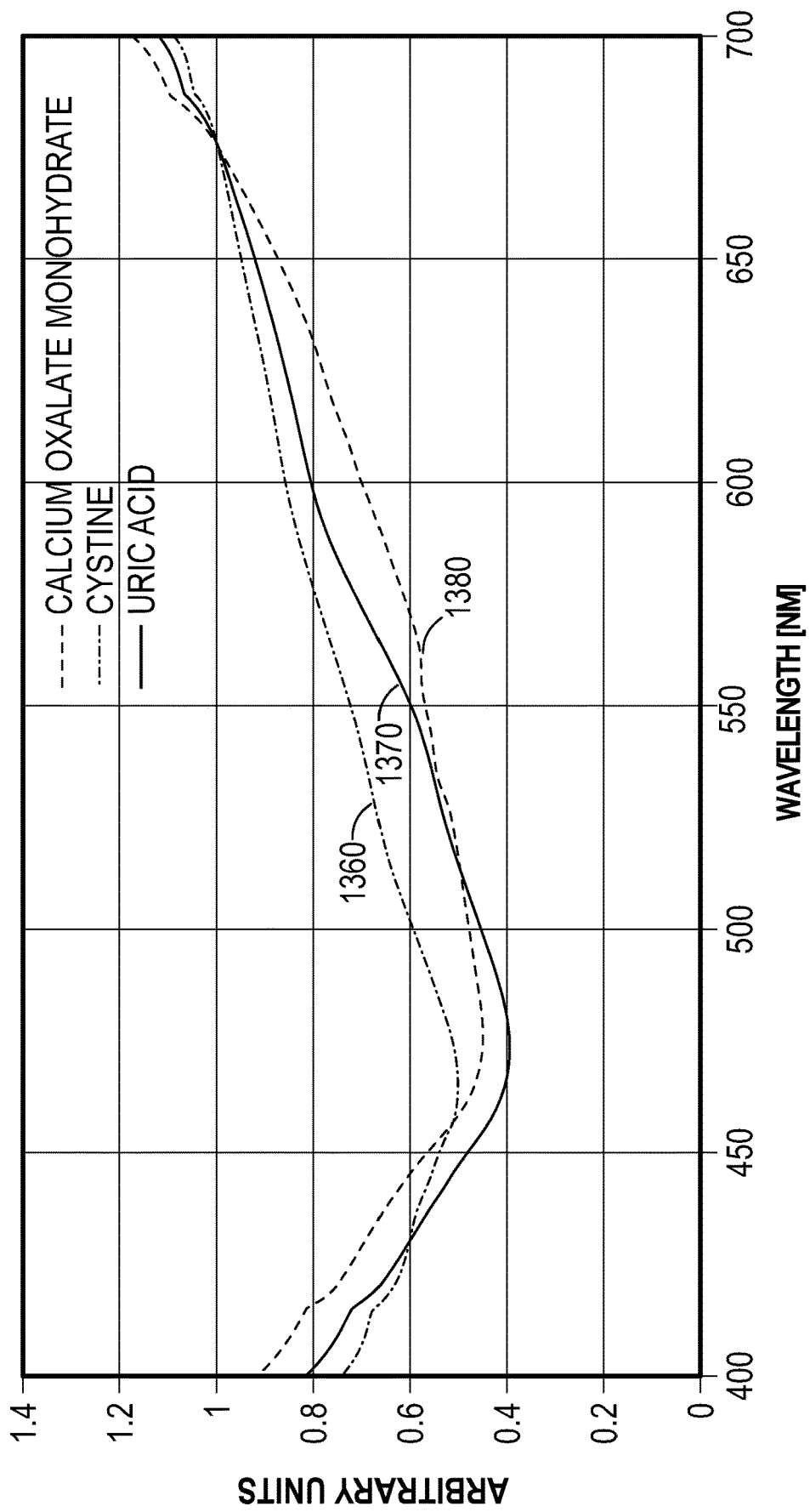

FIGS. 12 and 13A-13B are diagrams illustrating reflectance spectra data for identifying different types of targets, such as for identifying compositions of several different types of kidney stones, via UV-VIS spectroscopy, or UV-VIS-IR spectroscopy. The reflectance spectra data was collected by aiming a UV-VIS spectrometer or UV-VIS-IR spectrometer at each of the images of the five primary types of kidney stones including calcium oxalate stone (Monohydrate), calcium oxalate stone (Dihydrate), calcium phosphate stone, struvite stone, and uric acid stone. In an example, the electromagnetic radiation can include one or more ultraviolet wavelengths between 10 nm to 400 nm. In another example, as illustrated in FIG. 12, the reflectance spectra used to identify of different types of targets can be recoded from the spectrometer in a wavelength range 200-1100 nm. Illustrated therein are reflectance spectra of kidney stone compositions, including ammonium magnesium (AM MAG) phosphate hydrate, calcium (CA) oxalate monohydrate, calcium (CA) oxalate hydrate, calcium (CA) phosphate, and uric acid. The reflectance spectra of these stone compositions are more discernable at lower wavelength range (e.g., below 400 nm) then at higher wavelength range (e.g., above 400). FIG. 13A illustrates a portion of the reflectance spectra shown in FIG. 12 in the 200-400 nm wavelength range, including ammonium magnesium phosphate hydrate spectra 1310, calcium oxalate monohydrate spectra 1320, calcium oxalate hydrate spectra 1330, calcium phosphate spectra 1340, and uric acid spectra 1350. This UV wavelength range is one area where the differences may be identified in the spectra of the stone images. FIG. 13B illustrates reflectance spectra of various kidney stone compositions in the 400-700 nm wavelength range, including cystine spectra 1360, uric acid spectra 1370, and calcium oxalate monohydrate spectra 1380. With the UV-VIS spectroscopy or the UV-VIS-IR spectroscopy, it is possible to distinguish between different types of targets, such as different types of kidney stones.

Figure 14:
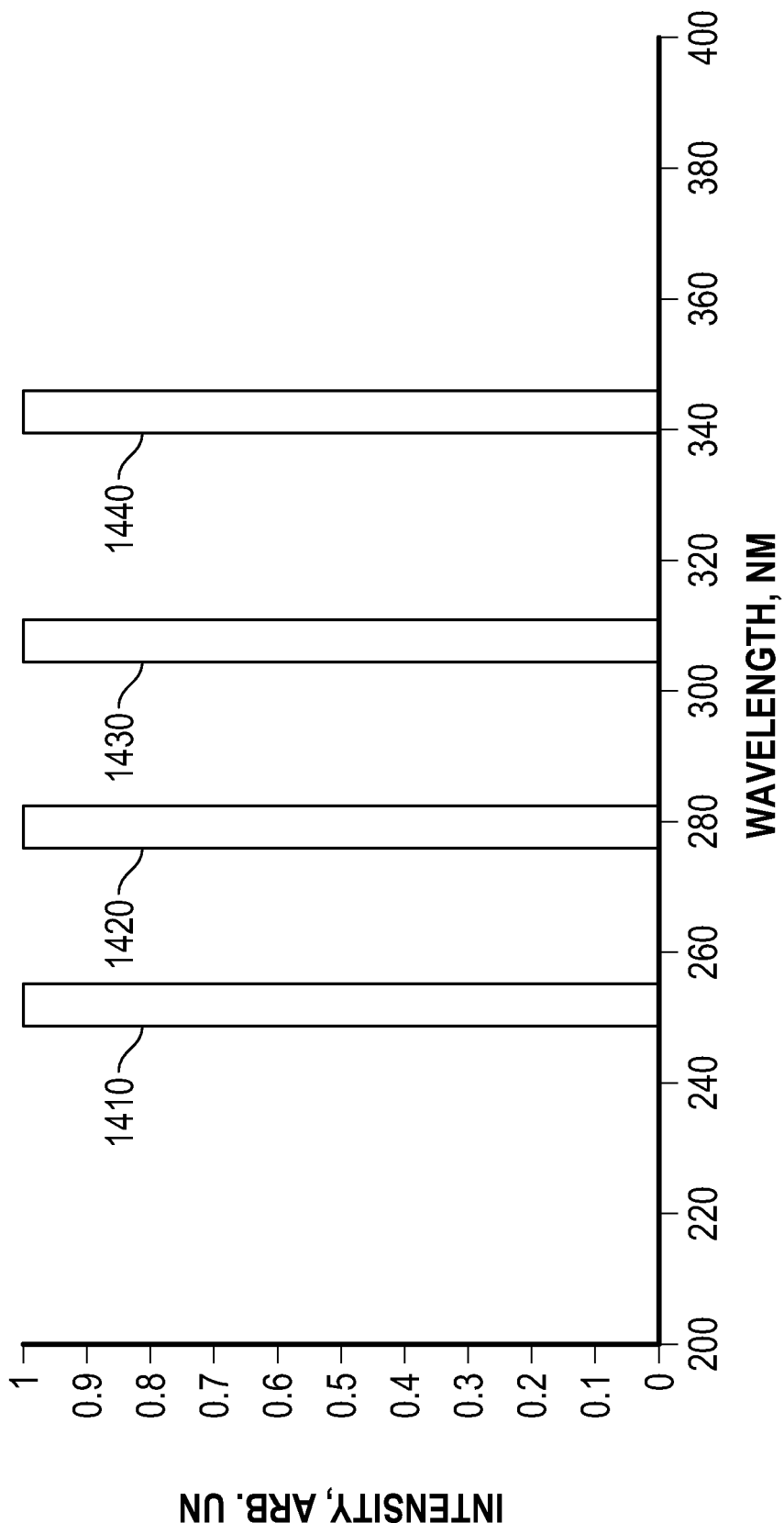
FIGS. 14-15 illustrate light peaks corresponding to different sections of the UV wavelength and the reflectance spectra of the several types of stones in FIGS. 13A-13B.
Figure 15:
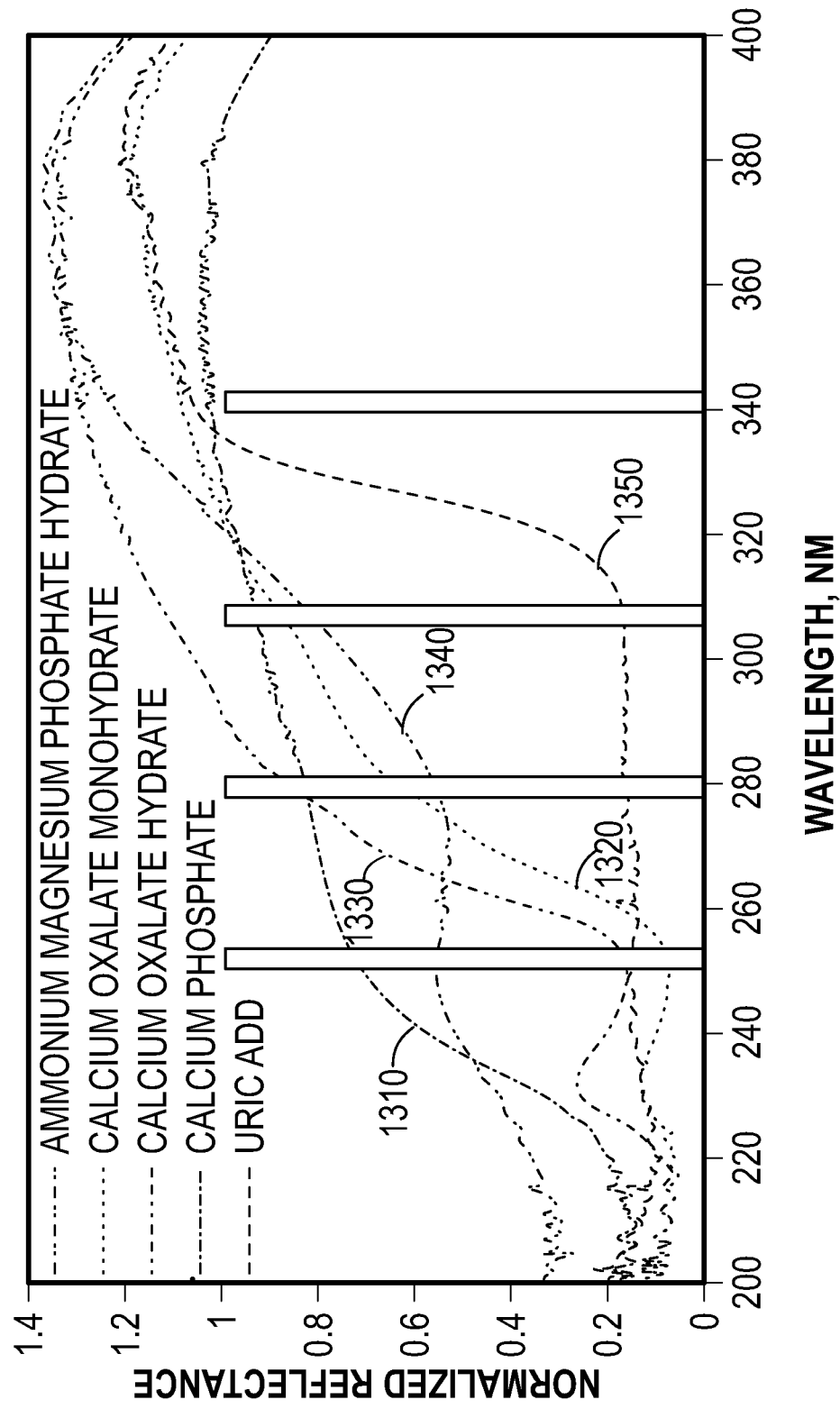

Since the UV wavelength range is, thus, promising in distinguishing different target compositions, such as kidney stones for example, there is need for a light source within the system that will allow for analysis of this region. FIG. 14 shows light peaks 1410, 1420, 1430, and 1440 that cover respective sections of the UV wavelength range around 250 nm, 280 nm, 310 nm, and 340 nm, respectively. FIG. 15 overlays these light peaks 1410-1440 with the normalized reflectance spectra of the several types of stones from FIGS. 13A-13B. These light peaks 1410-1440 demonstrate a potential light source that would allow a spectrometer to analyze the composition of target in the UV wavelengths.

Figure 16A:
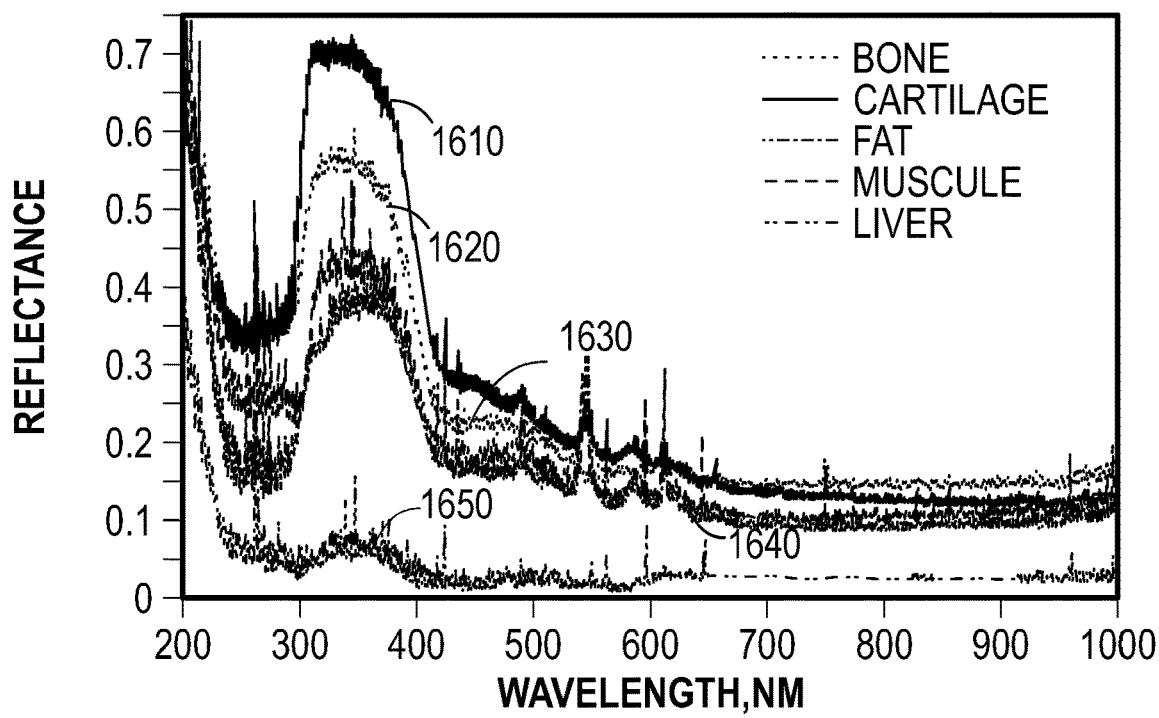
FIGS. 16A-16B illustrate examples of reflectance spectra captured on a UV-VIS spectrometer from various soft and hard tissue compositions.
Figure 16B:
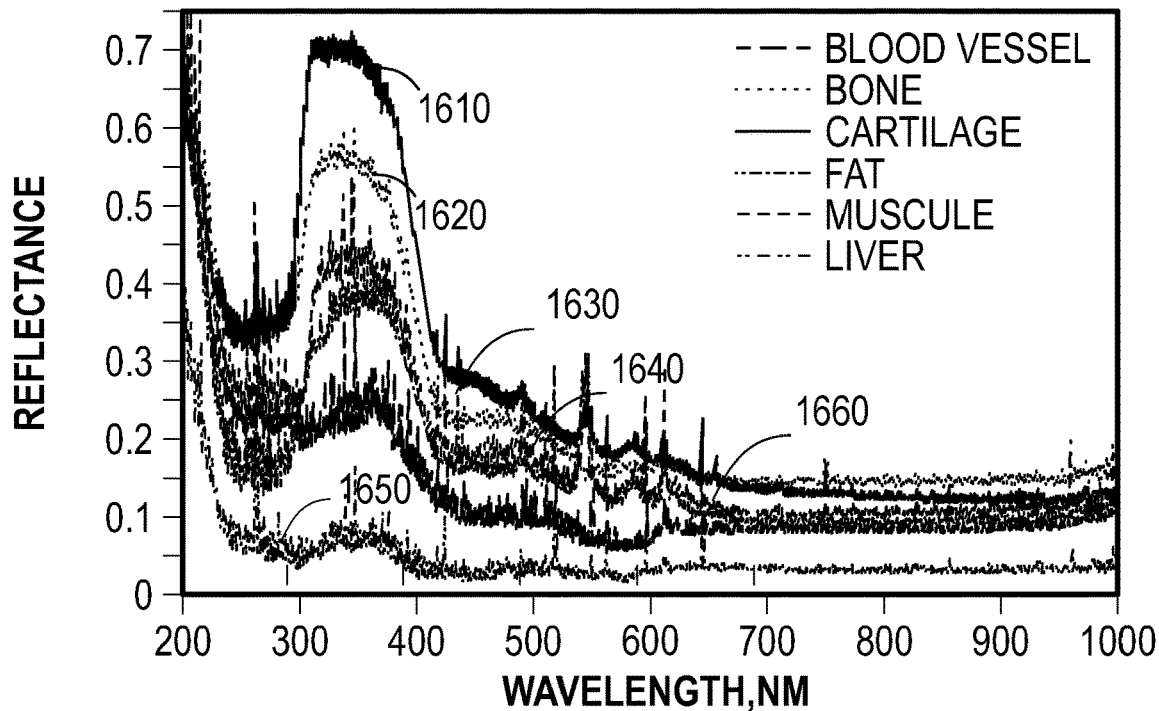
Figure 16C:
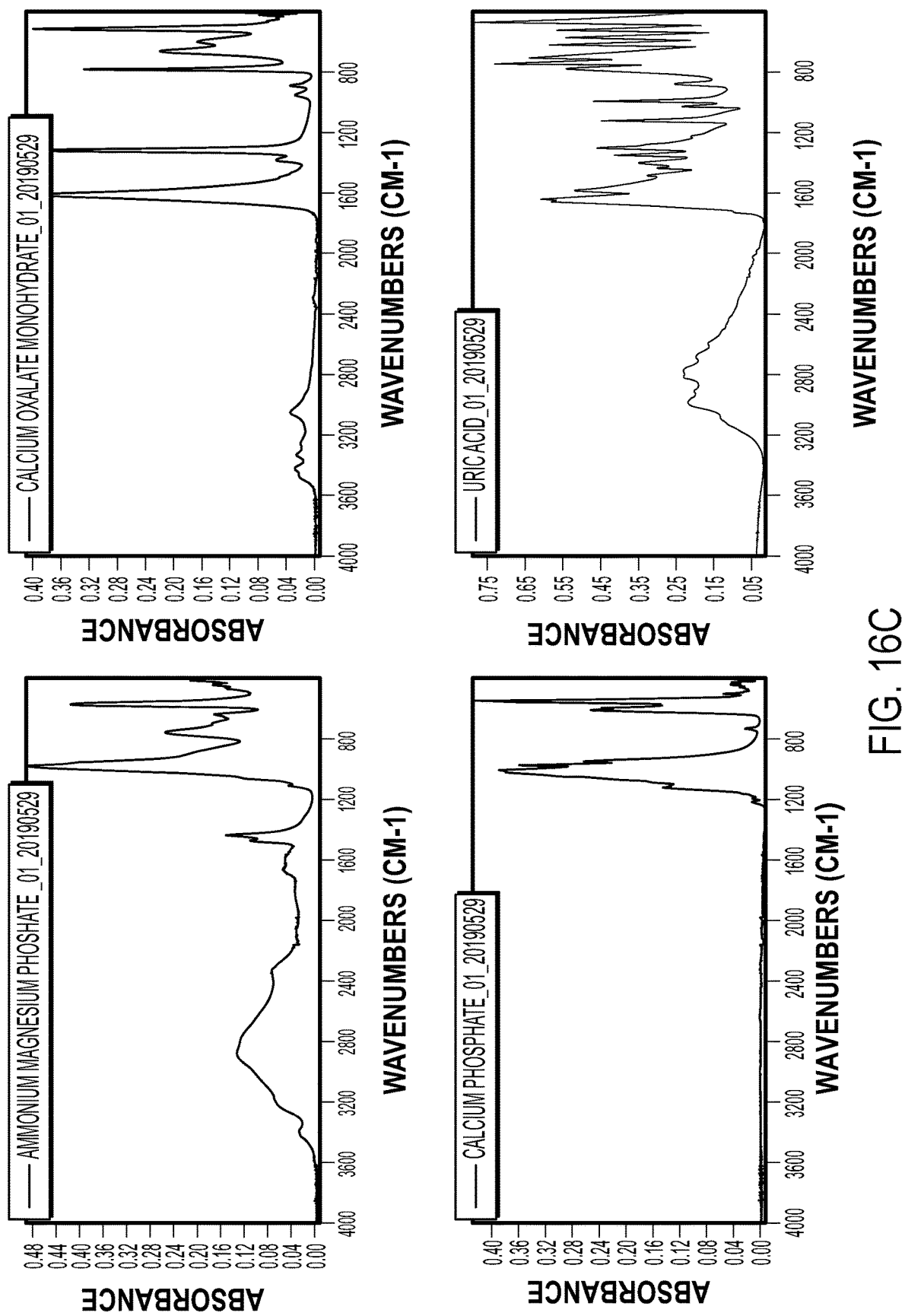
FIG. 16C illustrates examples of FTIR spectra of typical stone compositions.
Figure 16D:
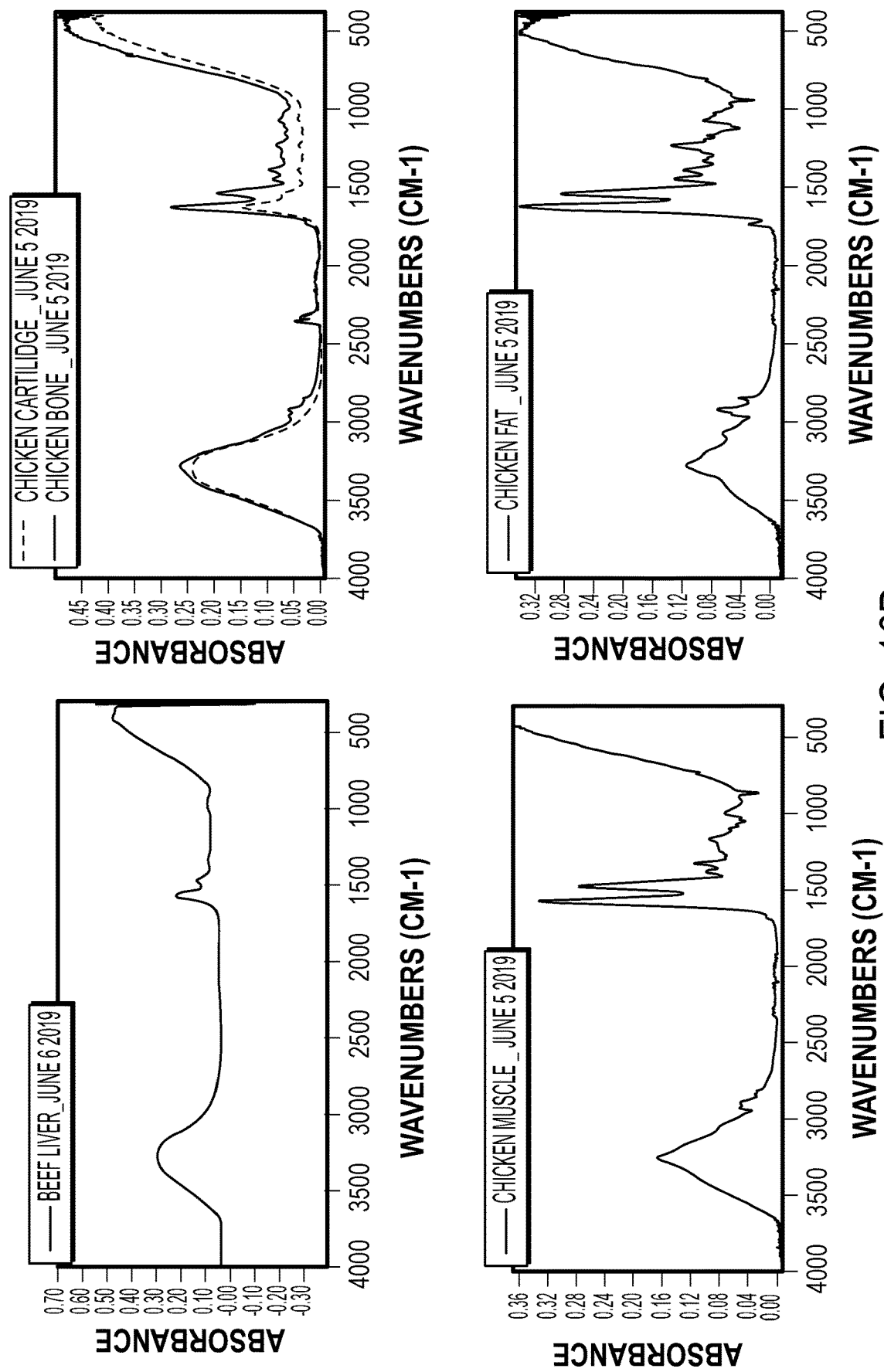
FIG. 16D illustrates examples of FTIR spectra of some soft and hard tissue compositions.

FIG. 16A illustrates an example of normalized reflectance spectra captured on a UV-VIS spectrometer from various tissue types, including cartilage spectra 1610, bone spectra 1620, muscle spectra 1630, fat spectra 1640, and liver tissue spectra 1650. FIG. 16B illustrates another example of normalized reflectance spectra captured on a UV-VIS spectrometer from various soft and hard tissue, including cartilage spectra 1610, bone spectra 1620, muscle spectra 1630, fat spectra 1640, liver tissue spectra 1650, and blood vessel spectra 1660. The reflectance spectra data shown in FIGS. 16A-16B demonstrate the feasibility of analyzing the composition of a target from a method that could be utilized within the working channel of an endoscope. Similarly to the spectra captured from the stone images, the UV-VIS region may be used for identifying different types of targets. FIG. 16C illustrates an example of FTIR spectra of typical stone compositions, and FIG. 16D is in regard to example FTIR spectra of some soft and hard tissue compositions.

Example Laser treatment System

Features as described herein may be used in relation to a laser system for various applications where it may be advantageous to incorporate different types of laser sources. For instance, the features described herein may be suitable in industrial or medical settings, such as medical diagnostic, therapeutic and surgical procedures.

Features as described herein may be used with a spectroscopy system, which may be used in combination with a fiber-integrated laser system and an endoscope.

Figure 17:
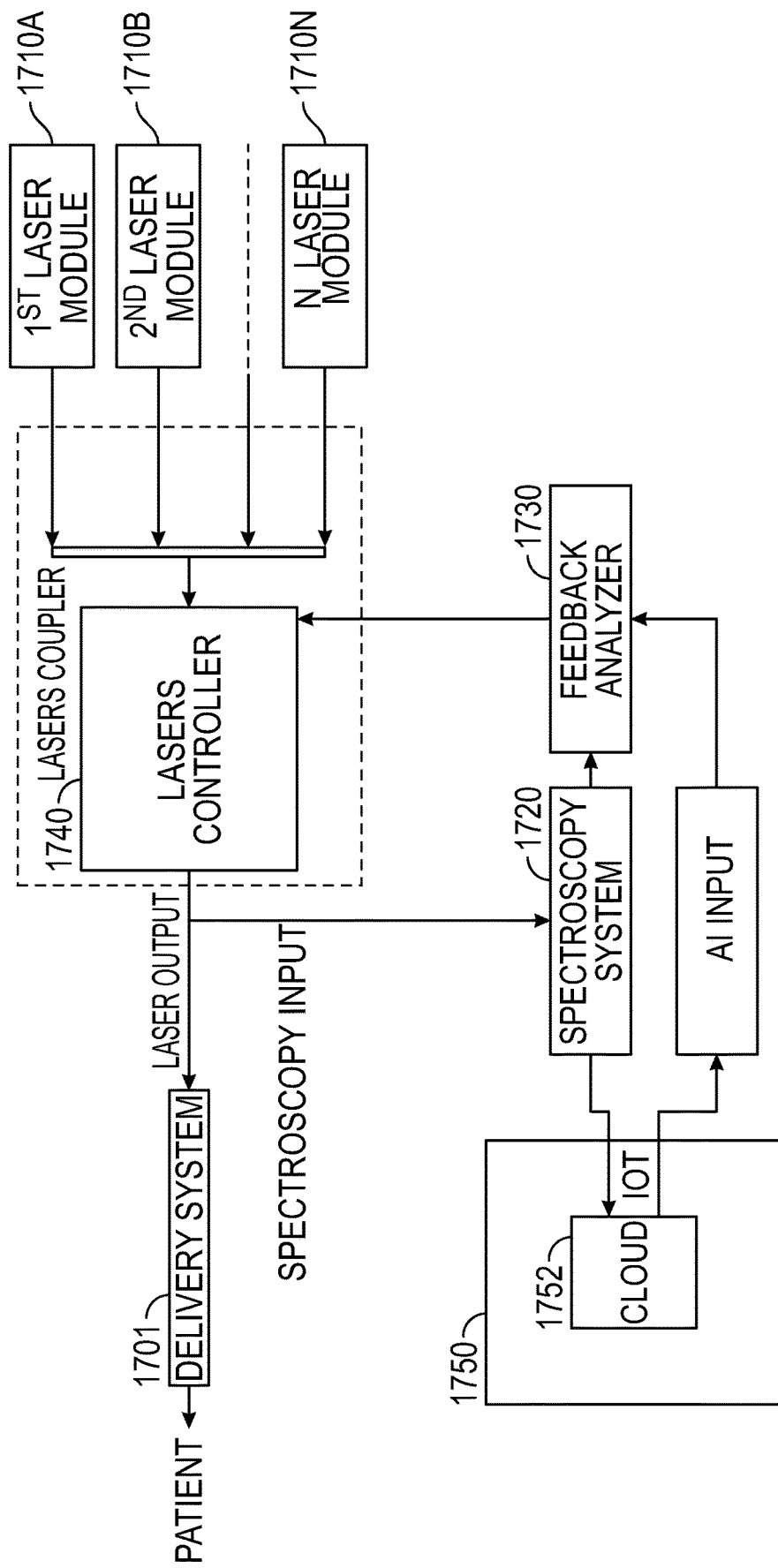
FIGS. 17-18 illustrate schematic diagrams of a laser treatment system.
Figure 18:
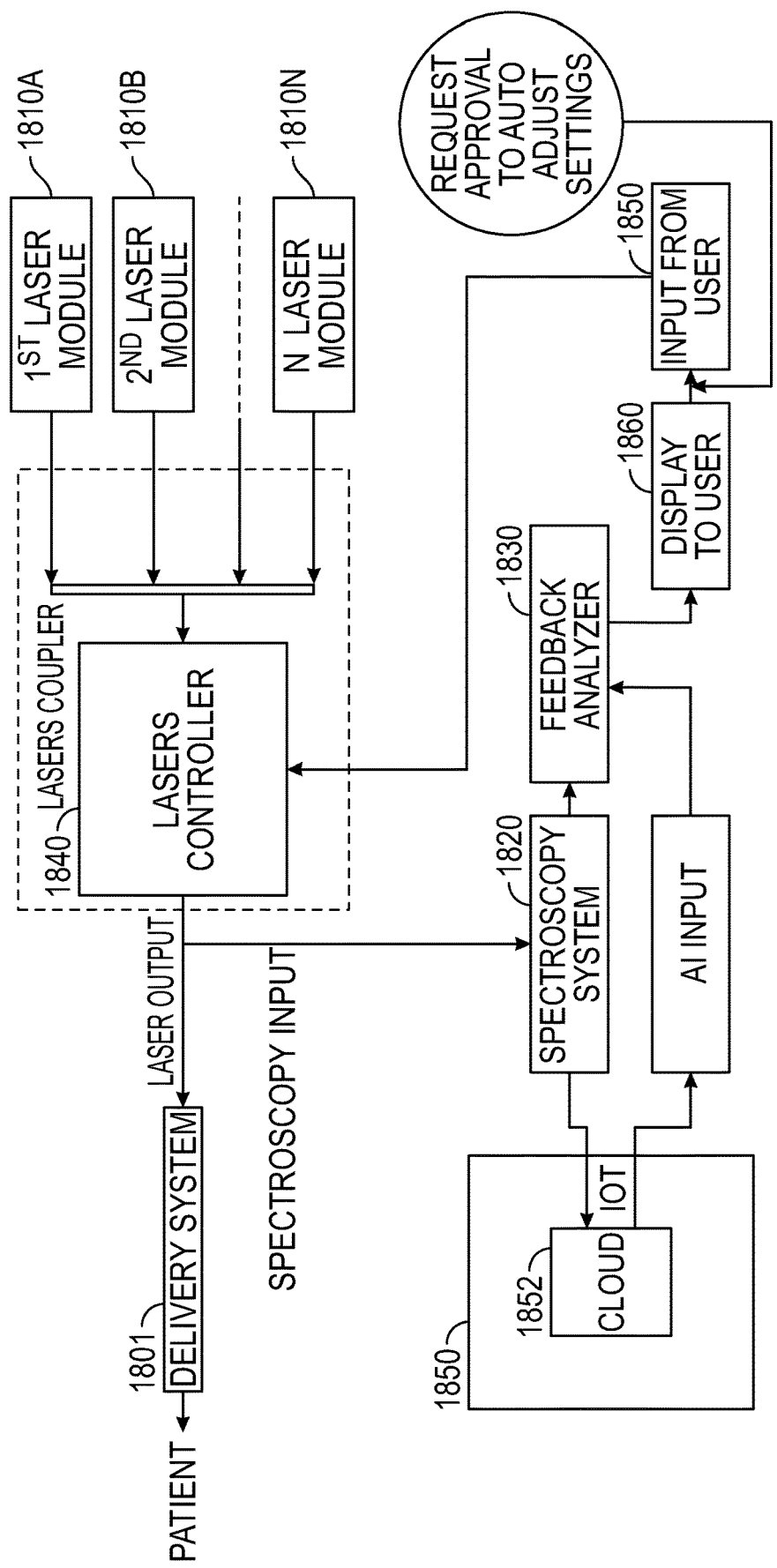

FIGS. 17-18 illustrate schematic diagrams of a laser treatment system, according to various examples as described in this disclosure. A laser treatment system may include a laser system configured to deliver laser energy directed toward a target, and a laser feedback control system configured to be coupled to the laser system. The laser system may include one or more laser modules 1710A-1710N (e.g., solid-state laser modules) that can emit similar or different wavelength from UV to IR. The number of the integrated laser modules, their output powers, emission ranges, pulse shapes, and pulse trains are selected to balance system costs and the performance required to deliver the desired effects to the targets.

The one or more laser modules 1710A-1710N may be integrated with a fiber, and included in a Laser Coupling System. Fiber-integrated laser systems may be used for endoscopic procedures due to their ability to pass laser energy through a flexible endoscope and to effectively treat hard and soft tissue. These laser systems produce a laser output beam in a wide wavelength range from UV to IR area (e.g., 200 nm to 10000 nm). Some fiber integrated lasers produce an output in a wavelength range that is highly absorbed by soft or hard tissue, for example 1900-3000 nm for water absorption or 400-520 nm for oxy-hemoglobin and/or deoxy-hemoglobin absorption. Various IR lasers may be used as the laser source in endoscopic procedures, such as those describe above with referenced to Table 1.

The Laser Modules 1710A-1710N may each consist of a number of solid-state laser diodes integrated into an optical fiber in order to increase output power and deliver the emission to the target. Some fiber integrated lasers produce an output in a wavelength range that is minimally absorbed by the target soft or hard tissue. These types of lasers provide effective tissue coagulation due to a penetration depth that similar to the diameter of a small capillary 510 µm. The fiber-integrated Laser Modules 1710A-1710N as described according to various examples in this disclosure have several advantages. In an example, the light emitting by a Laser Module has a symmetric beam quality, circular and smooth (homogenized) intensity profile. The compact cooling arrangements is integrated into a laser module and make compact the whole system. The fiber-integrated Laser Modules 1710A-1710N can be easily combined with another fiber optic components. Additionally, the fiber-integrated Laser Modules 1710A-1710N support standard optical fiber connectors that allow the modules to operate well with the most optical modules without alignment. Moreover, the fiber-integrated Laser Modules 1710A-1710N can be easily replaced without changing the alignment of the Laser Coupling System, In some examples, a laser Module may produce a laser output in wavelength range that is highly absorbed by some materials such as soft or hard tissue, stone, bone, tooth etc., for example 1900-3000 nm for water absorption or 400-520 nm for oxy-hemoglobin and/or deoxy-hemoglobin absorption, as illustrated in FIG. 3C. In some examples a Laser Module may produce a laser output in a wavelength range that is low absorbed by the target, such as soft or hard tissue, stone, bone, tooth etc. This types of laser provide more effective tissue coagulation due to a penetration depth that similar to the diameter of a small capillary (e.g., 5-10 µm), as illustrated in FIG. 3C. Commercially available solid-state lasers are potential emitting sources for the laser modules. Examples of laser sources for the Laser Modules may include UV-VIS emitting $In_XGa_{1-X}N$ semiconductor lasers, such as GaN (emission 515-520 nm) or $In_XGa_{1-X}N$ (emission 370-493 nm), GaXAl1–XAs laser (emission 750-850 nm), or InXGa1–XAs laser (emission 904-1065 nm). Such laser sources may also be applicable to tissue coagulation applications.

The laser feedback control system may comprise one or more subsystems including, for example, a spectroscopy system 1720, a feedback analyzer 1730, and a laser controller 1740.

Spectroscopy System 1720

Figure 20:
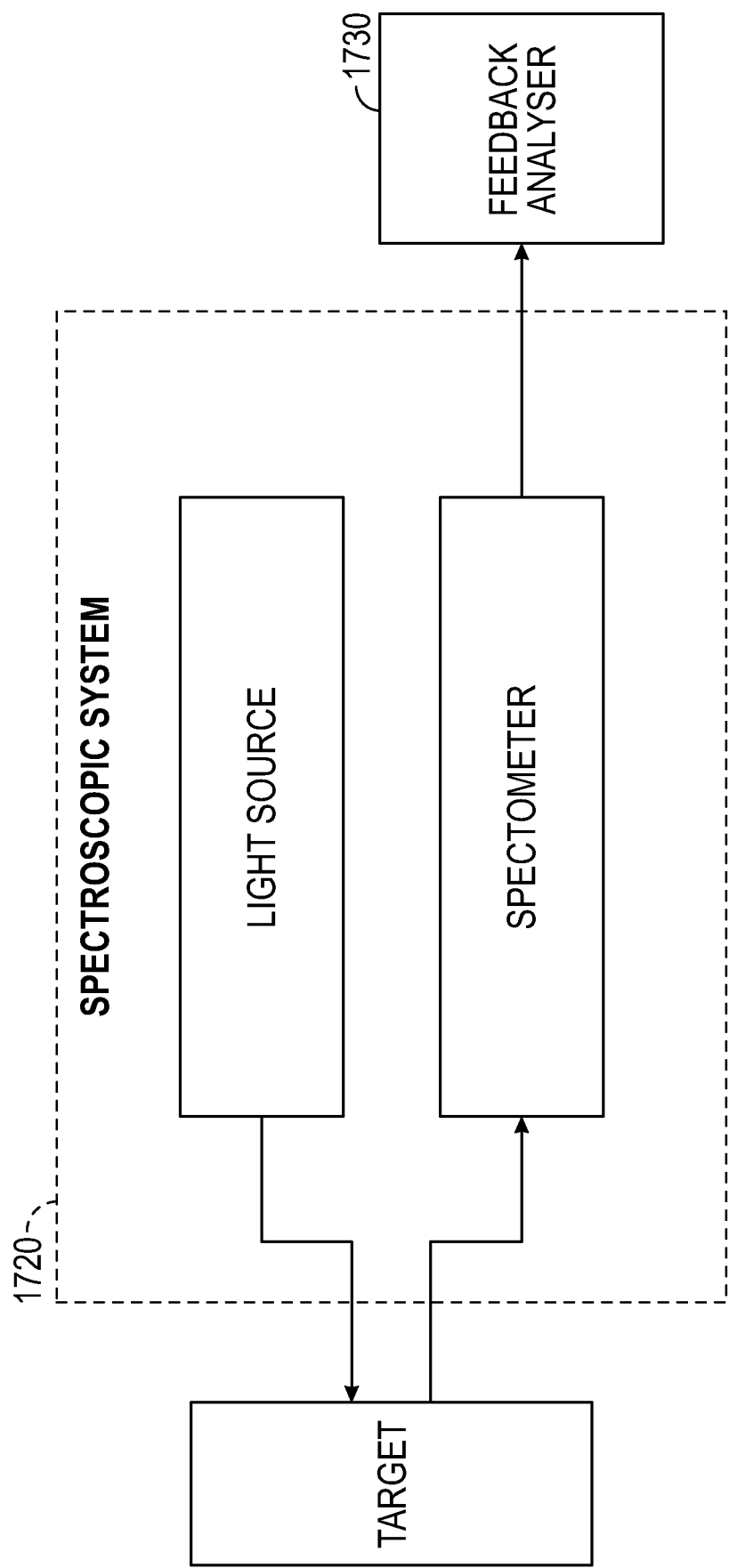
FIG. 20 illustrates a schematic of an exemplary spectroscopic system with spectroscopic feedback.

The spectroscopy system 1720 may send a control light signal from a light source to a target, such as, but not limited to, a calculi, soft or hard tissue, bond, or tooth, or industrial targets, and collects spectral response data reflected from the target. The response may be delivered to a spectrometer through a separate fiber, laser fiber, or endoscope system. The spectrometer may send the digital spectral data to the system feedback analyzer 1730. Examples of light sources for the spectroscopic system that cover an optical range from UV to IR can include those described above with reference to Table 2. FIG. 20 illustrates a schematic diagram of the Spectroscopic System 1720 with Feedback Analyzer 1730 in an example.

Optical spectroscopy is a powerful method that may be used for easy and rapid analysis of organic and inorganic materials. According to various examples described in this disclosure, a spectroscopic light source may be integrated into a separate fiber channel, a laser fiber or an endoscope system. A light source signal reflected from the target may be rapidly collected and delivered to the spectrometer by an imaging system containing a detector such as a CCD or CMOS sensor for example, which can be included in a digital endoscope. Other imaging system like laser scanning may also be used for collecting spectroscopic response. The optical spectroscopy has several advantages. It can be easily integrated with a fiber laser delivery system 1701. It is a nondestructive technique to detect and analyze material chemical composition, and the analysis can be performed in real time. The optical spectroscopy can be used to analyze different types of materials including, for example, hard and soft tissue, calculi structures, etc.

Various spectroscopic techniques may be used alone or in combination to analyze target chemical composition and create the spectroscopic feedback. Examples of such spectroscopic techniques may include UV-VIS reflection spectroscopy, fluorescent spectroscopy, Fourier-Transform Infrared Spectroscopy (FTIR), or Raman spectroscopy, among others. Table 2 above presents examples of light sources for the Spectroscopic System that cover an optical area from UV to IR and applicable to an example Tungsten Halogen light sources are commonly used to do spectroscopic measurements in the visible and near IR range. Deuterium light sources are known for their stable output and they are used for UV absorption or reflection measurements. The mixes of the Halogen light with the Deuterium light produces a wide spectral range light source providing a smooth spectrum from 200-2500 nm. A Xenon light source is used in applications where a long lifetime and high output power is needed, such as in fluorescence measurements. LED and Laser Diodes light sources provide high power at a precise wavelength; they have long lifetime, short warm-up time and high-stability. A spectroscopic light source can be integrated into a separate fiber channel, laser fiber or endoscope system. A light source signal reflected from the target can be rapidly detected and delivered to the spectrometer though a separate fiber channel or laser fiber.

Feedback Analyzer 1730

The feedback analyzer 1730 may receive inputs from various sources including spectroscopic response data from a spectrometer to suggest or directly adjust laser system operating parameters. In an example, the feedback analyzer 1730 may compare the spectroscopic response data to an available database library of target composition data. Based on the spectroscopic system feedback, the signal analyzer detects target material composition, and suggests a laser operating mode (also referred to as a laser setup), such as operating parameters for at least one laser module, to achieve effective tissue treatments for the identified tissue composition. Examples of the operating parameters may include at least one laser wavelength, pulsed or continuous wave (CW) emission mode, peak pulse power, pulse energy, pulse rate, pulse shapes, and the simultaneous or sequenced emission of pulses from at least one laser module. Although not explicitly described, sequenced pulses includes bursts of pulses which combine to deliver the selected pulse energy. Pulses as described herein refers generally to the time between starting and stopping a laser emission from a laser module. The intensity of the laser energy during each pulse may vary to have the shape of an increasing or decreasing ramp or sinusoidal profile, or any other shape alone or in combination with a sequence of pulses so long as the selected average laser power is maintained. For example, a 2 W average power setting with a pulse energy of 1 J occurs at a frequency of 2 Hz if there is only one pulse. However, the energy may also be delivered as two 0.5 J pulses in quick succession that occurs at a rate of 2 Hz. Each of those pulses may have similar pulse shapes, or different. The Feedback Analyzer 1730 utilizes algorithms and input data to directly adjust or suggest laser operating parameters such as those described in the example above.

Figure 24A:
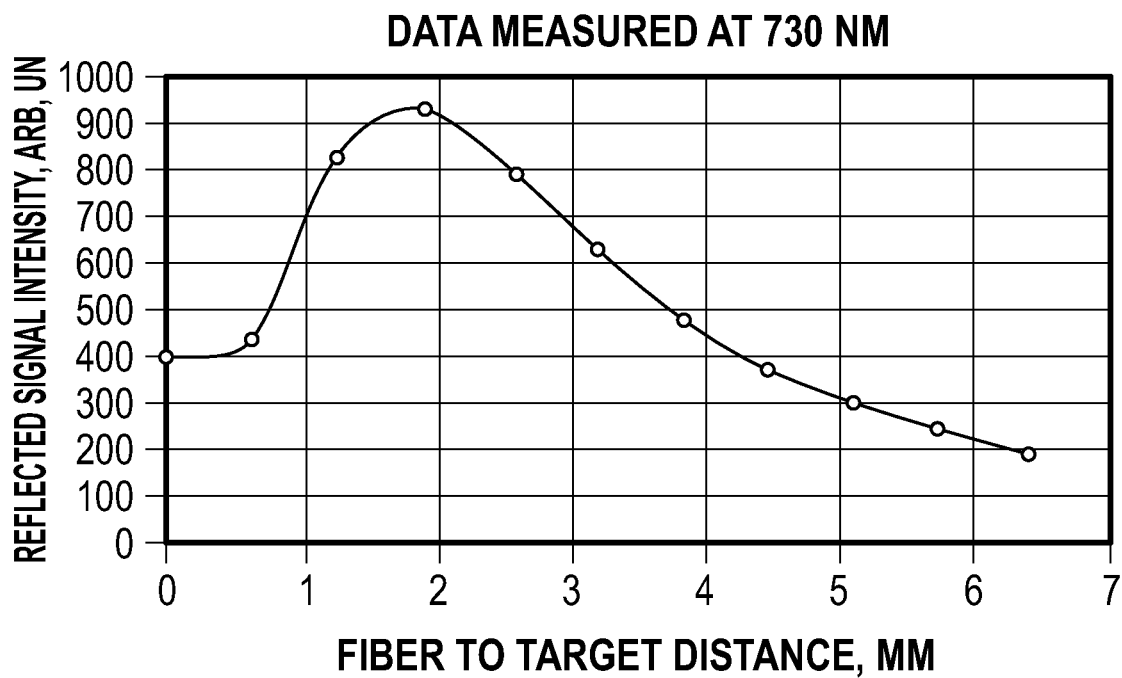
FIGS. 24A-24D are diagrams illustrating exemplary methods of calculating a distance between the distal end of the laser delivery system (e.g., an optical fiber) and the target.
Figure 24B:
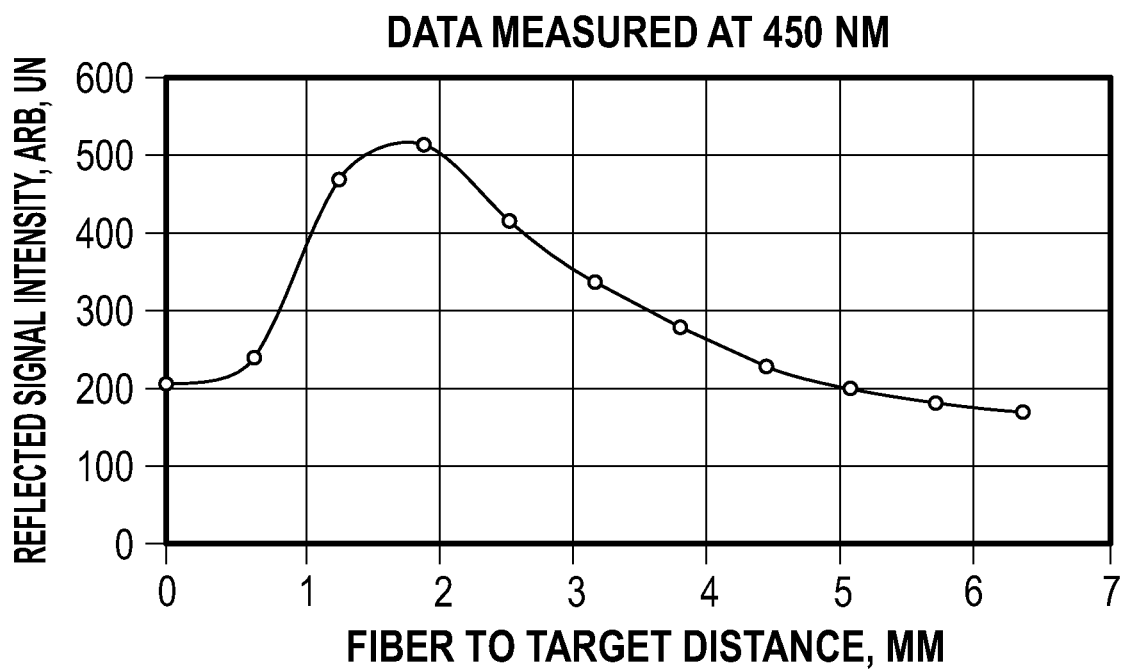

In some examples, the feedback analyzer 1730 may utilize input data to calculate and control the distance between the distal end of the laser delivery system 1701 (fiber) and a target based on specially developed algorithm. In the case of mobile target (e.g., calculi), the Feedback Analyzer 1730 may adjust or suggest laser operating parameters that creates a suction effect using vapor bubbles in water to pull targets that are beyond a predetermined threshold closer to the distal end of the fiber. This feature minimizes the effort users need to exert to maintain an effective treatment distance with mobile targets. The distance between the target and the distal end of the fiber may be calculated using spectral data, the known outer diameter of each fiber and its angle of protrusion from the endoscope, and/or input signals from the endoscopic image processor. FIGS. 24A-24D illustrated by way of example methods of calculating a distance between the distal end of the laser delivery system 1701 (fiber) and the target. An dependence of a spectroscopic reflected signal on distance between target and the laser delivery system 1701 is illustrated in FIGS. 24A-24B. FIG. 24A illustrates an example of reflected signal intensity at 730 nm measured at different distances between the tissue and spectroscopic probe distal end. FIG. 24B illustrates an example of reflected signal intensity at 450 nm measured at different distances between the tissue and spectroscopic probe distal end. Such dependence is can be determined using spectral data and information about Laser Delivery system geometry. Analysis of a spectroscopic signal allow quick estimation of the distance and delivering this information to the user.

Figure 24C:
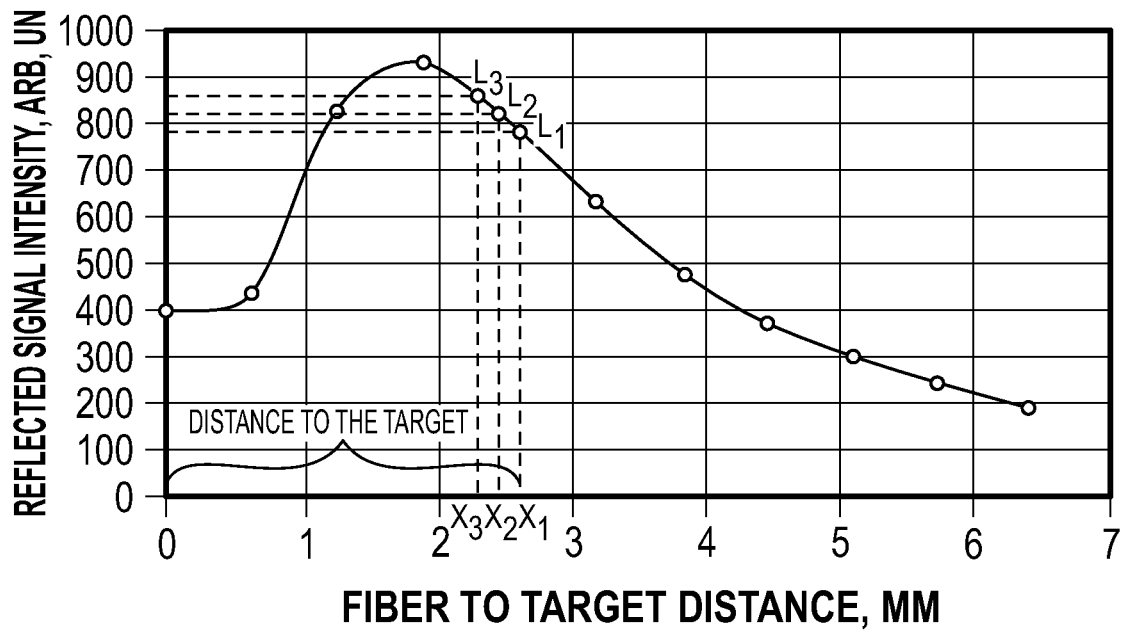

FIG. 24C is an exemplary algorithm of a distance calculation between the fiber and a tissue target. In one example, a spectroscopic system sends a control light signal from a light source to the target, collects spectral response data from the target, deliver the response signal to the spectrometer and send the digital spectral data from the spectrometer to the feedback analyzer. A calibration curve 1000, as shown in FIG. 24C, represents a relationship between a spectroscopic reflected signal intensity (e.g., spectroscopic signal reflected from the target structure in response to the electromagnetic radiation) and the distance 1060 between a distal end of a fiber and a target structure using the feedback signal reflected from the target structure, such as illustrated in FIGS. 10-11. The calibration curve 1000 may be generated by measuring the reflected signal intensity at different distances between the tissue and spectroscopic probe distal end when the target structure is projected by electromagnetic radiation at a specific wavelength (e.g., 450 nm or 730 nm). By referencing the calibration curve, analyses of a spectroscopic signal allow quick estimation of the distance.

An exemplary process of generating the calibration curve is as follows. First, reference value for each distance may be calculated. The calibration curve itself may not be used for identifying the distance, because light reflection intensity depends of the reflectance of specimen or so on. One example of reference value to cancel the effect of reflectance of specimen is as follows:

$$\text{Reference value} = dI/dx * 1/I \qquad (1)$$

During an in vivo surgery process, an operator may move the fiber or endoscope with continuous recording of the spectroscopic feedback until the reflection spectra of the target tissue composition can be detected.

Referring to FIG. 24C, a first spectrum may be measured at distance $x_1$ where the reflected signal intensity is $I_1$. At this timing, actual value of $x_1$ and curve of reflected signal intensity is unknown. Then, the fiber or endoscope distal end (reflected light detector) may be moved continually, and the next reflection light intensity $I_2$ corresponding to distance $x_2$ may be measured. $x_2$ may be close to $x_1$, such that the curve between $x_1$ and $x_2$ may be approximated as linear. At this timing, $x_1$, $x_2$ and curve of reflected signal intensity is unknown. A compared value may be calculated using $I_1$, $I_2$ and delta $(x_2-x_1)$, as follows:

$$\text{Compared value} = \text{delta}(I_2-I_1)/\text{delta}(x_2-x_1) * 1/I_1 \qquad (2)$$

Then, the reference values are searched for one that is identical to the compared value. If there is only one reference value $(x_r)$ found to be identical to the compared value given in Equation (2), then $x_r$ can be determined as distance of $x_1$. If there are two reference values $(x_{r1}, x_{r2})$, then the fiber or endoscope distal end (reflected light detector) may be continued to move, and the next reflection light intensity $I_3$ corresponding the distance $x_3$ may be measured. $x_3$ may be close to $x_2$, so that the curve between $x_2$ and $x_3$ may be approximated as linear. At this timing, $x_1$, $x_2$, $x_3$ and curve of reflected signal intensity is unknown. A new compared value can be calculated as follows using $I_1$, $I_2$, $I_3$, delta $(x_2-x_1)$, and delta $(x_3-x_2)$.

$$\text{Compared value} = \text{delta}(I_3-I_2)/\text{delta}(x_3-x_2) * 1/I_2 \qquad (3)$$

Then, the reference values are searched for one that is identical to $x_{r1}$+delta $(x_2-x_1)$ and $x_{r2}$+delta $(x_2-x_1)$. The references values can be compared to the compared value given in Equation (3). The distance whose reference value is more similar to the compared value is estimated as actual distance.

Figure 24D:
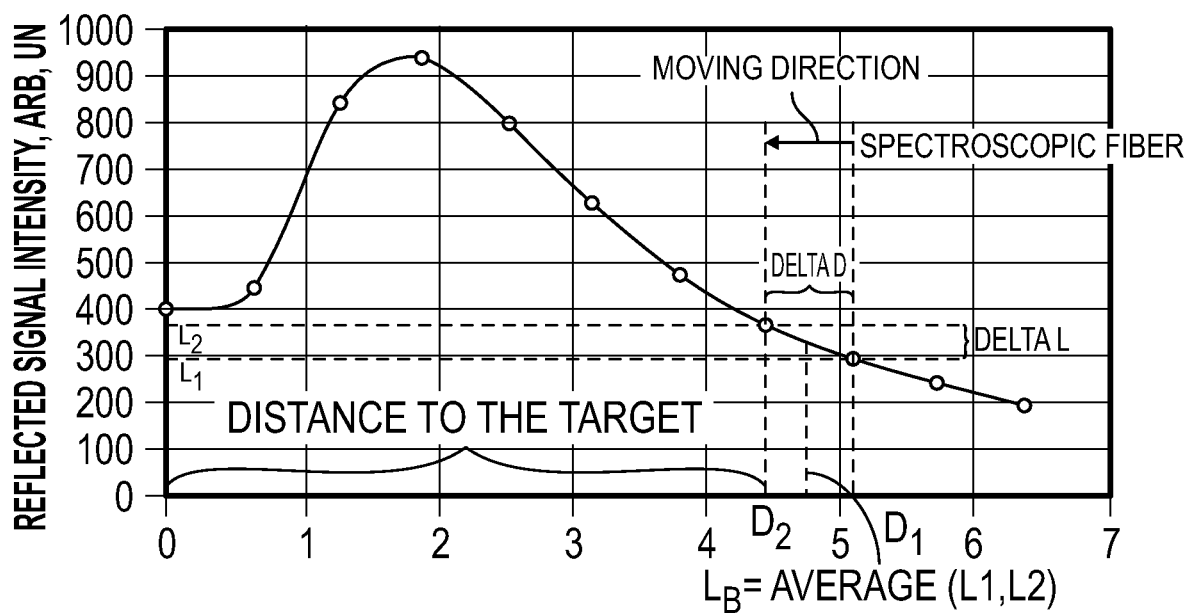

Referring to FIG. 24D, during in vivo surgery process, an example method may comprise moving the fiber or endoscope with continuous recording of the spectroscopic feedback until the reflection spectra of the target composition will be detected. With the major case when the spectroscopic distal end is moving toward the target, the intensity of the detected reflected light initially will be weak and will be increased with reducing a distance between the target and a fiber end. For example, the first spectrum was measured on distance $d_1$ where the reflected signal intensity is $I_1$. Continued slightly moving of the fiber or endoscope distal end toward the target, with continuous collecting the reflection data, and the method may measure the next reflection light intensity $I_2$ corresponding the distance $d_2$. The method may then comprise calculation of the value of reflected signal intensity change slope=delta($I_2$–$I_1$)/delta($d_2$–$d_1$). To make the value of the calculated slope independent on the reflected signal intensity the calculated slope may be normalized. The final formula to calculate the reflected signal intensity change slope at measured distance becomes:

$$\text{Slope (normalized)}=[\text{delta}(I_2\text{-}I_1)/\text{delta}(d_2\text{-}d_1)]/I_o \qquad (4)$$

where: $I_o$=AVERAGE($I1,I2$)

The method may then compare the calculated slope to the one on the calibration curve in a library to allow estimating the required distance. All calculation can be done fast using software.

Figure 25A:
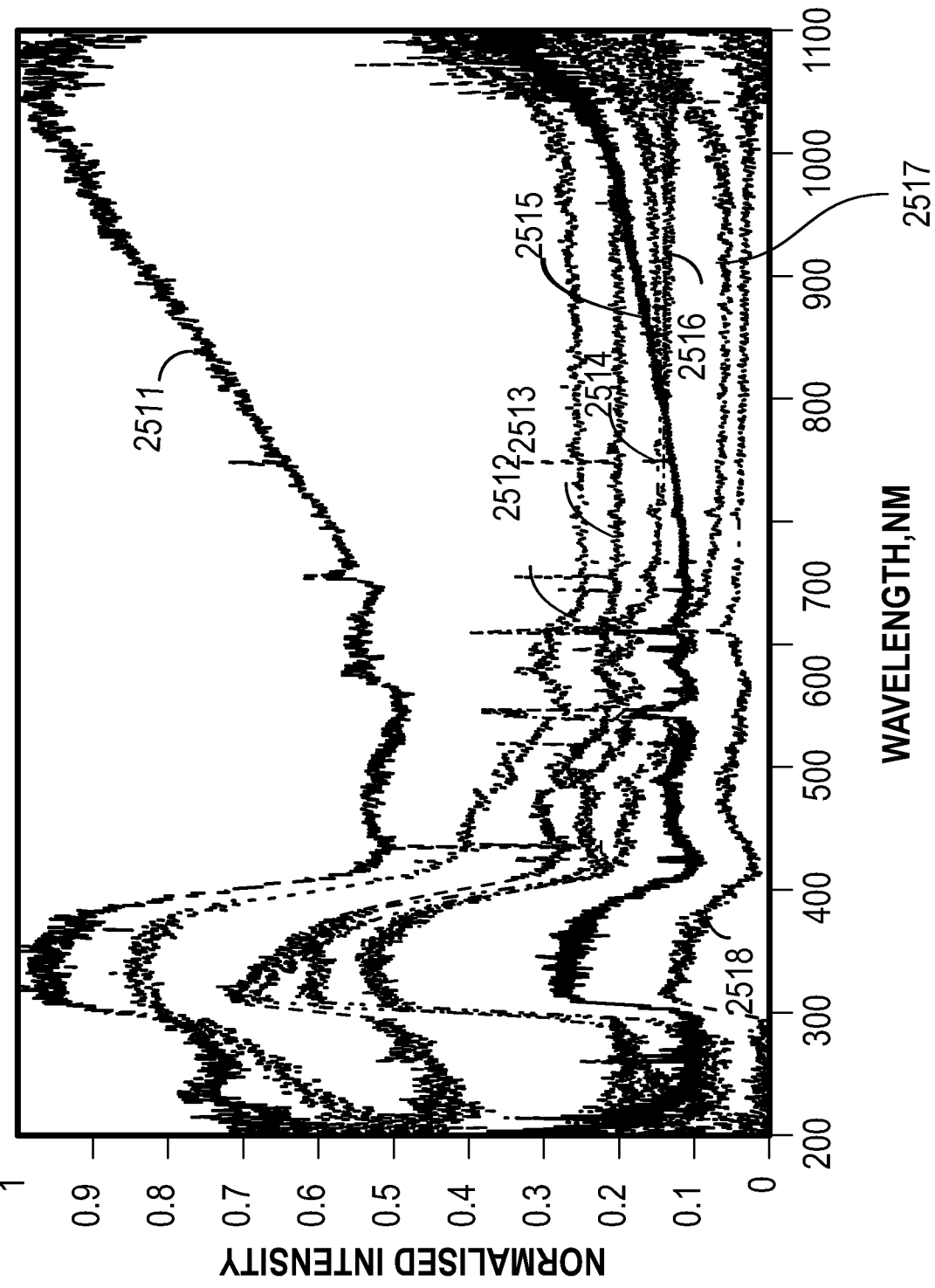
FIGS. 25A-25B illustrate an impact of distances between the tissue and spectroscopic probe distal end on the spectra of the reflect light from the target.
Figure 25B:
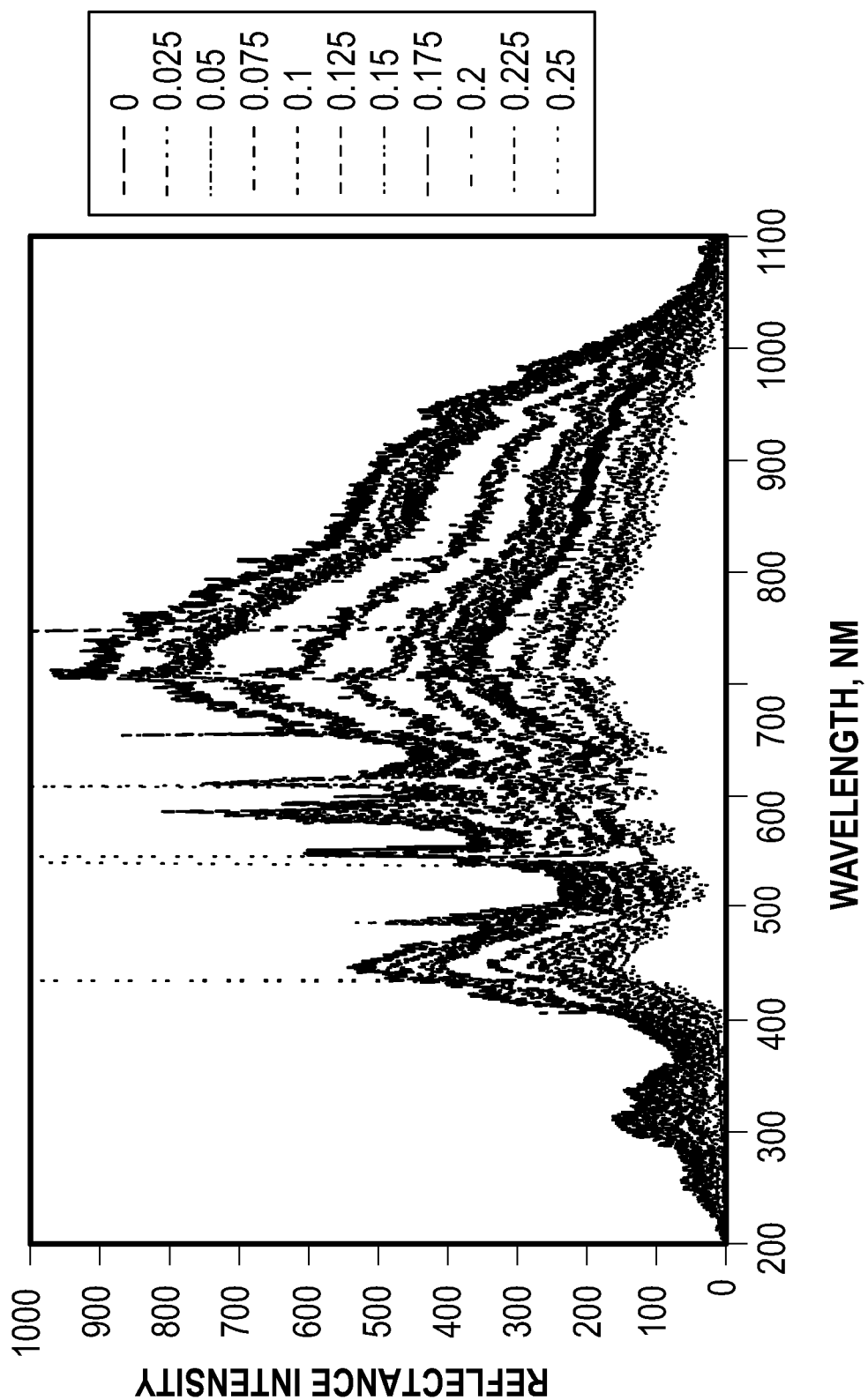

FIGS. 25A-25B illustrate an impact of distances between the tissue and spectroscopic probe distal end on the spectra of the reflect light from the target. FIG. 25A illustrates exemplary normalized UV-VIS reflection spectra of various soft tissue types, including bladder endothelial spectra 2511, stomach endothelial spectra 2512, stomach smooth muscle spectra 2513, under ureter spectra 2514, ureter endothelial 2515, calyx spectra 2516, bladder muscle spectra 2517, and medulla spectra 2518. FIG. 25B illustrates exemplary UV-VIS reflection spectra of a particular tissue recorded at different distances between the tissue and spectroscopic probe distal end, such as from 0 to 0.25 inch. FIG. 25A shows some examples of animal soft tissue spectra. FIG. 25B presents exemplary UV-VIS reflection spectra of a tissue recorded at different distances between the tissue and spectroscopic probe distal end. In this example, the reflected signal intensity at two spectra maximums of 450 nm and 730 nm were measured at different distances between the target tissue and spectroscopic probe distal end presented, as discussed above with reference to FIGS. 24A-24B.

Laser Controller 1740

The laser controller 1740 can be integrated with a Laser Coupling System. The Laser Coupling System couples one or more laser modules (e.g., solid-state laser modules) into a fiber. The Laser Controller 1740 may be coupled to the Feedback Analyzer 1730, which may send the optimized signal with the suggested settings directly to the laser controller 1740 (automatic mode), or request operator approval to adjust the laser settings (semi-automatic mode). FIG. 17 is a schematic diagram of a fully automated Laser System. FIG. 18 is a schematic diagram of a semi-automated Laser System where the System requires user approval, such as via a user interface including an input 1850 and a display 1860. In an example, the laser settings may be adjusted within a set range, which in an example maybe predetermined by the user at the start of the procedure.

Figure 19A:
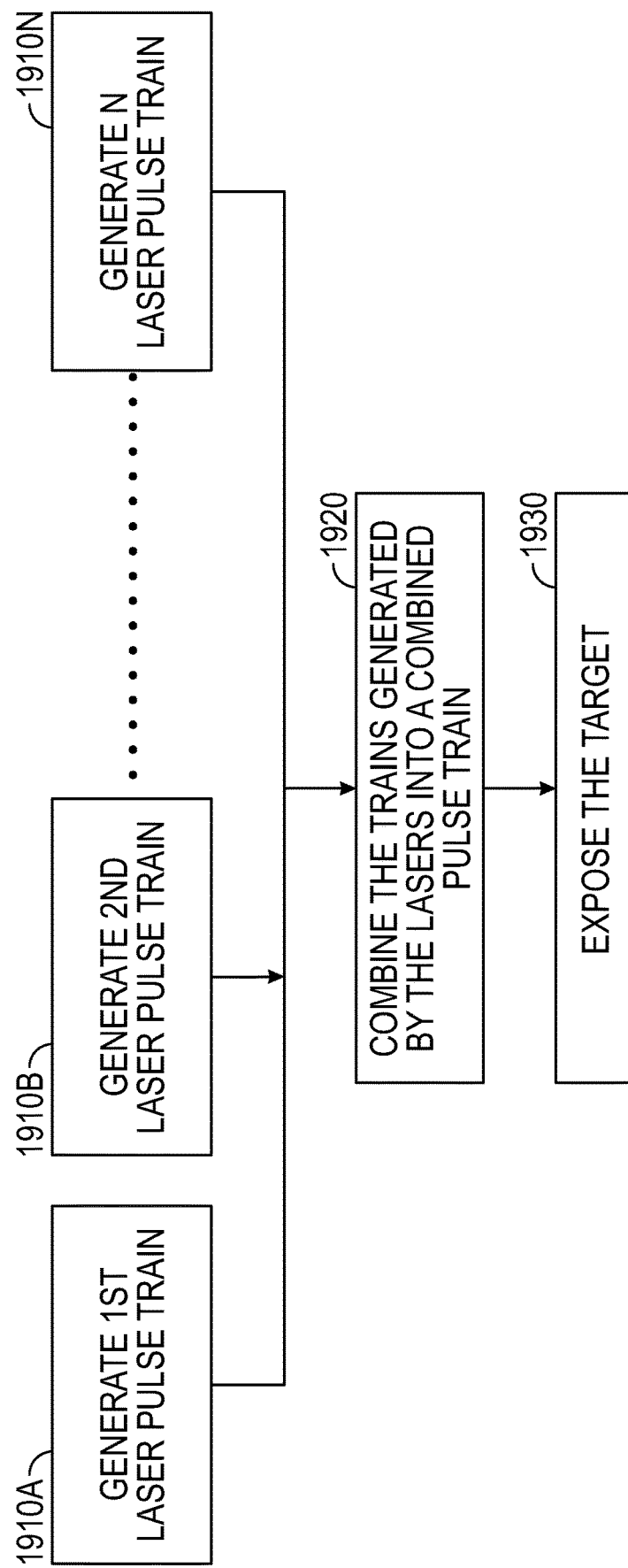
FIGS. 19A-19B illustrates examples of a combined laser pulse train generated using a number of (e.g., N) laser pulse trains.
Figure 19B:
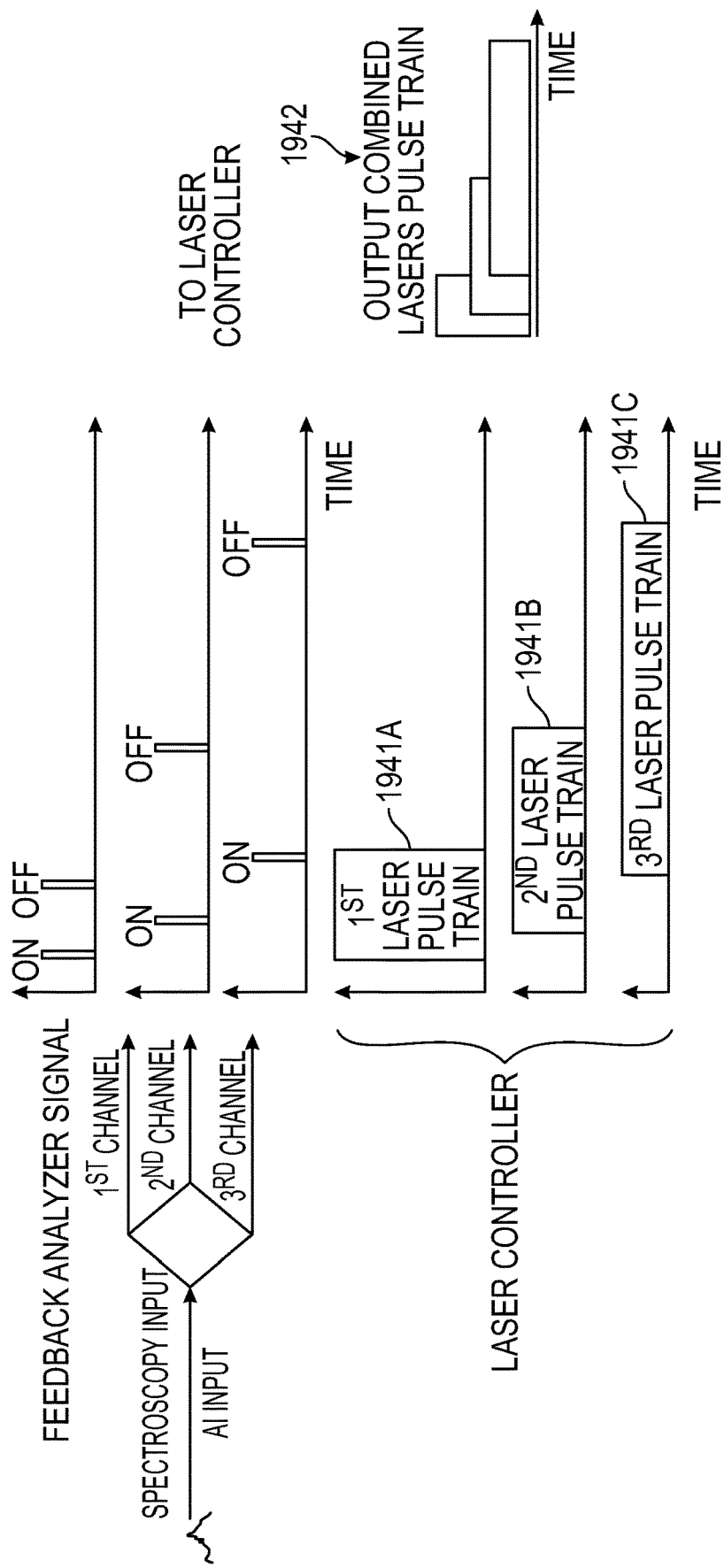

In some examples, the Lasers Controller 1740 may combine two or more laser pulse trains to create a combined laser pulse train. FIG. 19A illustrates an example where the laser controller 1740 may generate a number of (e.g., N) laser pulse trains 1910A-1910N, combine the laser pulse trains 1910A-1910N into a combined pulse train 1920, and expose the target with the combined pulse train at 1930. FIG. 19B is a diagram illustrating an example of an output laser pulse train 1942 combined from the three different laser trains 1941A, 1941B, and 1941C emitting from different Laser Modules. As illustrated therein, the laser trains 1941A, 1941B, and 1941C may be turned on at different times, and/or turned off at different times, in accordance with the feedback analyzer signal. In the example as illustrated therein, the output combined laser pulse train 1942 may include portions where two or more of the laser trains 1941A, 1941B, and 1941C overlap in time.

With the combination of the laser modules 1910A-1910N, spectroscopy system 1720, and the feedback analyzer 1730, the laser feedback system 1740 as described herein can continuously identify the composition of a target through an endoscope and update the laser settings throughout a procedure.

The main components of the Laser System may be easily customized depending on the targeted medical procedure. For example, the Laser Controller 1740 supports different lasers types and their combination. This allows a wider range of output signal options including power, wavelength, pulse rates, pulse shape and profile, single laser pulse trains and combined lasers pulse trains. The operating mode of the Laser System may be automatically adjusted, or suggested for each desired optical effect. The Spectroscopic System collects information about the target materials that is useful for diagnostic purposes, and for confirming that laser parameters are optimal for the target. The Feedback Analyzer 1730 may automatically optimize operation mode of the laser system and reduces risk of human mistake.

Internet of Things (IoT) System 1750

In some examples, the laser system may include an optional IoT system 1750 that supports storing the spectral database library on a cloud 1752, supports quick access to the spectra and optimal setup database library, and enables communication between the cloud 1752 and Feedback Analyzer 1730. The cloud storage of data supports the use of artificial intelligence (AI) techniques to provide input to the Feedback Analyzer 1730, and supports immediate access to algorithm and database improvements.

According to various examples described herein, the IoT system 1750 may include a network where the components of the Laser System can communicate and interact the others over the Internet. IoT supports quick access to the spectra database library stored on a cloud 1752 and performs communication between the cloud 1752 and feedback analyzer 1730. In addition, all of the components of the Laser System may be remotely monitored and controlled if need through the network. An example of such successful connection is the Internet of Medical Things (also called the Internet of Health Things) is an available application of the IoT for medical and health related purposes, which include data collection and analysis for research, and monitoring.

In various examples, the IoT system 1750 may support access to various cloud resources including cloud-based detection, recognition, or classification of a target structure (e.g., calculi structures or anatomical tissue). In some example, a machine learning (ML) engine may be implemented in the cloud 1752 to provide services of cloud-based target detection, identification, or classification. The ML engine may include a trained ML model (e.g., machine-readable instructions executable on one or more microprocessors). The ML engine may receive target spectroscopic data from the Laser system or retrieve target spectroscope data stored in the cloud 1752, perform target detection, identification, or classification, and generate an output such as a label representing a tissue type (e.g., normal tissue or cancerous lesion, or tissue at a particular anatomical site) or a calculus type (e.g., kidney, bladder, pancreobiliary, or gallbladder stone having a particular composition). The target spectroscopic data, among other clinical data collected from the patient before or during a procedure, may be automatically uploaded to the cloud 1752 at the end of the procedure or other scheduled time. Alternatively, a system user (e.g., a clinician) may be prompted to upload the data to the cloud 1752. In some examples, the output may additionally include a probability of the target being identified as tissue or calculi, or a probability of the target being classified as a particular tissue type or a calculus type. A system user (e.g., a clinician) may use such cloud services to obtain near real-time information about target tissue or calculi in vivo such as while performing an endoscopic laser procedure.

In some examples, the ML engine may include a training module configured to train a ML model using training data such as stored in the cloud 1752. The training data may include spectroscopic data associate with target information, such as a tag identifying target types (e.g., calculi types, or tissue types). The training data may include lab data based on spectroscopic analysis of a variety of tissue types and/or calculi types. Additionally or alternatively, the training data may include clinical data acquired from multiple patients in vitro or in vivo. In some examples, patient-identifying information can be removed from the patient clinical data (e.g., spectroscopic data) prior to such data being used uploaded to the cloud 1752 to train the ML model or to perform target detection, identification, or classification using a trained ML model. The system may associate the de-identified patient clinical data with a tag identifying source of data (e.g., hospital, laser system identification, procedure time). The clinician may analyze and confirm target type (e.g., calculi or tissue type) during or after the procedure, and associate the target type with the de-identified patient clinical data to form the training data. Using the de-identified patient clinical can advantageously increase the robustness of the cloud-based ML model as additional data from a large patient population can be included to train the ML model. This may also enhance the performance of the ML model to recognize rare calculi types as the spectroscopic data from rare calculi types are difficult to obtain clinically or from a lab.

Various ML model architectures and algorithms may be used, such as decision trees, neural networks, deep-learning networks, support vector machines, etc. In some examples, the training of the ML model may be performed continuously or periodically, or in near real time as additional spectroscopic data is made available. The training involves algorithmically adjusting one or more ML model parameters, until the ML model being trained satisfies a specified training convergence criterion. The resultant trained ML model may be used in cloud-based target detection, recognition, or classification. With a ML model trained by exploiting large volume of data stored in the cloud 1752 and additional data constantly or periodically added thereto, the ML based target recognition with cloud connection as described herein may improve the accuracy and robustness of in vivo target detection, recognition, and classification.

Example Endoscopic Laser System

FIGS. 21A-21D illustrate examples of an endoscopic laser system 2100A and 2100B comprising an endoscope 2110 with an integrated multi-fiber accessory, and a surgical laser system comprising the feedback-controlled laser treatment system 1010 and the laser source 1020, as illustrated in FIG. 10A. Alternatively, a spectroscopic response may be collected and delivered to the spectrometer by an imaging system containing a detector such as a CCD or CMOS sensor. Target composition analysis may be performed via spectroscopy through one or more of the cores of the multi-fiber accessory while illuminating the target with a light source transmitted through one or more of the other cores of the multi-fiber accessory.

Figure 21A:
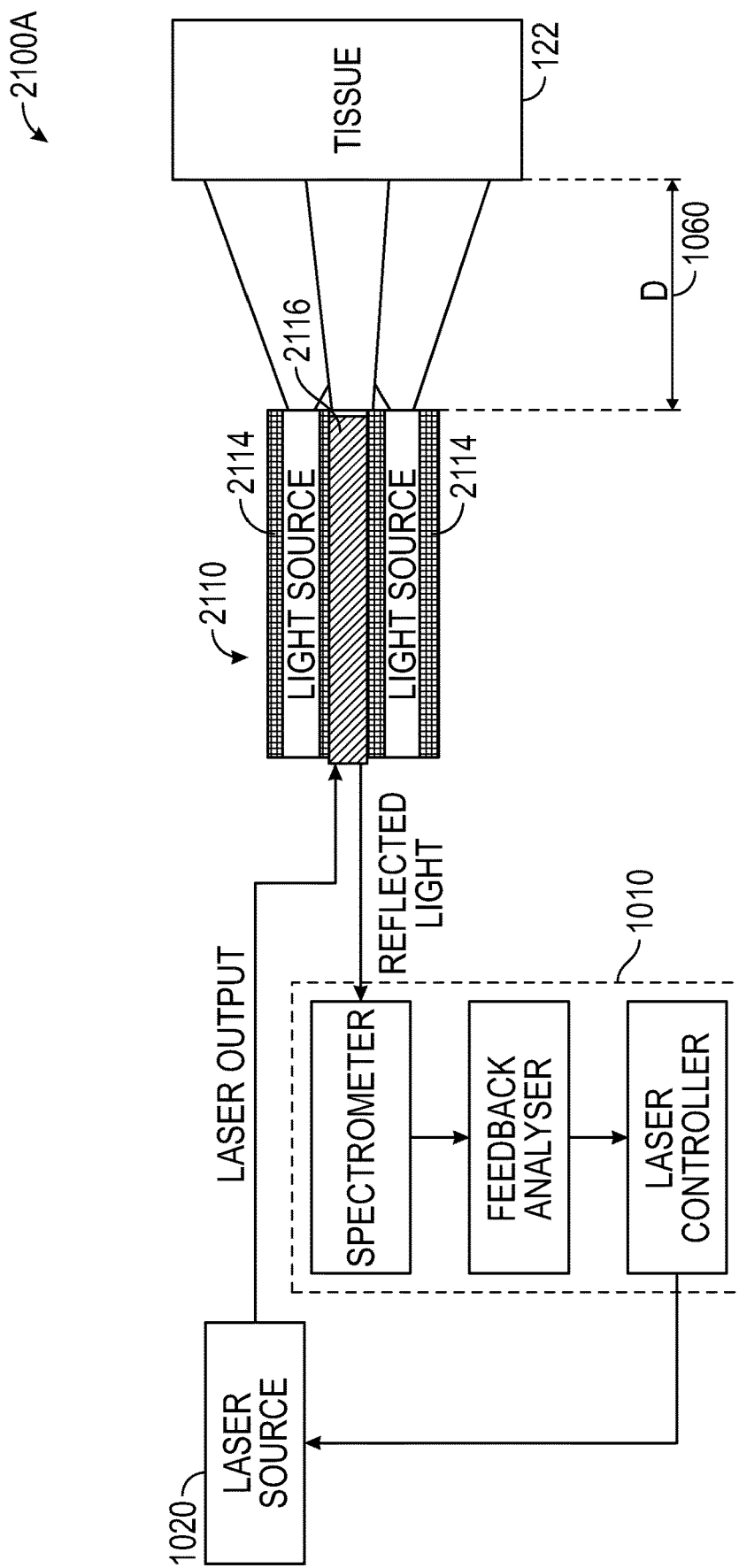
FIGS. 21A-21D illustrate examples of an endoscopic laser system with multi-fiber configuration.

As illustrated in FIG. 21A, the endoscopic laser system 2100A includes a multi-fiber accessory that includes an optical pathway 2116 used for transmitting the spectroscopic signal back to the spectrometer 1011, as well as for delivering surgical laser energy from the laser source 1020 to the target structure. In an example, the optical pathway 2116 includes an optical fiber embedded within and extending along an elongate body of the endoscope 2110. In another example, the optical pathway 2116 includes two or more optical fibers extending along an elongate body of the endoscope 2110. The laser controller 1013 may control the timing of the laser firing such that the transmission of spectroscopic signal and delivery of laser energy occur at different times or simultaneously.

The multi-fiber accessory may include two or more light source fibers 2114 embedded into and extending along an elongate body of the endoscope 2110. By way of example and not limitation, FIG. 21C illustrates a radial cross-sectional view of the elongate body of the endoscope 2110, where a number of light source fibers 2114 and the optical pathway 2116 are longitudinally positioned within the elongate body of the endoscope, and the light source fibers 2114 are radially distributed surround the optical pathway 2116, such as along a circumference with respect to the optical pathway 2116 on the radial cross-section of the elongate body of the endoscope. In the example as shown in FIG. 21C, the optical pathway 2116 may be located at substantially the central longitudinal axis of the elongate body of the endoscope 2110. By way of example and not limitation, six light source fibers may be positioned around the optical pathway 2116, as shown in FIG. 21C. Other number of light source fibers, and/or other positions of the light source fibers relative to the optical pathway 2116, may be used. For example, FIG. 21D illustrates two light source fibers 2114 radially positioned at opposite sides of the optical pathway 2116. The light source fibers 2114 may be coupled to the light source 1030. Alternatively, the light source fibers 2114 may be coupled to the illumination source 914 as shown in FIG. 9A-9B. Light from the endoscope light source, either the illumination source 914 (e.g., one or more LEDs) or the remote light source 1030 such as external to the endoscope, may serve the functions of illuminating the target and producing spectroscopic signal reflected from the target surface which may be collected for spectroscopic analysis. The feedback analyzer 1012 may determine the distance 1060 between the distal end of the endoscope 2110 and the target structure 122, as similarly shown in FIGS. 10-11.

Figure 21B:
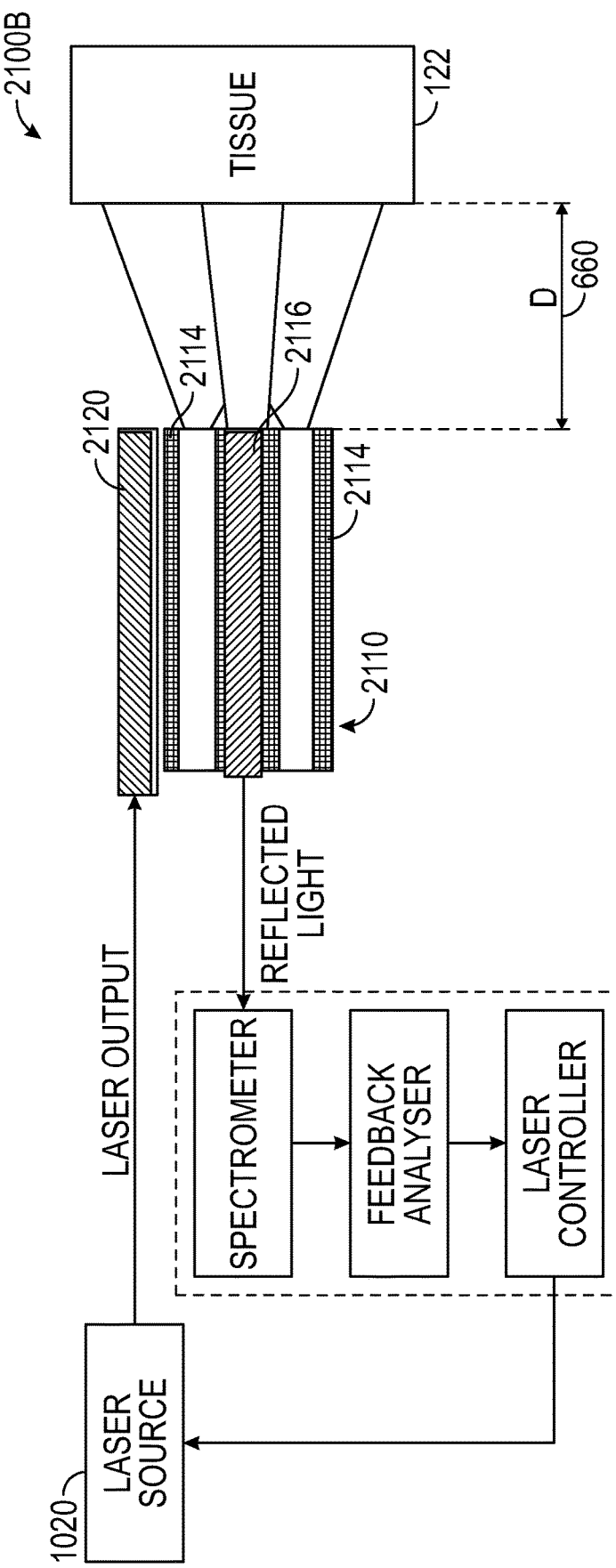
Figure 21D:
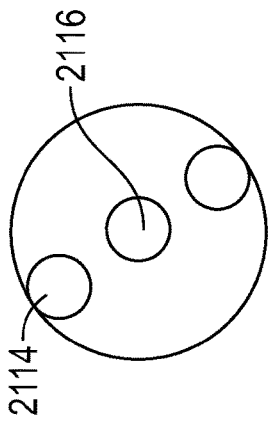
Figure 21C:
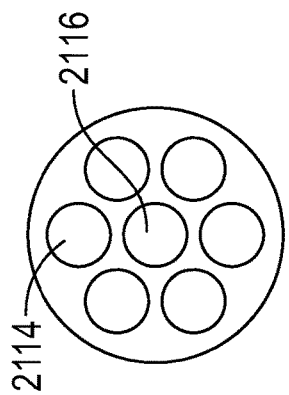

FIG. 21B illustrates an endoscopic laser system 2100B that includes a multi-fiber accessory. Instead of delivering laser energy through the optical pathway 2116, a separate laser fiber 2120 may be used for delivering surgical laser energy from the laser source 1020 to the target structure. The optical pathway 2116 is used as a dedicated spectroscopy signal fiber for transmitting the spectroscopic signal back to the spectrometer 1011.

Figure 22:
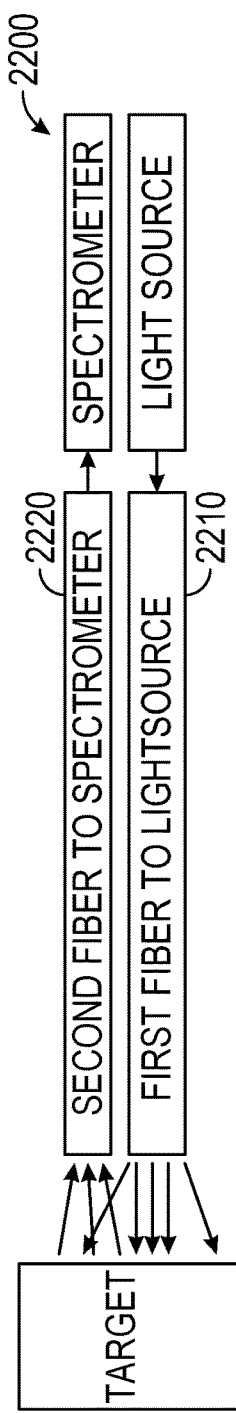
FIG. 22 is a block diagram illustrating an example of a multi-fiber system as used in a spectroscopic fiber delivery system.
Figure 23A:
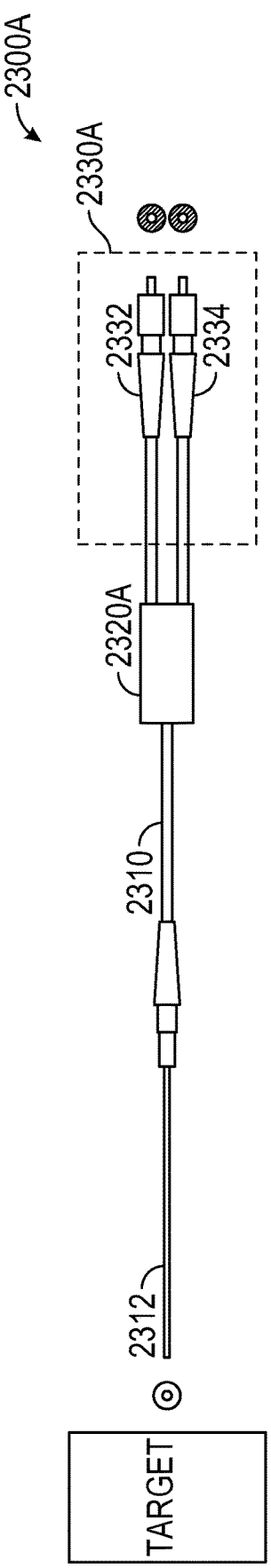
FIGS. 23A-23B illustrate examples of a multi-fiber accessory with source light input and spectroscopy feedback signal.
Figure 23B:
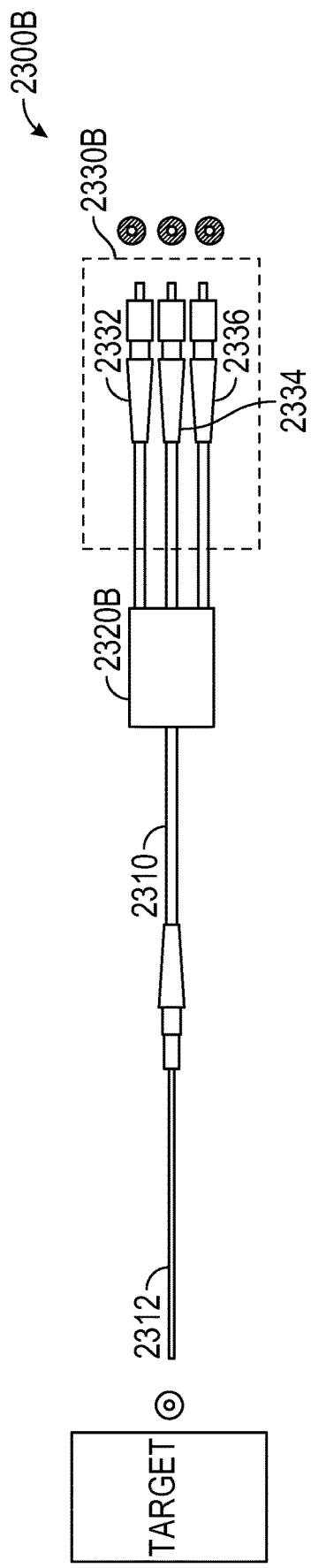

FIGS. 22 and 23A-23B illustrate examples of the multi-fiber system that may be used in a spectroscopic fiber delivery system, such as that discussed above with reference to FIGS. 21A-21D. In the example as illustrated in FIG. 22, a multi-fiber system 2200 includes a first fiber 2210 coupled to the light source and configured to direct illumination light at the target, and a separate second fiber 2220 coupled to the spectrometer and configured to transmit the reflected signal (e.g., light reflected from the target) indicative of spectroscopic properties of the target to the spectrometer.

FIGS. 23A-23B are diagrams of an exemplary multi-fiber accessory with source light input and spectroscopy feedback signal. As shown in FIG. 23A, a multi-fiber accessory 2300A may include a distal portion 2310, a transition section 2320A, and a proximal portion 2330A. The distal portion 2310 includes a shaft that can be sized and shaped to enclose the first and second fiber 2210 and 2220, and a transition section 2320A proximal to the distal portion 2310. The first fiber 2210 and second fiber 2220 may be embedded in and extend along a longitudinal shaft of the distal portion 2310. The shaft can be sized and shaped to extend through a working channel of an endoscope. In some examples, the first fiber 2210 may include two or more optical fibers each coupled to the light source, and/or the second fiber 2220 may include one or more optical fibers. In some examples, as illustrated in FIGS. 21C-21D, the second fiber 2220 can be radially distributed surrounding the first optical fibers 2210. In an example, at least one of the second optical fibers 2220 can extend along a substantially central longitudinal axis of the shaft. The two or more first optical fibers 2210 can be radially positioned at opposite sides of the second optical fiber 2220 extending along the central longitudinal axis of the shaft.

The proximal portion 2330A comprises a first connector 2332 configured to be connected to the light source, and a second connector 2334 configured to be connected to a spectrometer. The transition section 2320A interconnects the distal portion 2310 and the proximal portion 2330A, and can be configured to couple the first connector 2332 to the first fiber 2210 and the second connector 2334 to the second fiber 2220. As such, the transition section 2320A provides a transition of the optical fibers 2210 and 2220 from the respective first and second connectors 2332 and 2334 into the single shaft.

The shaft can include an insertable distal end 2312 extended distally from the distal portion 2310. The insertable distal end 2312 can be configured to be inserted into a patient. The proximal portion 2300A can be associated with (e.g., included within) a handle for a user to operate the multi-fiber accessory 2300A. In an example, at least a portion of the multi-fiber accessory 2300A (e.g., one or more of the distal portion 2310, the transition section 2320A, or the proximal portion 2330A) can be included in or insertable into a working channel of an endoscope.

FIG. 23B illustrates another example of multi-fiber accessory 2300B, which is a variant of the multi-fiber accessory 2300A. In the example illustrated in FIG. 23B, the proximal portion 2330B may further include a third connector 2336 configured to couple a laser source to one of the optical fibers 2210 or 2220. Similar to FIG. 23A, a transition section 2320B interconnects the distal portion 2310 and the proximal portion 2330B. Laser energy generated from the laser source may be transmitted from the proximal portion 2330B to the distal portion 2310, through one of the optical fibers 2210 or 2220, and delivered to a target treatment site via the insertable distal end 2312. In some examples, the multi-fiber accessory 2300B may further include a laser fiber different from the optical fibers 2210 or 2220. The laser fiber may be positioned in the working channel of the endoscope, such as within the shaft. Laser energy generated from the laser source may be transmitted to the distal portion 2310 through the laser fiber.

Example Applications of the Laser System

The Laser System as described in accordance with various examples in this document can be used in many applications such as endoscopic hard or soft tissue surgery to improve the effectiveness of ablation, coagulation, vaporization, or other laser effects.

One application of the Laser System for tissue surgery application is with regard to using the laser system to provide effective tissue ablation and coagulation, instead of using two different foot pedals as is often done on commercial devices such as lasers and plasma devices. An example system utilizes two or more solid-state Laser Modules emitting at two different wavelengths coupled through the fibers into Laser Controller, and a UV-VIS reflection Spectroscopic System that deliver spectral signals to the Feedback Analyzer that suggests alternate settings to a user before being adjusted.

In one examples, two Laser Modules may be provided, including a first laser module that can emit at a high tissue absorption optical wavelength for more efficient ablation/carbonation processes, and a second laser module that can emit at a lower tissue absorption optical wavelength for more efficient coagulation such as due to a penetration depth that similar to the diameter of a small capillary. Examples of the first laser module may include a UV-VIS emitting InXGa1-XN semiconductor laser: GaN—emission 515-520 nm; InXGa1-XN—emission 370-493 nm or the IR laser that emit in the high water absorption range, 1900-3000 nm and that summarized in Table 1. Examples of the second Laser Module may include GaXAl1-XAs with emission 750-850 nm, or InXGa1-XAs with emission 904-1065 nm. Both first and second Laser Modules may be coupled into the Laser Controller with laser coupling system.

A spectroscopic light source may be integrated into a separate fiber channel, laser fiber or endoscope system. A spectroscopic light source signal reflected from the target may be rapidly detected and delivered to the spectrometer though a separate fiber channel or laser fiber. Alternatively, the Spectroscopy System could collect spectroscopic signals from an imaging system containing a detector such as a CCD or CMOS sensor. Based on the Spectroscopic system feedback, the Signal Analyzer may detect target material composition and suggest first or second Laser Modules setup to achieve effective tissue treatments, and deliver signals to an output system used to provide suggested setup information to the user.

This example allows for tissue ablation and coagulation by utilizing two or more laser pulses with optical wavelengths controlled by a Feedback Analyzer system. However, feedback control may be utilized with a single or multiple optical wavelength systems to optimize the simultaneous delivery of specific effects to targets. These effects may be simultaneous only from the perspective of the user; features as described herein are not limited to delivering wavelengths at exactly the same time.

An example time operating chart of this laser with spectroscopic feedback presented in FIG. 8. As described therein, optical feedback signals with amplitude $A_{max}$ are continuously delivered to and reflected from the target surface and are detected and analyzed by the signal analyzer. Then the user may turn ON the first laser, or keeps the first laser ON after selecting to ablate soft tissue, while the second laser is OFF. During operation of the first laser, the optical feedback signal is highly absorbed by carbonized tissue until its amplitude reduces to a threshold level, $A_{min}$. The signal analyzer then changes the state of the lasers such that the first laser is turned OFF and the second laser is turned ON. The second laser is highly absorbed by carbonized tissue; so the carbonized tissue is ablated, effectively removing the carbonization. The wavelength of the second laser also provides effective coagulation. Due to the decarbonization process, the amplitude of the optical feedback pulses returns close to the initial level, $A_{max}$. When this occurs, the signal analyzer changes the state of the lasers back to the first laser being turned ON and the second laser being turned OFF. The above process can be repeated until the required amount of tissue ablation and coagulation is achieved.

Another application of the Laser System is with regard to efficient laser lithotripsy process to fragment a kidney or bladder stone in a patient. The application relates to a process using multi wavelength lasers energy having a wavelength with less absorption by the target to heat a target first and then a stronger absorption wavelength to fragment the target, such as a kidney stone for example. During laser lithotripsy, the kidney or bladder stone fragmentation can occur due to a photothermal effect. High laser energy can be absorbed by the stone, thus causing a rapid temperature rise above the threshold for chemical breakdown resulting in its decomposition and fragmentation. In one example, a laser lithotripsy can include a two-stage process. The first stage is a pre-heating stage, where a stone is heated using laser energy of a first wavelength that causes lower laser energy absorption by the stone. A subsequent second stage involves an application of laser energy with a second wavelength, which causes a stronger laser energy absorption by the stone than the first wavelength. Such a multistep process allows better controlling vapor bubble creation and reducing strength of generated shock waves over the fragmentation process (reduces stone retropulsion effect).

In an example, the Laser System utilizes two or more solid-state Laser Modules emitting at two different wavelengths coupled through the fibers into Laser Controller, and a Spectroscopic System that deliver spectral signals to the Feedback Analyzer that suggests alternate settings to a user before being adjusted. A first Laser Module can emit at a lower stone/water absorption optical wavelength for efficient pre-heating; and a second Laser Module can emit at a high stone/water absorption optical wavelength for more efficient stone fragmentation. The first Laser Module in this application may produce an output at a lower stone or water absorption wavelength. This laser provides effective and uniform stone pre-heating. Examples of the first laser source for the first Laser Module may include GaXAl1−XAs with emission 750-850 nm, or InXGa1−XAs with emission 904-1065 nm. Examples of the second laser source may inlcude a UV-VIS laser emitting InXGa1−XN semiconductor laser, such as GaN laser with emission 515-520 nm, or InXGa1−XN laser with emission 370-493 nm, or the IR laser that emit in the high water and stone absorption range, 1900-3000 nm, and that summarized in Table 1.

Both first and second Laser Modules may be coupled into the Laser Controller with laser coupling system. A spectroscopic light source may be integrated into a separate fiber channel, laser fiber or endoscope system. A spectroscopic light source signal reflected from the target may be rapidly detected and delivered to the spectrometer though a separate fiber channel or laser fiber. Alternatively, the Spectroscopy System may collect spectroscopic signals from an imaging system containing a detector such as a CCD or CMOS sensor.

Based on the Spectroscopic system feedback, the Signal Analyzer may detect target material composition and suggest first or second Laser Modules setup to achieve effective multistep stone treatments process and delivers signals to an output system used to provide suggested setup information to the user. The Laser System may simultaneously deliver effective stone preheating and fragmentation by utilizing two or more laser pulses from Laser Modules with optical wavelengths controlled by a Feedback Analyzer system. However, feedback control may be utilized with a single or multiple optical wavelength systems to optimize the simultaneous delivery of specific effects to target stone composition.

Yet another application of the Laser System is with regard to a process to perform ablation of hard tissue, for example teeth, bone etc., where high laser output power is required. The effectiveness of soft tissue laser surgery based on the low-temperature water vaporization at 100° C., however, a hard tissue cutting process require very high ablation temperatures, as high as 5,000° C. To deliver enhanced output power the Laser System may couple larger number of Laser Modules to increase an integrated output power to the level that enough to treat the target. The following lasers may be used as emitting sources: UV-VIS emitting InXGa1−XN semiconductor laser: GaN—emission 515-520 nm; InXGa1−XN—emission 370-493 nm or the IR laser 1900-3000 nm and that summarized in Table 1. The laser sources for the Laser Modules applicable to this example may include, for example, GaXAl1−XAs laser with emission 750-850 nm, or InXGa1−XAs laser with emission 904-1065 nm.

The Laser Modules may be integrated into the Laser Controller with laser coupling system. To archive the require high power the large number of a Laser Modules can be coupled into the System. A spectroscopic light source may be integrated into a separate fiber channel, laser fiber or endoscope system. A spectroscopic light source signal reflected from the target can be rapidly detected and delivered to the spectrometer though a separate fiber channel or laser fiber. Alternatively, the Spectroscopy System could collect spectroscopic signals from an imaging system containing a detector such as a CCD or CMOS sensor.

Based on the Spectroscopic System feedback the Signal Analyzer may detect target material composition and suggest Laser Modules setup and number of Laser Modules to achieve the required output power, effective multistep treatments process, and deliver signals to an output system used to provide suggested setup information to the user. The Laser System may simultaneously deliver required high laser output power by increasing number of the Laser Modules involved into the treatment process utilizing two or more laser pulses with optical wavelengths controlled by a Feedback Analyzer system. The feedback control may be utilized with a single or multiple optical wavelength systems to optimize the simultaneous delivery of specific effects to target stone composition. These effects may be simultaneous only from the perspective of the user; but is not limited to delivering wavelengths at exactly the same time.

Features as described herein may be used to provide a method to identify the composition of a target. The target may, in some instances be a medical target, such as soft and hard tissue in vivo through the use of a surgical accessory. This accessory may be used endoscopically or laproscopically. The accessory may consist of a single device containing multiple optical fibers with the intention that at least one fiber supplies a source illumination and at least one fiber to guide reflected light to a spectrometer. This allows a user to continuously monitor a composition of tissue or a target with or without the use of direct endoscopic visualization throughout a procedure. This also has the ability to be used in combination with a laser system where the accessory may send feedback to the laser system to adjust the settings based on the composition of the tissue or target. This feature will allow for the instant adjustment of laser settings within a set range of the original laser setting selected by the user. Features as described herein may be used with a spectroscopy system, which may be used with an optical fiber integrated laser system. A spectroscopic light source may be transmitted through at least one of the fibers in the multi-fiber accessory. A light source signal reflected from the target may be rapidly collected and delivered to the spectrometer via an additional fiber in the multi-fiber.

An example method may utilize spectroscopic input data to calculate and control the distance between a distal end of laser delivery system 1701 (such as a fiber) and a tissue or target based on an algorithm. The method may be applied to both soft and hard tissue types for in vivo surgery process. The distance between the target and the distal end of the fiber may be calculated based on analyses of spectral data. Outer diameter of each fiber and its angle of protrusion from the endoscope affects the intensity of reflected light; that is measured to obtain spectral data. With features as described herein, a distance may be calculated without sequentially illuminating by the lights with different numerical aperture values.

In the case of mobile calculi, the method may control the distance and may adjust or suggest laser-operating parameters that creates a suction effect using vapor bubbles in water to pull targets that are beyond a predetermined threshold closer to the distal end of the fiber. This feature minimizes the effort users need to exert to maintain an effective treatment distance with mobile targets.

The UV-VIS-IR reflection spectroscopy in accordance with various examples discussed in this document can be used alone or in combination with other spectroscopic techniques to create the spectroscopic feedback including analyzes of material chemical composition and measure reflected light intensity during in vivo diagnostic or therapeutic procedure. The reflected light may yield the same information as the eye or color image made by high-resolution camera, but it does more quantitatively and objectively. The reflection spectroscopy offers information about the material since light reflection and absorption depends on its chemical composition and surface properties. It is also possible using this technique to get unique information about both surface and bulk properties of the sample.

Yet another application of the Laser System is with regard to a process to identifying target type, such as determining composition of a calculi target during laser lithotripsy. According to some examples discussed herein, an endoscope system has a light source, and the light source provides an illumination light to the target in a human body thorough a light guide of the endoscope. A physician uses the laser system for breaking stones under the illumination light from the endoscope system. This situation may cause some trouble if the laser system is used for detecting stone composition. The light reflected from the stones is weak and, on the other hand, the illumination light from the endoscope system is strong. Therefore, it may be hard to analyze the composition of stones under illuminating by the endoscope system.

Figure 26:
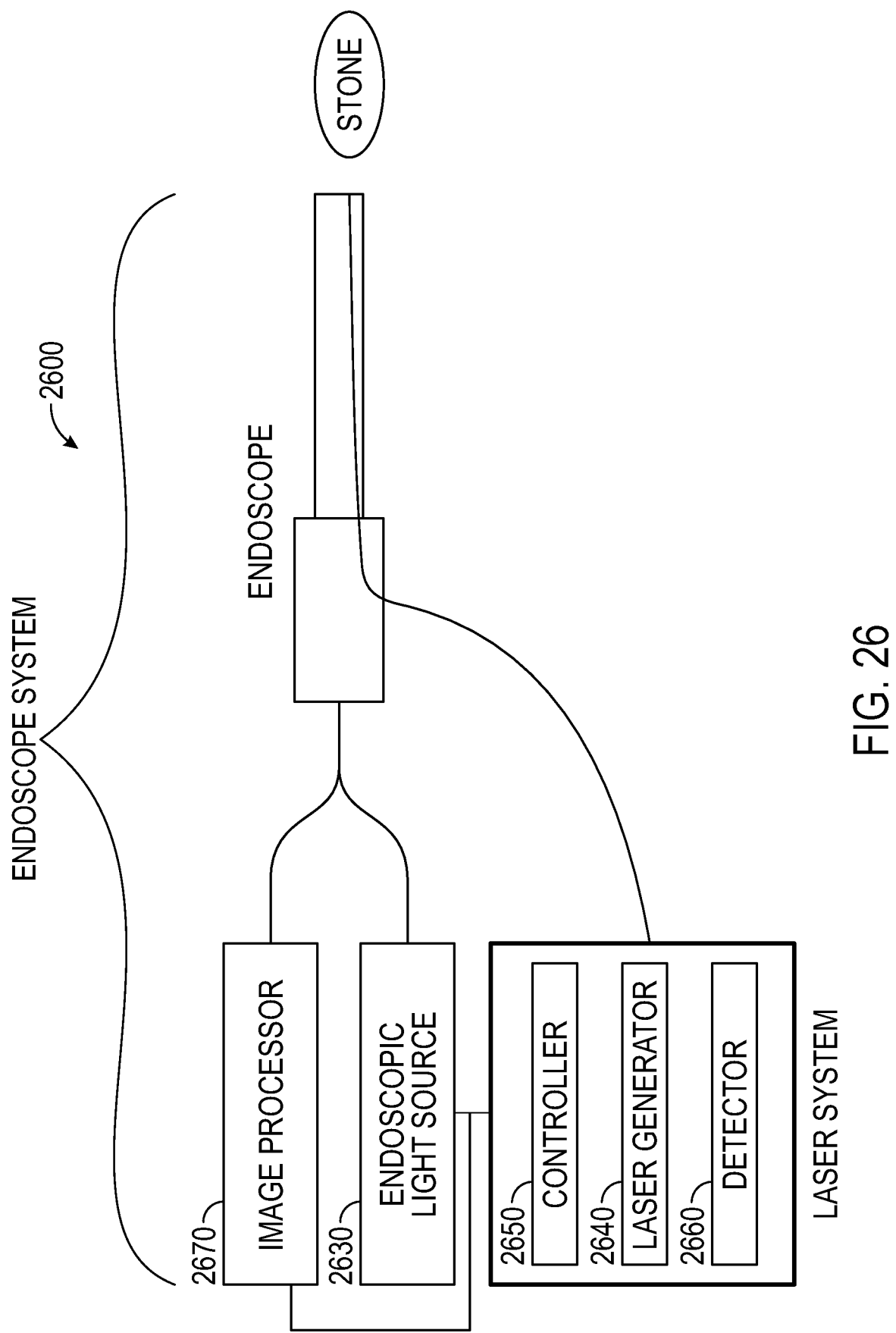
FIG. 26 illustrates an example of an endoscope system for identifying a target using a diagnostic beam such as a laser beam.

FIG. 26 illustrates an example of an endoscope system 2600 configure to identify a target (e.g., to identify composition of a calculi target) using a diagnostic beam such as a laser beam. The system 2600 may include a controller 2650 than can control both of an endoscopic light source 2630 and a laser generator module 2640. The controller 2650 may detect the input of a command to activate the stone composition detecting mode by the physician through the laser system. The controller 2650 may then send a command to the endoscopic light source 2630 to stop illuminating, or switch from a high-illumination mode to a low-illumination mode where a reduced amount of illumination is projected onto the target for a certain period. During such low-illumination or no-illumination period, the laser system 2640 may emit a laser beam to the target and receive the reflected light from the stone. The detector 2660 may perform target identification using the reflected light. By dimming the illumination at the target site under the low-illumination mode (or turning off the illumination), reflection from the target of the laser beam incident on the target can be enhanced, which can help improve target identification.

Once the detector 2660 determines that the target identification is completed, the detector 2660 may send a termination command to the controller 2650. The controller 2650 may then send a command to re-illuminate the target, or switch from the low-illumination back to a high-illumination mode. In one example, when the endoscopic light source 2630 receives the command to stop illuminating or switching from the high-illumination mode to the low-illumination mode, an image processor 2670 in the endoscope system 2600 may capture a still image of the target, and display the still image on the monitor of the endoscope system during the time period. Variations of the endoscope system 2600 for identifying a target have been contemplated, such as those discussed above with reference to FIGS. 11A-11B.

Figure 27:
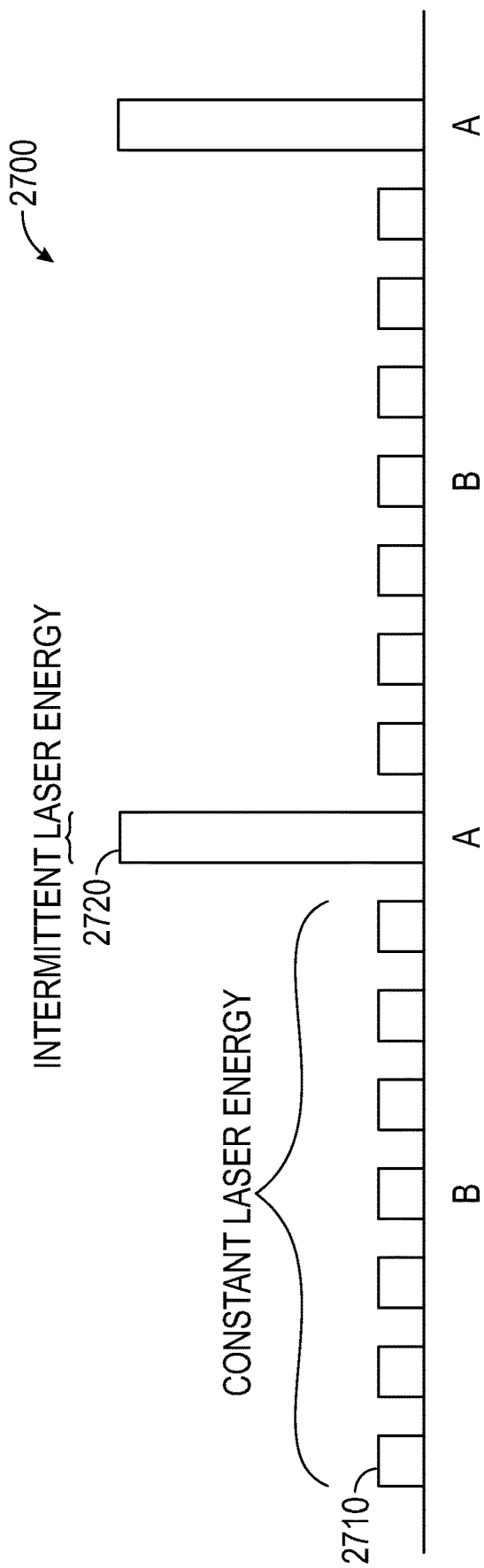
FIG. 27 illustrates a graph of a sequence of laser pulses having different pulsed energy or power levels for use in laser treatment of target tissue or calculi structures.

FIG. 27 illustrates a graph 2700 of a sequence of laser pulses having different pulsed energy or power levels, such as can include a first pulse train 2710 and a second pulse train 2720. Pulses in the second pulse train 2720 have higher energy or power levels than the pulses of the first pulse train 2710. The first pulse train 2710 and the second pulse train 2720 may be generated by respective laser sources, and each emitted from a distal end of an endoscope in forms of respective laser beams. The first pulse train 2710 may be generated substantially constantly in time, such as over a specific time period (e.g., controlled by a user). The second pulse train 2720 may be generated intermittently in time, such as over the specific time period during which the first pulse train 2710 is delivered. For example, the second pulse train 2720 may be delivered between two pulses of the first pulse train 2710, or between two trains of first pulse train 2710. In the example as shown in FIG. 27, pulses in the first pulse train 2710 have a constant energy or power level, and the second pulse train 2720 includes only one pulse with a higher energy or power level than the first pulse train 2710. In some examples, the second pulse train 2720 may include two or more pulses each having a higher energy or power level than the first pulse train 2710.

The sequence of laser pulses as shown in FIG. 27 may be used by a laser lithotripsy system to provide cracking and fragmentation of a calculi structure, such as a kidney for example. As illustrated in FIG. 27, the sequence represents time in the X-direction of the graph, but is also annotated with locations "A" and "B" on the stone or other target. The sequence of the laser pulses thus represents a spatiotemporal pattern of laser pulses with different pulsed energy or power levels. In this example, location "A" is at or near the center of the stone or other target, and location "B" is at or near a periphery of the stone or other target. The laser pulses issued between locations "A" and "B" illustrate pulses that are issued as the laser fiber 140 is being translated from the location "A" to the location "B", or as the laser fiber 140 is being translated from the location "B" to the location "A", such as can include using the actuator. The first pulse train 2710 can be selected to induce a crack in the target stone without fragmenting the target stone. Thus, in FIG. 27, such first pulse train 2710 can be issued beginning at location "A" toward the center of the stone, then proceeding toward location "B" toward a periphery of the stone, and then returning toward location "A" at the center of the stone, at which time a higher energy pulse 2720 can be delivered in a first attempt to fragment the target stone. If such fragmenting by the higher energy pulse 2720 is not successful, then further first pulse train 2710 can be delivered proceeding from locations toward the center of the stone toward a location "B" toward the periphery of the stone, and then returning toward location "A" at the center of the stone, at which time another higher energy pulse 2720 can be delivered in a second attempt to fragment the target stone. Further iterations are also possible. The same or a different location "B" toward the periphery of the stone can be used for the various iterations, with different locations "B" in different iterations producing multiple cracks along such pathways from location "A" to such different peripheral location "B". It may be preferred to use the higher energy pulse 2720 only toward the center of the stone, such as to minimize the effect of the second pulse train 2720 on nearby tissue.

In some examples, the sequence of laser pulses having different pulsed energy or power levels as shown in FIG. 27 may be used by an endoscopic system that provides hemostasis or coagulation at a target site. In an example, the first pulse train 2710 and the second pulse train 2720 may be delivered in a spatiotemporal pattern, such as an alternating fashion in time for example, to the target site to facilitate an efficient hemostasis or coagulation process.

The pulses with different energy or power levels, such as the first pulse train 2710 and the second pulse train 2720, may be controllably activated via an actuator operable by a user, such as a button or a foot pedal. For example, the user may use a first activation pattern (e.g., a single press of the button or the foot pedal) to activate delivery of the first pulse train 2710, and use a second activation pattern (e.g., a double press of the button or the foot pedal) to activate delivery of the second pulse train 2720. In an example, the first pulse train 2710 and the second pulse train 2720 may be controlled via respective separate actuators. Additionally or alternatively, the first pulse train 2710 and the second pulse train 2720, may be controllably activated automatically, such as based on a feedback signal from the target. For example, a spectrometer may collect spectroscopic data of the target, and a feedback analyzer may analyze the spectroscopic data to identify compositions of different portions of a calculi structure. Based at least on such identification, different energy pulses, such as the first pulse train 2710 or the second pulse train 2720, may be delivered to different portions of the target with respectively identified compositions.

Figure 28:
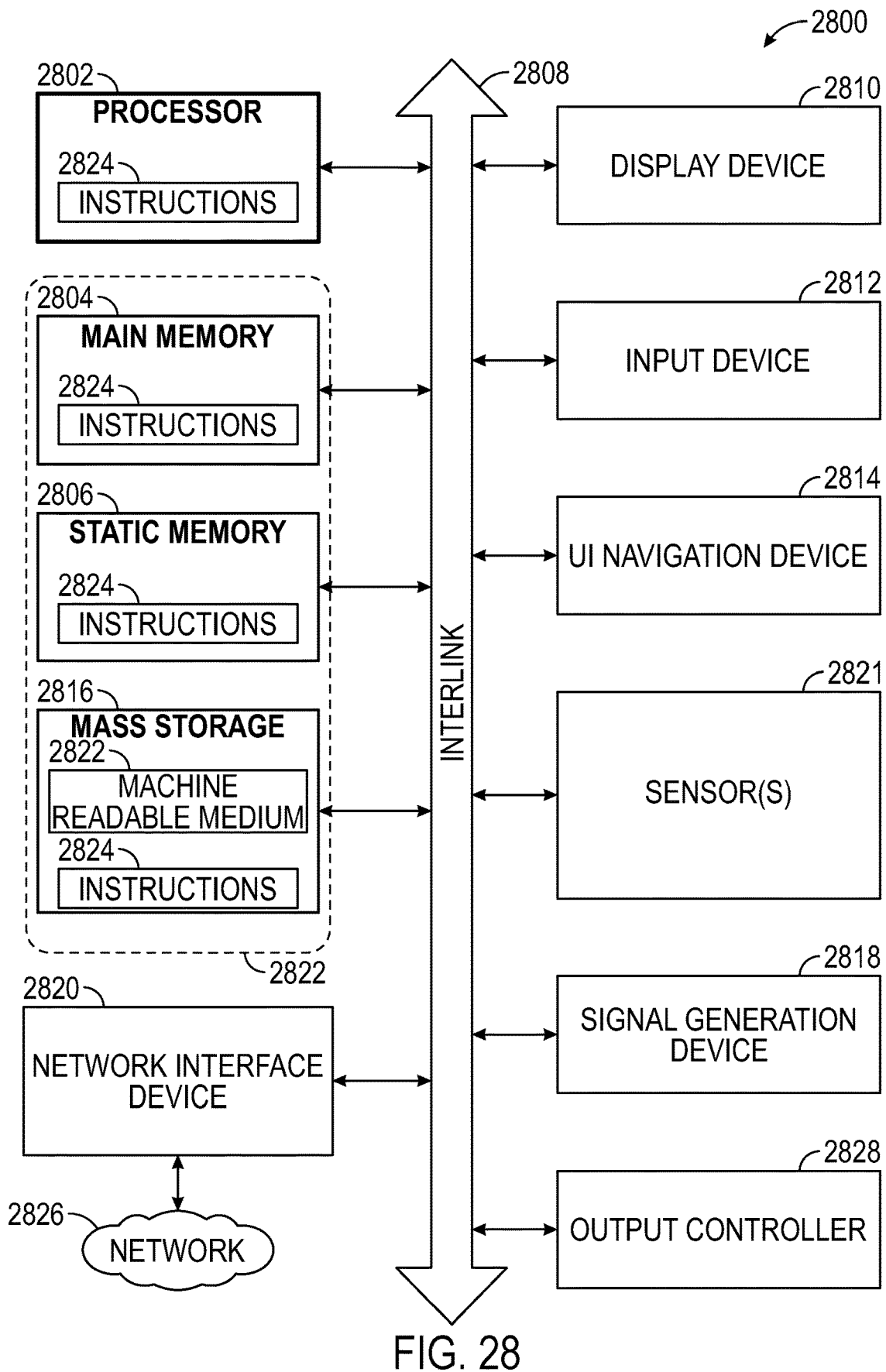
FIG. 28 is a block diagram illustrating an example machine upon which any one or more of the techniques (e.g., methodologies) discussed herein may perform.

FIG. 28 illustrates generally a block diagram of an example machine 2800 upon which any one or more of the techniques (e.g., methodologies) discussed herein may perform. Portions of this description may apply to the computing framework of various portions of the laser treatment system in accordance with examples as discussed in this document.

In alternative embodiments, the machine 2800 may operate as a standalone device or may be connected (e.g., networked) to other machines. In a networked deployment, the machine 2800 may operate in the capacity of a server machine, a client machine, or both in server-client network environments. In an example, the machine 2800 may act as a peer machine in peer-to-peer (P2P) (or other distributed) network environment. The machine 2800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 2800 may include a hardware processor 2802 (e.g., a central processing unit (CPU), a graphics processing unit (GPU), a hardware processor core, or any combination thereof), a main memory 2804 and a static memory 2806, some or all of which may communicate with each other via an interlink (e.g., bus) 2808. The machine 2800 may further include a display unit 2810 (e.g., a raster display, vector display, holographic display, etc.), an alphanumeric input device 2812 (e.g., a keyboard), and a user interface (UI) navigation device 2814 (e.g., a mouse). In an example, the display unit 2810, input device 2812 and UI navigation device 2814 may be a touch screen display. The machine 2800 may additionally include a storage device (e.g., drive unit) 2816, a signal generation device 2818 (e.g., a speaker), a network interface device 2820, and one or more sensors 2821, such as a global positioning system (GPS) sensor, compass, accelerometer, or other sensors. The machine 2800 may include an output controller 2828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 2816 may include a machine readable medium 2822 on which is stored one or more sets of data structures or instructions 2824 (e.g., software) embodying or utilized by any one or more of the techniques or functions described herein. The instructions 2824 may also reside, completely or at least partially, within the main memory 2804, within static memory 2806, or within the hardware processor 2802 during execution thereof by the machine 2800. In an example, one or any combination of the hardware processor 2802, the main memory 2804, the static memory 2806, or the storage device 2816 may constitute machine readable media.

While the machine-readable medium 2822 is illustrated as a single medium, the term "machine readable medium" may include a single medium or multiple media (e.g., a centralized or distributed database, and/or associated caches and servers) configured to store the one or more instructions 2824.

The term "machine readable medium" may include any medium that is capable of storing, encoding, or carrying instructions for execution by the machine 2800 and that cause the machine 2800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 2824 may further be transmitted or received over a communication network 2826 using a transmission medium via the network interface device 2820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 2820 may include one or more physical jacks (e.g., Ethernet, coaxial, or phone jacks) or one or more antennas to connect to the communication network 2826. In an example, the network interface device 2820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 2800, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical feedback control system, comprising:
a feedback analyzer configured to receive a reflected signal from a target in response to electromagnetic radiation directed at a target; and
a controller in operative communication with the feedback analyzer, the controller configured to generate a control signal to a surgical system to perform a predetermined operation based upon the received reflected signal,
wherein the predetermined operation includes determining two or more distinct compositions of respective portions within the same target based at least in part on the received reflected signal,
wherein the two or more distinct compositions include distinct first and second compositions of respective first and second portions within the same target, and wherein the predetermined operation further includes delivering a treatment to the first portion while analyzing the second composition of the second portion via the surgical system.

2. The surgical feedback control system of claim 1, wherein:
the feedback analyzer includes, or is coupled to, a spectrometer configured to collect spectroscopic data based on the received reflected signal; and
the controller is configured to generate the control signal to the surgical system to perform the predetermined operation based on the spectroscopic data.

3. The surgical feedback control system of claim 1, comprising an optical fiber coupled to a radiation source, the optical fiber configured to transmit the electromagnetic radiation generated by the radiation source.

4. The surgical feedback control system of claim 1, comprising an optical fiber coupled to the feedback analyzer, the optical fiber configured to transmit the reflected signal to the feedback analyzer.

5. The surgical feedback control system of claim 1, comprising a camera configured to generate an image of the reflected signal for the feedback analyzer.

6. The surgical feedback control system of claim 1, wherein the target includes a calculi target, and wherein the controller is configured to, based upon the received reflected signal:
determine a first composition of a first portion of the calculi target; and
determine a second composition of a different second portion of the calculi target, the second composition being different from the first composition.

7. The system of claim 6, wherein the surgical system is a surgical laser system, and the controller is configured to generate a control signal to the surgical laser system to:
program a first laser setting or suggest a user to program the first laser setting to target the first portion of the calculi target; and
program a second laser setting or suggest the user to program the second laser setting to target the second portion of the calculi target, the second laser setting being different from the first laser setting.

8. The system of claim 1, wherein the controller is further configured to:
communicate with a cloud computing device to access a cloud service therein including a machine learning based target recognition engine; and
determine a composition of the target using the cloud service.

9. The system of claim 1, wherein the surgical system is a surgical laser system, and wherein the controller is configured to generate a control signal to the surgical laser system to adjust a laser setting or suggest a user to adjust a laser setting based upon the received reflected signal.

10. The system of claim 1, wherein the electromagnetic radiation includes one or more wavelengths between 10 nm to 400 nm.

11. The system of claim 1, wherein the electromagnetic radiation includes one or more wavelengths between 200 nm to 1100 nm.

12. The surgical feedback control system of claim 1, wherein the predetermined operation further includes controlling distinct treatment energy sources of the surgical system to deliver respective treatments to the respective portions of the same target.

13. A method of feedback control of a surgical system, the method comprising:
directing electromagnetic radiation at a target;
receiving a reflected signal from the target in response to the electromagnetic radiation at the target; and
generating a control signal to the surgical system to perform a predetermined operation based upon the received reflected signal, the predetermined operation including determining two or more distinct compositions of respective portions within the same target based at least in part on the received reflected signal,
wherein the two or more distinct compositions include distinct first and second compositions of respective first and second portions within the same target, and wherein the predetermined operation further includes delivering a treatment to the first portion while analyzing the second composition of the second portion via the surgical system.

14. The method of claim 13, comprising:
collecting spectroscopic data using a spectrometer based upon the received reflected signal; and
generating the control signal to the surgical system to perform the predetermined operation based upon the spectroscopic data.

15. The method of claim 13, wherein the target includes a calculi target, and wherein determining the two or more distinct compositions of the target comprises:
determining a first composition of a first portion of a calculi target; and
determining a second composition of a different second portion of the calculi target, the second composition being different from the first composition.

16. The method of claim 15, wherein the predetermined operation further comprises:
programming a first laser setting or suggesting a user to program the first laser setting to target the first portion of the calculi target; and
programming a second laser setting or suggesting the user to program the second laser setting to target the second portion of the calculi target, the second laser setting being different from the first laser setting.

17. The method of claim 13, further comprising:
establishing a communication with a cloud computing device and accessing a cloud service therein including a machine learning based target recognition engine; and
determining a composition of the target using the cloud service.

18. The method of claim 13, wherein the predetermined operation comprises adjusting a laser setting or suggesting a user to adjust a laser setting based upon the received reflected signal.

19. A non-transitory program storage device readable by a machine, tangibly embodying a program of instructions executable by the machine for performing operations, the operations comprising:
directing electromagnetic radiation at a target;
receiving a reflected signal from the target in response to the electromagnetic radiation at the target; and
generating a control signal to a surgical system to perform a predetermined operation based upon the received reflected signal, the predetermined operation including determining two or more distinct compositions of respective portions within the same target based at least in part on the received reflected signal,
wherein the two or more distinct compositions include distinct first and second compositions of respective first and second portions within the same target, and wherein the predetermined operation further includes delivering a treatment to the first portion while analyzing the second composition of the second portion via the surgical system.

20. The non-transitory program storage device of claim 19, wherein the operations comprise:
collecting spectroscopic data using a spectrometer based upon the received reflected signal; and
generating the control signal to the surgical system to perform the predetermined operation based upon the spectroscopic data.

21. The non-transitory program storage device of claim 19, wherein the control signal causes the surgical system to perform the predetermined operation including:
determining a first composition of a first portion of a calculi target; and
determining a second composition of a different second portion of the calculi target, the second composition being different from the first composition.

22. The non-transitory program storage device of claim 21, wherein the control signal causes the surgical system to perform the predetermined operation including:
programming a first laser setting or suggesting a user to program the first laser setting to target the first portion of the calculi target; and
programming a second laser setting or suggesting the user to program the second laser setting to target the second portion of the calculi target, the second laser setting being different from the first laser setting.

23. The non-transitory program storage device of claim 19, wherein the operations further comprise:
establishing a communication with a cloud computing device and accessing a cloud service therein including a machine learning based target recognition engine; and
determining a composition of the target using the cloud service.

24. The non-transitory program storage device of claim 19, wherein the control signal causes the surgical system to perform the predetermined operation including adjusting a laser setting or suggesting a user to adjust a laser setting based upon the received reflected signal.

* * * * *